(12) United States Patent
She et al.

(10) Patent No.: US 11,946,094 B2
(45) Date of Patent: Apr. 2, 2024

(54) COMBINATION THERAPIES AND METHODS OF USE THEREOF

(71) Applicant: Augusta University Research Institute, Inc., Augusta, GA (US)

(72) Inventors: Jin-Xiong She, Augusta, GA (US); Robert Schleifer, Sugar Hill, GA (US); Shuchun Li, Martinez, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 757 days.

(21) Appl. No.: 16/214,658

(22) Filed: Dec. 10, 2018

(65) Prior Publication Data

US 2019/0177765 A1    Jun. 13, 2019

Related U.S. Application Data

(60) Provisional application No. 62/596,888, filed on Dec. 10, 2017, provisional application No. 62/596,889, filed on Dec. 10, 2017.

(51) Int. Cl.
*C12Q 1/02* (2006.01)
*G01N 33/50* (2006.01)
*G01N 33/574* (2006.01)

(52) U.S. Cl.
CPC ......... *C12Q 1/025* (2013.01); *G01N 33/5008* (2013.01); *G01N 33/57496* (2013.01); *G01N 2500/02* (2013.01); *G01N 2500/10* (2013.01); *G01N 2800/44* (2013.01); *G01N 2800/52* (2013.01)

(58) Field of Classification Search
CPC ............... C12Q 1/025; G01N 33/5008; G01N 33/57496; G01N 2500/02; G01N 2500/10; G01N 2800/44; G01N 2800/52
See application file for complete search history.

(56) References Cited

U.S. PATENT DOCUMENTS

| | | | |
|---|---|---|---|
| 5,013,556 A | 5/1991 | Woodle | |
| 6,005,079 A | 12/1999 | Casterman | |
| 7,052,694 B2 | 5/2006 | Pease | |
| 7,390,888 B2 | 6/2008 | Pease | |
| 7,411,051 B2 | 8/2008 | Rosen | |
| 8,114,845 B2 | 2/2012 | Langermann | |
| 8,609,089 B2 | 12/2013 | Langermann | |
| 8,709,416 B2 | 4/2014 | Langermann | |
| 2006/0099203 A1 | 5/2006 | Pease | |

(Continued)

FOREIGN PATENT DOCUMENTS

| | | |
|---|---|---|
| WO | 9425591 | 11/1994 |
| WO | 03099196 A2 | 12/2003 |

(Continued)

OTHER PUBLICATIONS

Papadimitrakopoulou (Journal of Thoracic Oncology, vol. 7, No. 8, pp. 1315-1326, Aug. 2012) (Year: 2012).*

(Continued)

*Primary Examiner* — Jeremy C Flinders
(74) *Attorney, Agent, or Firm* — Smith, Gambrell & Russell; Judy Jarecki-Black

(57) ABSTRACT

A method for identifying drug resistant genes and compositions containing agents that downregulate these genes in combination with a cancer therapeutic.

6 Claims, 31 Drawing Sheets

Specification includes a Sequence Listing.

(56) References Cited

U.S. PATENT DOCUMENTS

| | | | |
|---|---|---|---|
| 2006/0110383 A1 | 5/2006 | Honjo | |
| 2016/0215349 A1* | 7/2016 | Lordan | G01N 33/57484 |
| 2019/0224200 A1* | 7/2019 | Martin | A61K 45/06 |
| 2021/0100752 A1* | 4/2021 | Kannan | A61K 31/713 |

FOREIGN PATENT DOCUMENTS

| | | |
|---|---|---|
| WO | 2004004771 A1 | 1/2004 |
| WO | 2004056875 | 7/2004 |
| WO | 2004072286 | 8/2004 |
| WO | 2006121168 | 11/2006 |
| WO | 2006133396 | 12/2006 |
| WO | 2007005874 | 1/2007 |
| WO | 2008083174 | 7/2008 |
| WO | 2009014708 | 1/2009 |
| WO | 2009073533 | 6/2009 |

OTHER PUBLICATIONS

Liu et al. (Tumor Biology, 2017, doi.org/10.1177/1010428317705337) (Year: 2017).*

Liu et al. (Experimental and Therapeutic Medicine 9: 1460-1464, 2015) (Year: 2015).*

Hao et al. (Mol Cell Biochem (2012) 359:323-332) (Year: 2012).*

Luis Korrodi-Gregorio et al. (Plos One | DOI:10.1371/journal.pone.0165973) (Year: 2016).*

Wang et al. (Int. J. Med. Sci. 2013, vol. 10, pp. 1552-1559) (Year: 2013).*

Wang et al. (Theranostics 2016, vol. 6, Issue 8, pp. 1205-1219) (Year: 2016).*

Woo et al. (Plos One | DOI:10.1371/journal.pone.0142642) (Year: 2015).*

Asghar, Uzma et al., "The History and Future of Targeting Cyclin-Dependent Kinases in Cancer Therapy", Nat Rev Drug Discov, 14(2):130-146 (2015).

Atanassov, Boyko S. et al., "USP22 Regulates Cell Proliferation by Deubiquitinating the Transcriptional Regulator FBP1", Embo Rep, 12:924-930 (2011).

Bai, Jingwen et al., "Cell Cycle Regulation and Anticancer Drug Discovery", Cancer Biol Med, 14:348-362 (2017).

Bass, K.K. et al., "Immunopotentiation with Low-Dose Cyclophosphamide in the Active Specific Immunotherapy of Cancer", Cancer Immunol. Immunother, 47(1):1-12 (1998). (Abstract Only).

Berger, Raanan et al., "Phase I Safety and Pharmacokinetic Study of CT-011, a Humanized Antibody Interacting with PD-1, in Patients with Advanced Hematologic Malignancies", Clin Cancer Res, 14(10):3044-3051 (2008).

Brode, S. et al., "Immune-Potentiating Effects of the Chemotherapeutic Drug Cyclophosphamide", Crit Rev Immunol, 28(2):109-126 (2008). (Abstract Only).

Butte, Manish J. et al., "PD-L1 Interacts Specifically with B7-1 to Inhibit T Cell Proliferation", Immunity, 27(1):111-122 (2007).

Byers, Lauren Averett et al., "An Epithelial-Mesenchymal Transition Gene Signature Predicts Resistance to EGFR and P13K Inhibitors and Identifies Axl as a Therapeutic Target for Overcoming EGFR Inhibitor Resistance", Clin Canc Res, 19:279-290 (2013). (Abstract Only).

Chae, Young Kwang et al., "Inhibition of the Fibroblast Growth Factor Receptor (FGFR) Pathway: The Current Landscape and Barriers to Clinical Application", Oncotarget, 8:16052-16074 (2017).

Chothia, Cyrus et al., "Canonical Structures for the Hypervariable Regions of Immunoglobulins". J Mol Biol, 196 (4): 901-917 (1987). (Abstract Only).

Cubillos-Ruiz, Juan R. et al., "Polyethylenimine-Based siRNA Nanocomplexes Reprogram Tumor-Associated Dendritic Cells via TLR5 to Elicit Therapeutic Antitumor Immunity", J Clin Invest 119(8): 2231-2244 (2009).

Deng, Yanhong et al., "High SLFN11 Expression Predicts Better Survival for Patients with KRAS Exon 2 Wild Type Colorectal Cancer after Treated with Adjuvant Oxaliplatin-Based Treatment", BMC Cancer, 15:833 (2015).

Dhanoa, Bajinder S. et al., "Update on the Kelch-Like (KLHL) Gene Family", Hum Gen, 7:13 (2013).

Eckschlager, Tomas et al., "Histone Deacetylase Inhibitors as Anticancer Drugs", Int J Mol Sci, 18:1414 (2017).

Erbe, David V. et al., "Small Molecule Ligands Define a Binding Site on the Immune Regulatory Protein B7.1", J Biol Chem, 277(9):7363-7368 (2002).

Foertsch, Franziska et al., "S100A11 is Involved in the Regulation of the Stability of Cell Cycle Regulator p21 (CIP1/WAF1) in Human Keratinocyte HaCaT Cells", The FEBS Journal, 280: 3840-3853 (2013).

Freeman, Gordon J. "Structures of PD-1 with its Ligands: Sideways and Dancing Cheek to Cheek", Proc Natl Acad Sci U. S. A, 105(30):10275-10276 (2008).

Gottesman, Michael M. et al., "Multidrug Resistance in Cancer: Role of ATP-Dependent Transporters", Nat Rev Cancer 2: 48-58 (2002).

Hengst, James C.D. et al., "Importance of Timing of Cyclophosphamide Therapy of MOPC-315 Tumor-Bearing Mice", Cancer Res, 40:2135-2141 (1980).

Hengst, James C.D. et al., "Cooperation Between Cyclophosphamide Tumoricidal Activity and Host Antitumor Immunity in the Cure of Mice Bearing Large MOPC-315 Tumors", Cancer Res, 41:2163-2167 (1981).

Holohan, Caitriona et al., "Cancer Drug Resistance: An Evolving Paradigm", Nat Rev Cancer, 13: 714-726 (2013).

Hong, Chih-Chen et al., "Receptor Tyrosine Kinase AXL is Induced by Chemotherapy Drugs and Overexpression of AXL Confers Drug Resistance in Acute Myeloid Leukemia", Cancer Letters, 268:314-324 (2008).

Hong, Jun et al. "ABL Regulation by AXL Promotes Cisplatin Resistance in Esophageal Cancer", Cancer Research, 73(1):331-340 (2013).

Huang, Ying et al., "Cystine-Glutamate Transporter SLC7A11 in Cancer Chemosensitivity and Chemoresistance", Cancer Research, 65(16): 7446-7454 (2005).

Khamisipour, Gholamreza et al., "Mechanisms of Tumor Cell Resistance to the Current Targeted-Therapy Agents", Tumor Biology, 37: 10021-10039 (2016).

Korshunov, Vyacheslav A., "Axl-Dependent Signalling: A Clinical Update", Clinical Science, 122:361-368 (2012).

Lazar-Molnar, Eszter et al., "Crystal Structure of the Complex Between Programmed Death-1 (PD-1) and its Ligand PD-L2", PNAS, 105:10483-10488 (2008).

Li, Betty et al., "Vascular Endothelial Growth Factor Blockade Reduces Intratumoral Regulatory T Cells and Enhances the Efficacy of a GM-CSF-Secreting Cancer Immunotherapy", Clin Cancer Res, 12(22):6808-6816 (2006).

Liang, Jun et al., "Design of New Oxazaphosphorine Anticancer Drugs", Curr Pharm Des, 13(9):963-978 (2007).

Liu, Ruqing et al., "Cystine-Glutamate Transporter SLC7A11 Mediates Resistance to Geldanamycin but not to 17-(Allylamino)-17-Demethoxygeldanamycin", Molecular Pharmacology, 72(6):1637-1646 (2007).

Machiels, Jean-Pascal H. et al., "Cyclophosphamide, Doxorubicin, and Paclitaxel Enhance the Antitumor Immune Response of Granulocyte/Macrophage-Colony Stimulating Factor-Secreting Whole-Cell Vaccines in HER-2/ heu Tolerized Mice", Cancer Res, 61:3689-3697 (2001).

Mathiowitz E. et al,, "Polyanhydride Microspheres as Drug Carriers. I. Hot-Melt Microencapsulation", J Controlled Release, 5:13-22 (1987).

Mathiowitz E. et al., "Novel Microcapsules for Delivery Systems", Reactive Polymers, 6:275-283 (1987).

Mathiowitz E. et al., "Polyanhydride Microspheres as Drug Carriers. II. Microencapsulation by Solvent Removal", J Appl Polymer Sci, 35:755-774 (1988).

(56) References Cited

OTHER PUBLICATIONS

Muyldermans Serge et al., "Recognition of Antigens by Single-Domain Antibody Fragments: The Superfluous Luxury of Paired Domains", Trends Biochem Sci, 26(4):230 (2001).
Newmark, J. et al., "Preparation and Properties of Adducts of Streptokinase and Streptokinase-Plasmin Complex with Polyethylene Glycol and Pluronic Polyol F38", J Appl Biochem, 4:185-189 (1982).
Niederst, Matthew J., et al., "Bypass Mechanisms of Resistance to Receptor Tyrosine Kinase Inhibition in Lung Cancer", Science Signaling, 6(294):re6 (2013).
Niu, Ya et al., "LASP1-S100A11 Axis Promotes Colorectal Cancer Aggressiveness by Modulating TGFBeta/Smad Signaling", Sci Rep, 6:26112 (2016).
Nuttall, S.D. et al., "Immunoglobulin V11 Domains and Beyond: Design and Selection of Single-Domain Binding and Targeting Reagents", Cur Pharm Biotech, 1:253 (2000).
Pham, Anh-Nhan et al., "Pharmacogenomic Approach Reveals a Role for the x(c)-Cystine/Glutamate Antiporter in Growth and Celastrol Resistance of Glioma Cell Lines", The Journal of Pharmacology and Experimental Therapeutics, 332(3):949-958 (2010).
Quesada, Victor et al., "Cloning and Enzymatic Analysis of 22 Novel Human Ubiquitin-Specific Proteases", Biochemical and Biophysical Research Communications, 314:54-62 (2004).
Rehman, Ishtiaq Ph.d., et al., "Dysregulated Expression of S100A11 (Calgizzarin) in Prostate Cancer and Precursor Lesions", Human Pathology 35:1385-1391 (2004).
Riechmann, Lutz et al., "Single Domain Antibodies: Comparison of Camel VH and Camelised Human VH Domains", J Immunol Meth, 231:25 (1999).
Rho, Jin Kyung et al., "MET and AXL Inhibitor NPS-1034 Exerts Efficacy Against Lung Cancer Cells Resistant to EGFR Kinase Inhibitors Because of MET or AXL Activation", Canc Res, 74:253-262 (2014).
Rhodes, Daniel R., et al., "Oncomine 3.0: Genes, Pathways, and Networks in a Collection of 18,000 Cancer Gene Expression Profiles", Neoplasia, 9(2):166-180 (2007).
Sakaguchi, Masakiyo et al., "S100A11, An Dual Mediator for Growth Regulation of Human Keratinocytes", Molecular Biology of the Cell, 19:78-85 (2008).

Samatar, Ahmed A. et al., "Targeting RAS-ERK Signalling in Cancer: Promises and Challenges", Nat Rev Drug Discov, 13:928-942 (2014).
Sammartino, Christine et al., "Anti-GBM Disease Following CTLA4 Blockage in a Patient with Metastatic Melanoma", Clinical Kidney Journal, 3(2):135-137 (2010).
Szasz, A. Marcell et al., "Cross-Validation of Survival Associated Biomarkers in Gastric Cancer Using Transcriptomic Data of 1,065 Patients", Oncotarget, 7(31) 49322-49333 (2016).
Taieb, Julien et al., "Chemoimmunotherapy of Tumors: Cyclophosphamide Synergizes with Exosome Based Vaccines", J Immunol, 176:2722-2729 (2006).
Takagi Hisashi et al., "USP40 Gene Knockdown Disrupts Glomerular Permeability in Zebrafish", Am J Physiol Renal Physiol, 312:F702-F715 (2017).
Takeuchi, Satoru et al., "Increased xCT Expression Correlates with Tumor Invasion and Outcome in Patients with Glioblastomas", Neurosurgery, 72(1), 33-41; Discussion 41 (2013).
Van der Most, Robbert G. et al., "Tumor Eradication after Cyclophosphamide Depends on Concurrent Depletion of Regulatory T Cells: A Role for Cycling TNFR2-Expressing Effector-Suppressor T Cells in Limiting Effective Chemotherapy", Cancer Immunol Immunother, 58:1219-1228 (2009).
Vucic, Domagoj et al., "Ubiquitylation in Apoptosis: A Post-Translational Modification at the Edge of Life and Death", Nature Reviews Molecular Cell Biology, 12:439-452 (2011).
Wang, Guiyu et al., "Colorectal Cancer Progression Correlates with Upregulation of S100A11 Expression in Tumor Tissues", Int J Colorectal Dis, 23:675-682 (2008).
Wu, Jianzhong et al., "Tumor Profiling of Co-Regulated Receptor Tyrosine Kinase and Chemoresistant Genes Reveal Different Targeting Options for Lung and Gastroesophageal Cancers", Am J Transl Res, 8(12):5729-5740 (2016).
Zhao, Yujie et al., "The Clinical Development of MEK Inhibitors", Nat Rev Clin Oncol, 11:385-400 (2014).
Zoppoli, Gabriele et al., "Putative DNA/RNA Helicase Schlafen-11 (SLFN11) Sensitizes Cancer Cells to DNA-Damaging Agents", Proceedings of the National Academy of Sciences of the United States of America, 109(37):15030-15035 (2012).

* cited by examiner

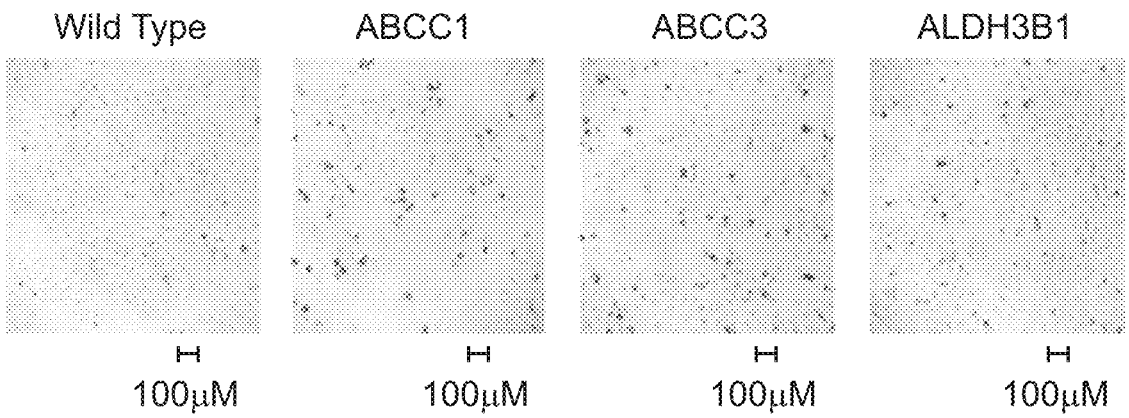
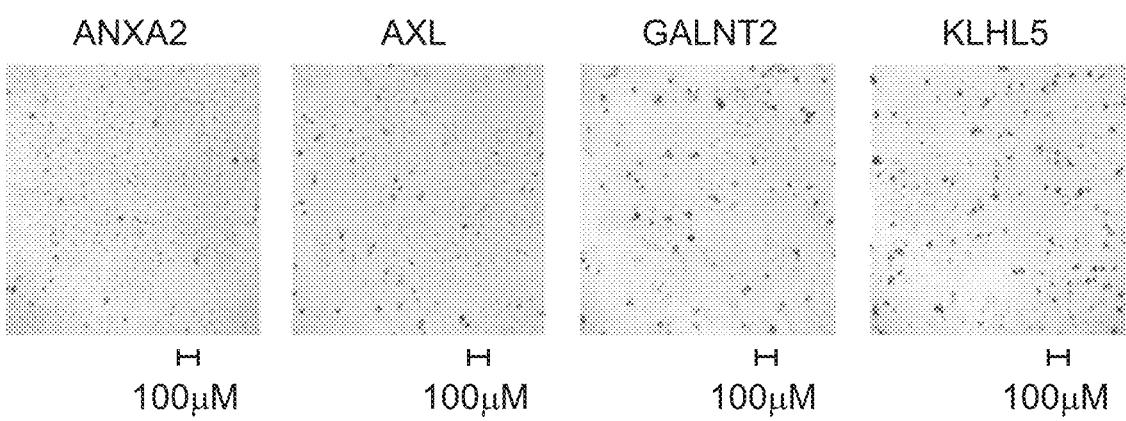
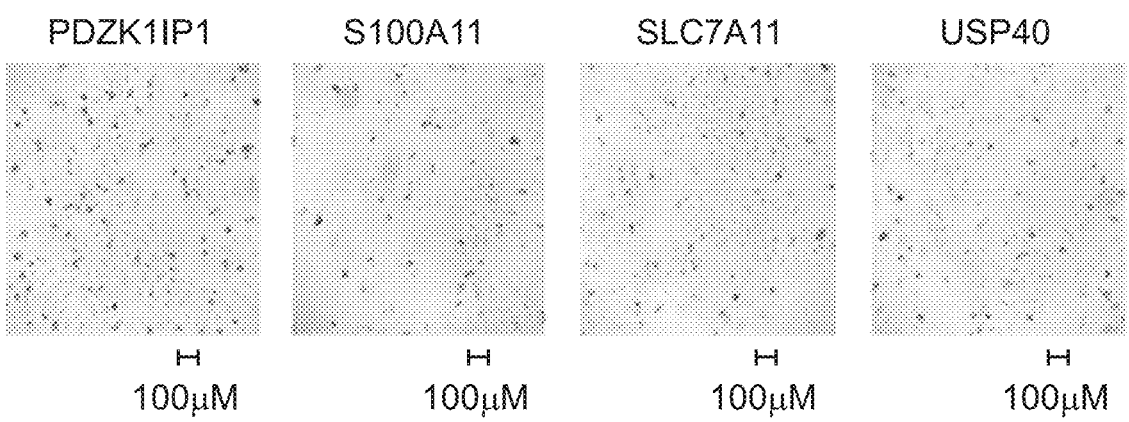

| | kd | A549 | MEL2 | OVCAR-8 | SN12C |
|---|---|---|---|---|---|
| Scramble | | 1 | 1 | 1 | 1 |
| ABCB1 | 0.98 | 1.1 | 0.78 | 1.1 | 0.95 |
| ABCC1 | 0.2 | 0.77 | 0.82 | 0.81 | 0.9 |
| ABCC3 | 0.04 | 0.95 | 0.87 | 1.1 | 1 |
| AJUBA | 1.3 | 1 | 0.91 | 0.97 | 0.97 |
| AKR1C3 | 0.31 | 0.99 | 0.92 | 1 | 0.97 |
| ALDH3B1 | 0.13 | 0.98 | 0.75 | 0.95 | 0.98 |
| ANXA2 | 0.1 | 1 | 1.1 | 1 | 1 |
| AXL | 0.13 | 0.99 | 1 | 1 | 1 |
| BLM | 0.89 | 0.93 | 0.81 | 0.98 | 0.94 |
| EGFR | 0.91 | 1 | 0.96 | 1.1 | 0.98 |
| GALNT2 | 0.19 | 0.21 | 0.41 | 0.4 | 0.66 |
| KLHL5 | 0.08 | 1 | 0.83 | 0.96 | 0.95 |
| PDZK1IP1 | 0.08 | 1 | 0.72 | 0.53 | 0.97 |
| S100A11 | 0.05 | 1 | 0.56 | 0.75 | 0.91 |
| SLC18B1 | 0.78 | 0.98 | 0.86 | 0.98 | 0.98 |
| SLC7A11 | 0.29 | 1 | 0.53 | 0.86 | 0.8 |
| SLFN13 | 0.94 | 1 | 0.54 | 1.1 | 1 |
| USP40 | 0.25 | 0.37 | 0.8 | 0.7 | 0.88 |

FIG.6A

SEQUENCE LISTING

```
<160> NUMBER OF SEQ ID NOS: 38

<210> SEQ ID NO 1
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n= t

<400> SEQUENCE: 1
cauucgcuau ggccgugaan n                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 2
uucacggcca uagcgaaugn n                                              21

<210> SEQ ID NO 3
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 3
ggaugucauc ugaaauggan n                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = g
<220> FEATURE:
<221> NAME/KEY: misc_feature
<222> LOCATION: (21)..(21)
<223> OTHER INFORMATION: n = a

<400> SEQUENCE: 4
uccauuucag augacauccn n                                              21
```

```
<210> SEQ ID NO 5
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 5
ggguguacgu guacguggan n                                              21

<210> SEQ ID NO 6
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = a
<220> FEATURE:
<221> NAME/KEY: misc_feature
<222> LOCATION: (21)..(21)
<223> OTHER INFORMATION: n = g

<400> SEQUENCE: 6
uccacguaca cguacacccn n                                              21

<210> SEQ ID NO 7
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 7
gcggcucaau gcccgacaan n                                              21

<210> SEQ ID NO 8
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = t
<220> FEATURE:
<221> NAME/KEY: misc_feature
<222> LOCATION: (21)..(21)
<223> OTHER INFORMATION: n = g

<400> SEQUENCE: 8
uugucgggca uugagccgcn n                                              21

<210> SEQ ID NO 9
<211> LENGTH: 21
<212> TYPE: RNA
<213> ORGANISM: Artificial Sequence
<220> FEATURE:
<223> OTHER INFORMATION: Synthetic siRNA
<220> FEATURE:
```

```
<221> NAME/KEY: misc_feature
<222> LOCATION: (20)..(21)
<223> OTHER INFORMATION: n = t

<400> SEQUENCE: 9
ggaguaaauu gcuagauuun n                                              21

<210> SEQ ID NO 10
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = g

<400> SEQUENCE: 10
aaaucuagca auuuacuccn n                                              21

<210> SEQ ID NO 11
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 11
ggagagaauu aaccauugan n                                              21

<210> SEQ ID NO 12
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = a
<220> FEATURE:
<221> NAME/KEY: misc_feature
<222> LOCATION: (21)..(21)
<223> OTHER INFORMATION: n = c

<400> SEQUENCE: 12
ucaaugguua auucucuccn n                                              21

<210> SEQ ID NO 13
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 13
gcaagucccu guacuauuan n                                              21

<210> SEQ ID NO 14
<211> LENGTH: 21
```

```
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = c
<220> FEATURE:
<221> NAME/KEY: misc_feature
<222> LOCATION: (21)..(21)
<223> OTHER INFORMATION: n = g

<400> SEQUENCE: 14
uaauaguaca gggacuugcn n                                              21

<210> SEQ ID NO 15
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 15
cagcgagauu uaugacuaun n                                              21

<210> SEQ ID NO 16
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 16
auagucauaa aucucgcugn n                                              21

<210> SEQ ID NO 17
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 17
cgcuagacag auaaguuuan n                                              21

<210> SEQ ID NO 18
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = t
<220> FEATURE:
<221> NAME/KEY: misc_feature
<222> LOCATION: (21)..(21)
```

<223> OTHER INFORMATION: n = c

<400> SEQUENCE: 18
uaaacuuauc ugucuagcgn n                                              21

<210> SEQ ID NO 19
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 19
cgaauauuaa acacuucaan n                                              21

<210> SEQ ID NO 20
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = t
<220> FEATURE:
<221> NAME/KEY: misc_feature
<222> LOCATION: (21)..(21)
<223> OTHER INFORMATION: n = a

<400> SEQUENCE: 20
uugaaguguu uaauauucgn n                                              21

<210> SEQ ID NO 21
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 21
gauuggaacu ugguauucan n                                              21

<210> SEQ ID NO 22
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = a

<400> SEQUENCE: 22
ugaauaccaa guuccaaucn n                                              21

<210> SEQ ID NO 23
<211> LENGTH: 21
<212> TYPE: RNA
<213> ORGANISM: Artificial Sequence

```
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 23
caggccgccu ugaauuaaan n                                              21

<210> SEQ ID NO 24
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = t
<220> FEATURE:
<221> NAME/KEY: misc_feature
<222> LOCATION: (21)..(21)
<223> OTHER INFORMATION: n = a

<400> SEQUENCE: 24
uuuaauucaa ggcggccugn n                                              21

<210> SEQ ID NO 25
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 25
gguccaguga gcaugagaan n                                              21

<210> SEQ ID NO 26
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = t
<220> FEATURE:
<221> NAME/KEY: misc_feature
<222> LOCATION: (21)..(21)
<223> OTHER INFORMATION: n = g

<400> SEQUENCE: 26
uucucaugcu cacuggaccn n                                              21

<210> SEQ ID NO 27
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t
```

```
<400> SEQUENCE: 27
gaacuagcug ccuucacaan n                                          21

<210> SEQ ID NO 28
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = t
<220> FEATURE:
<221> NAME/KEY: misc_feature
<222> LOCATION: (21)..(21)
<223> OTHER INFORMATION: n = g

<400> SEQUENCE: 28
uugugaaggc agcuaguucn n                                          21

<210> SEQ ID NO 29
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 29
gugcugauau uaguuguaan n                                          21

<210> SEQ ID NO 30
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = c
<220> FEATURE:
<221> NAME/KEY: misc_feature
<222> LOCATION: (21)..(21)
<223> OTHER INFORMATION: n = a

<400> SEQUENCE: 30
uuacaacuaa uaucagcacn n                                          21

<210> SEQ ID NO 31
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 31
ggcugauuua ucuucgauan n                                          21

<210> SEQ ID NO 32
<211> LENGTH: 21
```

```
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = c
<220> FEATURE:
<221> NAME/KEY: misc_feature
<222> LOCATION: (21)..(21)
<223> OTHER INFORMATION: n = a

<400> SEQUENCE: 32
uaucgaagau aaaucagccn n                                      21

<210> SEQ ID NO 33
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 33
gcuguauacc agaacauaun n                                      21

<210> SEQ ID NO 34
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 34
auauguucug guauacagcn n                                      21

<210> SEQ ID NO 35
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 35
ggaaacuagc uguuauacan n                                      21

<210> SEQ ID NO 36
<211> LENGTH: 21
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(21)
<223> OTHER INFORMATION: n = t

<400> SEQUENCE: 36
```

```
uguauaacag cuaguuuccn n                                           21
```

```
<210> SEQ ID NO 37
<211> LENGTH: 25
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = a
<220> FEATURE:
<221> NAME/KEY: misc_feature
<222> LOCATION: (21)..(21)
<223> OTHER INFORMATION: n = t
<220> FEATURE:
<221> NAME/KEY: misc_feature
<222> LOCATION: (24)..(25)
<223> OTHER INFORMATION: n is a, c, g, or u

<400> SEQUENCE: 37
cguuaaucgc guauaauacg cgunn                                       25

<210> SEQ ID NO 38
<211> LENGTH: 27
<212> TYPE: RNA
<213> ORGANISM: Artificial Sequence
<220> FEATURE:
<223> OTHER INFORMATION: Synthetic siRNA
<220> FEATURE:
<221> NAME/KEY: misc_feature
<222> LOCATION: (20)..(20)
<223> OTHER INFORMATION: n = a
<220> FEATURE:
<221> NAME/KEY: misc_feature
<222> LOCATION: (21)..(21)
<223> OTHER INFORMATION: n = c
<220> FEATURE:
<221> NAME/KEY: misc_feature
<222> LOCATION: (26)..(27)
<223> OTHER INFORMATION: n is a, c, g, or u

<400> SEQUENCE: 38
auacgcguau uauacgcgau uaacgnn                                     27
```

COMBINATION THERAPIES AND METHODS OF USE THEREOF

CROSS-REFERENCE TO RELATED APPLICATIONS

This application claims benefit of and priority to U.S. Provisional Application Nos. 62/596,888 filed on Dec. 10, 2017 and 62/596,889 filed on Dec. 10, 2017, both of which are incorporated by reference in their entirety.

STATEMENT REGARDING FEDERALLY SPONSORED RESEARCH OR DEVELOPMENT

This invention was made with government support under CA199868 awarded by the National Institutes of Health. The government has certain rights in the invention.

REFERENCE TO SEQUENCE LISTING

The Sequence Listing submitted Dec. 10, 2018, as a text file named "064466.084_sequence_listing.txt" created on Nov. 19, 2018 and having a size of 10.7 kilobytes is hereby incorporated by reference pursuant to 37 C.F.R. § 1.52(e)(5).

FIELD OF THE INVENTION

The invention is generally related to the field of cancer therapeutics and methods of their use.

BACKGROUND OF THE INVENTION

The effectiveness of anticancer drugs varies greatly from patient to patient as well as in in vitro and in vivo laboratory models. This differential response by cancer cells and eventual therapeutic outcomes of patients are believed to be largely derived from differences in gene mutations, gene expression levels, protein expression and post-translational modifications (Holohan, C. et al., *Nat Rev Cancer*, 13:714-726 (2013); Khamisipour, G., et al., *Tumor Biology*, 37:10021-10039 (2016)). Defining these molecular differences using omic profiles of patients is a strategy that aims to deliver tailored personalized medicine and greatly improve the survival of patients with various types of cancers. However, molecular markers for drug efficacy and prognosis of therapeutic response remain scarce. Identification of the genes that modulate the effectiveness of drugs, often referred to as drug resistance genes, would provide biomarkers to guide prescription of more efficacious therapies. As the function of drug resistance genes is often integral to the survival of the patient, they offer intriguing targets for therapies.

Drug resistance presents a challenge for patients receiving chemotherapy or targeted therapy alike. Paradigms of cancer drug resistance often emphasize the development of resistance through acquisition of a mutation (such as a mutation in the targeted tyrosine kinase) or by induction and upregulated expression of specific drug resistance genes such as ABCB1, EGFR, or AXL. To elucidate drug resistance mechanisms, investigators typically attempt to induce resistance by exposing in vitro cancer cell lines (CCLs) to a drug or identify molecular differences in resistant patient samples to attempt to identify causative irregularities. These methodologies are notably limited in identifying innate characteristics that confer intrinsic resistance as opposed to resistance acquired over time. As such, most of the identified resistance genes follow up-regulation patterns. For example, upregulation of AXL allows for pathway switching in key signal transduction pathways to promote pro-survival, anti-apoptotic, and pro-proliferative signaling (Korshunov, V. S., *Clinical Science*, 122:361-368 (2012)). Signaling switches to parallel signaling cascades is a mechanism of drug resistance common in resistance to tyrosine kinase inhibitors (TKIs) (Niederst, M J and Engelman, J. A., *Science Signaling*, 6:re6 (2013)). This is contrasted with multidrug resistance where increased ABCB1 expression causes expression of Multidrug Resistance Protein 1 (MDR1) which primarily leads to increased efflux of chemotherapeutic drugs (Gottesman, M. M., et al., *Nat Rev Cancer*, 2:48-58 (2002)). With the diversity of mechanisms of actions for the FDA-approved anticancer drugs and those in the development pipelines, it is expected that the majority of drug resistance genes, especially those which impact intrinsic drug resistance or do not exhibit expression change upon treatment are yet to be discovered and explored for anticancer therapy.

It has increasingly been recognized that a single agent or drug target may be insufficient to achieve adequate and long-term tumor control because of marginal therapeutic efficacy and/or rapid development of drug resistance. Therefore, combination therapy using multiple agents targeting multiple proteins represents one of the new hopes for better anticancer therapies.

It is an object of this invention to provide compositions and methods for combination therapy for cancer therapeutics.

Another object of this invention is to provide systems and methods for identifying drug sensitivity genes and gene sensitivity altering compounds.

SUMMARY OF THE INVENTION

Compositions and methods for combination therapy for cancer therapeutics are provided herein. One embodiment provides a pharmaceutical composition having a an effective amount of a compound that inhibits (1) the PI3K-AKT-mTOR pathway, (2) Cell Cycle Inhibitors, or (3) the MEK-MAPK (ERK) pathway; or an HDAC inhibitor in combination with a compound that inhibits or reduces expression of AXL, SLFN13, ANXA2, S100A11, KLHL5, SLC7A11, AVCVA, USP40 or a combination thereof. The compound that inhibits or reduces expression or inhibits the pathway is siRNA, shRNA, antisense oligonucleotides, CRISPR/CAS constructs, a small molecule, an aptamer, an antibody or antigen binding fragment thereof, or a fusion protein.

Another embodiment provides a method for reducing tumor burden in a subject in need thereof, by administering to the subject a composition having an effective amount of an inhibitor of PI3K-AKT-mTOR pathway, cell cycle inhibitor, MEK-MAPK pathway inhibitor, or an HDAC inhibitor in combination with an effective amount of a compound that inhibits or reduces the expression of one or more drug resistance genes, wherein reducing the expression of the drug resistance gene increases the effectiveness of the inhibitor. The drug resistance gene can be selected from the group consisting of AXL, SLFN13, ANXA2, S100A11, KLHL5, SLC7A11, AVCVA, USP40 or a combination thereof. The inhibitors can be administered simultaneously or sequentially. The method can also include administering to the subject a PD-1 antagonist. The tumor can be from a cancer that is selected from the group consisting of bladder, brain, breast, cervical, colo-rectal, esophageal, kidney, liver, lung, nasopharangeal, pancreatic, prostate, skin, stomach, uterine, ovarian, testicular and hematologic cancers. The expression level of drug resistance genes in the tumor can be quantified in order to determine which composition to administer.

One embodiment provides a method for identifying drug resistance genes including identifying genes from the NCI-60 dataset with large numbers of negative correlations to cancer therapeutics, calculating Pearson-correlations between gene expression and cancer therapeutic, ranking genes according to their Pearson-correlations, selecting genes with the highest likelihood of resistance to a cancer therapeutic, and producing a composition comprising an inhibitor of the drug resistance gene and a second cancer therapeutic. In one embodiment, all of the genes from the NCI-60 dataset are utilized for the correlations ranking. In another embodiment, the leukemia lines from the NCI-60 dataset are excluded. Ranking genes can also include calculating the number of compounds with Pearson correlation coefficients beyond −0.5 for negative correlation rankings.

BRIEF DESCRIPTION OF THE DRAWINGS

FIGS. 2B-2M are representative light microscopy images of shRNA knockdown cells for select genes impacting viability/proliferation. Images were taken 72 hours after exposure to shRNA lentivirus in OVCAR-8 cells. Data are representative of three replicates.

FIGS. 5E-5F show the viability for combination of knockdown and drug at the $GI_{50}$ concentration observed in knockdown-free (sham control) cells. FIGS. 5G-5H show dose reduction of $GI_{50}$ value. Serial dilution of drugs was used to determined $GI_{50}$ values. Data represent means±s.d. from three replicates.

FIG. 6A shows relative gene expression (qRT-PCR) 72 hours after exposure to shRNA with four cell lines after 72 hours. Data represents average of three replicates.

FIG. 7A shows modeling of experimental standard deviation across replicates for all tests. FIG. 7B-7C show plotting CDI: $V_{AB}/(V_A \times V_B)$ and difference in viability $V_{AB}-V_A \times V_B$.

DETAILED DESCRIPTION OF THE INVENTION

I. Definitions

Figure 1A:
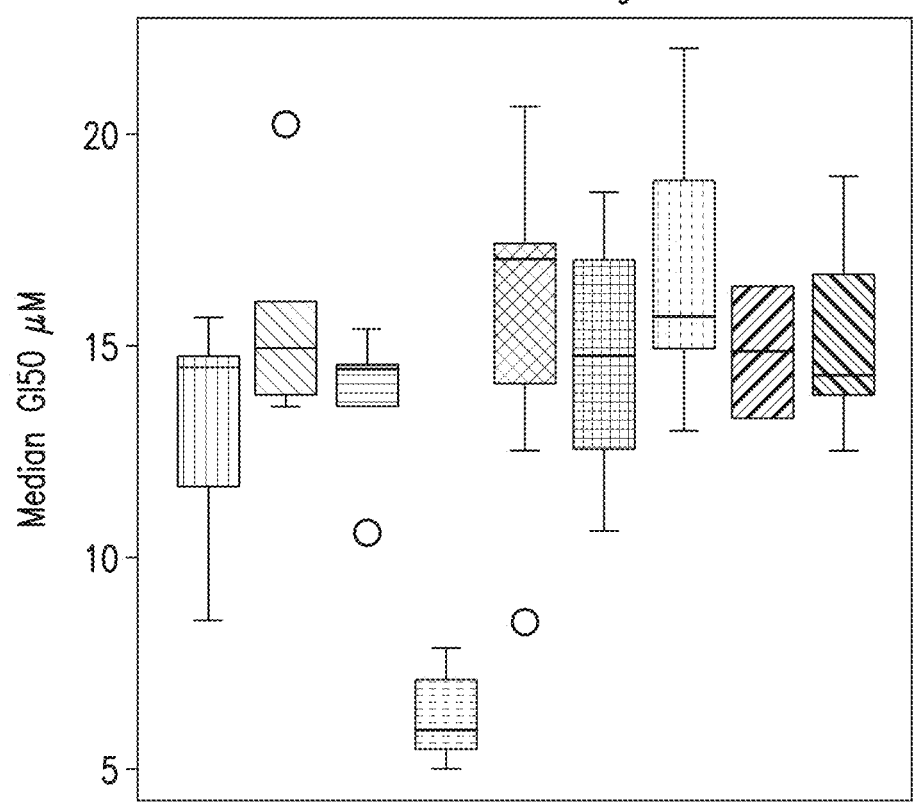
FIG. 1A shows a boxplot of median $GI_{50}$ values for NCI-60 cell lines grouped by tissue of origin. Data were obtained from CellMiner™.

As used herein, a molecule is said to be able to "immunospecifically bind" a second molecule if such binding exhibits the specificity and affinity of an antibody to its cognate antigen. Antibodies are said to be capable of immunospecifically binding to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. In some embodiments, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, a molecule is said to "physiospecifically bind" a second molecule if such binding exhibits the specificity and affinity of a receptor to its cognate binding ligand. A molecule can be capable of physiospecifically binding to more than one other molecule.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, MD. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', F(ab')$_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

As used herein the term "modulate" relates to a capacity to alter an effect, result, or activity (e.g., signal transduction). Such modulation can be agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. In some embodiments, such modulation will provide at least a 10% change in a measurable immune system activity, at least a 50% change in such activity, or at least a 2-fold, 5-fold, 10-fold, or at least a 100-fold change in such activity.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the "co-stimulatory" signals encompass positive co-stimulatory signals (e.g., signals that result in enhancing an activity) and negative co-stimulatory signals (e.g., signals that result in inhibiting an activity).

The term "derivative" refers to an antibody or antigen-binding fragment thereof that immunospecifically binds to the same target of a parent or reference antibody but which differs in amino acid sequence from the parent or reference antibody or antigen binding fragment thereof by including one, two, three, four, five or more amino acid substitutions, additions, deletions or modifications relative to the parent or reference antibody or antigen binding fragment thereof. In some embodiments such derivatives will have substantially the same immunospecificity and/or characteristics, or the same immunospecificity and characteristics as the parent or reference antibody or antigen binding fragment thereof. The amino acid substitutions or additions of such derivatives can include naturally occurring (i.e., DNA-encoded) or non-naturally occurring amino acid residues. The term "derivative" encompasses, for example, chimeric or humanized variants, as well as variants having altered CH1, hinge, CH2, CH3 or CH4 regions, so as to form, for example antibodies, etc., having variant Fc regions that exhibit enhanced or impaired effector or binding characteristics.

As used herein, a "chimeric antibody" is a molecule in which different portions of the antibody are derived from different immunoglobulin molecules such as antibodies having a variable region derived from a non-human antibody and a human immunoglobulin constant region.

As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they should be substantially identical to human immunoglobulin constant regions, i.e., at least about 85-99%, or about 95% or more identical. Hence, all parts of a humanized immunoglobulin, except possibly the CDR's, are substantially identical to corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human.

The term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "cancer" refers to a neoplasm or tumor resulting from abnormal uncontrolled growth of cells. As used herein, cancer explicitly includes, leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

As used herein, an "immune cell" refers to any cell from the hemopoietic origin including, but not limited to, T cells, B cells, monocytes, dendritic cells, and macrophages.

As used herein, "inflammatory molecules" refer to molecules that result in inflammatory responses including, but not limited to, cytokines and metalloproteases such as including, but not limited to, IL-1β, TNF-α, TGF-beta, IFN-γ, IL-18, IL-17, IL-6, IL-23, IL-22, IL-21, and MMPs.

As used herein, "valency" refers to the number of binding sites available per molecule.

As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

As used herein, the terms "individual," "host," "subject," and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, "NCI-60" refers to a collection of sixty cell lines developed by investigators at the National Cancer Institute. The panel includes sixty cell lines from nine tumor origins including breast, colon, CNS, leukemia, non-small-cell lung, melanoma, prostate, ovarian, and renal.

II. Combination Therapies and Methods of Use Thereof

Disclosed herein are compositions and methods for treating cancer in a subject in need thereof. One embodiment provides combination therapies including a compound that inhibits the PI3K-AKT-mTOR pathway, cell cycle, MEK-MAPK (ERK) pathway, or an HDAC inhibitor in combination with a compound that inhibits or reduces the expression of AXL, SLFN13, ANXA2, S100A11, KLHL5, SLC7A11, AVCVA, USP40 or a combination thereof.

Also disclosed are methods for identifying drug resistance genes and drugs that can be used to target said genes. An exemplary method includes a genome-wide rankings strategy that leverages the NCI-60 dataset.

A. Genes that Impact Drug Sensitivity and Resistance

One embodiment provides genes that impact drug sensitivity and resistance. Drug resistance can be defined as the failure of a compound to reach the intended outcome due to an interfering mechanism. Anti-cancer drugs typically exploit sensitivities of cancer cells. Typically, a drug will suppress proliferation or induce cell death. Resistance mechanisms can interfere with these results in a manner general to the anti-cancer drug effect or in a manner specific to a given mechanism. The mechanism by which resistance is conferred can be intracellular or extracellular, and categorized as intrinsic or adaptive. Intrinsic resistance (or primary resistance) refers to a previously untreated tumor that fails to respond to treatment. Acquired resistance is usually where adaptation during (or because of) treatment as well as cases where a selection of a resistant subset of cells occurs. Selection refers to a resistant subset within the heterogenous cell population expanding in number. Acquired resistance can manifest clinically as a recurrence of the cancer.

A common form of drug resistance involves alterations of signaling pathways. In one embodiment commonly altered signaling pathways include but are not limited to receptor tyrosine kinase, PI3K/Akt, Wnt, Ras/Raf, MEK/ERK, p38 MAPK, NF-κB/STAT3, markers of cancer stem cells, and epithelial-to-mesenchymal transition. In one embodiment, targeting altered signaling pathways can reverse drug resistance.

The expression of the receptor tyrosine kinase, AXL, can impact a wide array of drugs including chemotherapeutics which are unlikely to synergize with other gene knockdowns. In one embodiment, AXL knockdown can sensitize cells to cell cycle inhibitors, EGFR inhibitors, HDAC inhibitors, and PI3K/mTOR inhibitors.

In one embodiment, SLC7A11 knockdown increases sensitivity to numerous compounds, including cell cycle inhibitors and HDAC inhibitors. SLC7A11 has been associated with resistance to several drugs including Hsp90 inhibitors (Huang et al., 2005; Liu et al., 2007; Pham et al., 2010) and can serve as a prognostic marker for some cancers, especially gliomas (Takeuchi et al., 2013).

USP40 knockdown has similar patterns of synergy as the AXL knockdown. Functionally, the USP40 protein is an ubiquitin-specific protease (USP) likely involved in de-ubiquityling activity (Quesada et al., 2004). USP40 knockdown is reported as reducing glomerular organization with weaker cell junctions (Takagi et al., 2017). USP40 has not previously been reported as implicated in cancer, although other USP-family members have shown association with apoptosis (Vucic et al., 2011) and regulation of cell proliferation (Atanassov and Dent, 2011). In one embodiment, USP40 knockdown or inhibition can sensitize cells to cell cycle inhibitors, EGFR inhibitors, HDAC inhibitors, and PI3K/mTOR inhibitors.

SLFN13 is a gene in the Schlafen family which upon knockdown increased sensitivity in similar patterns to AXL and USP40. SLFN13 similarly influences compound sensitivity. In one embodiment, SLFN13 knockdown or inhibition can sensitize cancer cells to cell cycle inhibitors, EGFR inhibitors, HDAC inhibitors, and PI3K/mTOR inhibitors.

KLHL5 knockdown can increase sensitivity to Aurora kinase, cell cycle, and PI3K/Akt/mTOR axis inhibitors in a pattern distinct from other studied genes. KLHL5 showed low magnitude of differences in mean expression levels between cancer and normal tissue in the TCGA dataset (Table 3). However, the gene had some of the most significant survival differences comparing high and low expression. High expression of KLHL5 is associated with better overall survival in lung cancer (HR=0.67, p=1.6E-6) and breast cancer (HR=0.63, p=9.4E-9) but poorer survival in gastric cancer (HR=1.58, p=6.8E-5 (Table 2). KLHL5 is a largely unstudied member of the Kelch-like gene family. These genes are thought to share function in the ubiquitination process, but specific functionality and substrate binding for most family members still remain unknown (Dhanoa et al., 2013). In one embodiment, knockdown or inhibition can sensitize cancer cells to Aurora kinase, cell cycle, and PI3K/Akt/mTOR axis inhibitors.

Knockdown of S100A11 significantly decreased the viability of cancer cells and dramatically increased the activity of different classes of inhibitors. This gene encodes the S100 calcium binding protein A11 (calgizzarin) and functions in keratinocytes as a Ca++ and TGFβ signal transduction mediating growth signaling or suppression (Sakaguchi et al., 2008). S100A11 is overexpressed in cancer types including colorectal cancer (Niu et al., 2016; Wang et al., 2008) and prostate cancer (Rehman et al., 2004). Of the genes studied, S100A11 showed some of the largest and most significant expression differences or survival differences in the public patient data. In the TCGA dataset, S100A11 expression was increased two-fold in ten of nineteen cancer types and by more than four-fold in cervical (CESC), glioblastoma (GBM), and uterine (UCEC) cancers (Table 3). S100A11 functions in cell cycle regulation and promotes cellular survival by controlling p21 stability (Foertsch et al., 2013). High S100A11 expression has been noted as a marker for tumor aggressiveness and poor survival in many cancer types as it is involved in the initiation of TGFβ-mediated epithelial-mesenchymal transition which is associated with an aggressive phenotype (Niu et al., 2016). This aggressive phenotype promotes active growth and metastasis and a poorer prognosis in patients. Higher S100A11 expression is associated with poorer overall survival in lung (HR=1.35, p=2.83E-6), breast (HR=1.45, p=3.1E-11), and gastric (HR=1.85, 9.1E-13) cancers in the TCGA (Table 2). In one embodiment, S100A11 knockdown or inhibition can sensitize cancer cells to different classes of inhibitors.

S100A11, KLHL5, and AXL represent promising genes for this consideration because knockdown of any gene results in great reduction of cell viability and/or very strong synergies with many compounds in several classes of anti-cancer drugs that are FDA-approved or being evaluated in late stage clinical trials. A second-tier group of potential therapeutic targets includes at least five genes (SLC7A11, USP40, GALNT2, SLFN13, and EGFR), which decrease cell viability at various degrees and significantly synergize with numerous compounds.

B. Compositions that Alter Expression of Drug Resistance Genes

One embodiment provides compositions that inhibit or reduce the expression of drug resistance genes. These compositions can be any suitable drug compound, inhibitors, small molecules, siRNAs, or other composition suitable for inhibiting or reducing gene expression.

i. Synergistic Combinations

One embodiment provides synergistic combinations of compounds to treat cancer. As used herein, synergy implies a stronger than expected effect upon combination of two or more compounds. In one embodiment, genes that are synergistic with cancer drugs when inhibited or knocked down include but are not limited to S100A11, KLHL5, USP40, AXL, SLC7A11, and SLFN13.

In one embodiment, drug classes that are commonly synergized with the aforementioned gene knockdowns include inhibitors for the PI3K-AKT-mTOR pathway, the MEK-ERK pathway, the cell cycle regulators (CHK1, WEE1, CDK) and HDAC. Inhibitors for several growth factor receptors (EGFR, ERBB2, and FGFR) are also commonly synergized. The class IHDAC inhibitors and Raf inhibitors also show strong antagonism with multiple genes. The implications for cancer research and therapeutic development beyond the gene-drug relationships studied here are multiple. First, the drugs commonly synergized by the studied knockdowns represent drugs and drug classes favorable to synergistic combinations. Unpublished data on other gene and drug combinations suggest that this is indeed true. Second, the data gives new insights and understanding of molecular mechanism of killing or resistance for the drugs by suggesting that expression of genes heavily influences sensitivity to anticancer drugs. Third, the drugs lacking synergies or showing antagonistic relationships are less likely to be synergized in combination therapies. Chemotherapeutics were notably absent from synergistic relationships and some even were antagonistic upon combination. This may partially explain the limited success for combination therapy with chemotherapeutic agents and targeted therapies in clinical trials.

Data-mining strategies were successful at identifying novel drug resistance genes. While several genes studied were previously known drug resistance genes, many genes were previously unknown to be involved in drug sensitivity. This illustrates the power of using high-throughput drug screening for elucidating biological properties. Several of the genes from the panel are worth further mention and are candidates for further investigation on their impact on drug resistance. Genes that have previously been unreported or underappreciated for their effect on drug resistance include S100A11, USP40, SLFN13, and KLHL5. These genes along with AXL and SLC7A11 represent genes that may provide strong candidate therapeutic targets, especially for combination therapies. Synergistic combination therapy may be the best approach to achieve the desired efficacy and should be considered at the very beginning of drug development.

C. Inhibitors

In one embodiment, knockdown or inhibition of drug resistance genes in combination with common drug classes including but not limited to inhibitors for the PI3K-AKT-mTOR pathway, the MEK-ERK pathway, the cell cycle regulators (CHK1, WEE1, CDK) and HDAC can sensitize cancer cells to said drugs. Inhibitors for several growth factor receptors (EGFR, ERBB2, and FGFR) are also commonly synergized.

i. PI3K-AKT-mTOR Pathway Inhibitors

In some embodiments, drug resistance gene knockdown or inhibition is combined with a PI3K-AKT-mTOR pathway inhibitor. Suitable FDA approved inhibitors include but are not limited mTORC1 inhibitors temsirolimus and everolimus and the PI3Kδ inhibitor idelalisib. Other PI3K-AKT-mTOR pathway inhibitors which could be considered include but are not limited to ridaforolimus, nab-rapamycin, vistusertib, AZD8055, BEZ235, sapanisertib, CC-223. OSI-027, buparlisib, pictilisib, pilaralisib, PX-866, CH5132799, dactolisib, apitolisib, gedatolisib, duvelasib, everolimus, temsirolimus, PI-103, ZSTK474, GDC-0941, and AMG319 (Janku, F., et al, *Nat Rev Clin Oncol,* 15:273-291 (2018)).

ii. MEK/ERK Pathway Inhibitors

In some embodiments, drug resistance gene knockdown or inhibition is combined with a MEK/ERK pathway inhibitor. Suitable FDA approved MEK/ERK/RAF inhibitors include but are not limited to trametinib, cobimetinib, binimetinib, vemurafenib, and dabrafenib. Other MEK/ERK/RAF inhibitors which could be considered include but are not limited to selumetinib, doramapimod, PD-325901, CI-1040, PD035901, PH797804, SB203580, TAK 733, LGX818, TAK-632, MLN2480, MEK162, AZD6244, RO5126766, GDC-0623, SCH772984, and VTX11e (Samatar, A., and Poulikakos, P., *Nat Rev Drug Discov,* 13:928-942 (2014); Zhao, Y., and Adjei, A., *Nat Rev Clin Oncol,* 11:385-400 (2014)).

iii. Cell Cycle Regulators

In some embodiments, drug resistance gene knockdown or inhibition is combined with cell cycle inhibitors. Cell cycle inhibitors can target for example CHK1, WEE1, and CDK. Suitable cell cycle regulators include but are not limited to palbociclib, ribociclib, abemaciclib, flavopiridol, R-roscovitine, P276-00, SNS-032, dinaciclib, PD-0332991, LY-2835219, R547,MK-1775, AZD7762, LY2603618, PHA793887, ENMD-2076, PF-03814735 and LEE011 (Asghar, U., et al., *Nat Rev Drug Discov.,* 14:130-146 (2015); Bai, J., et al., *Cancer Biol Med,* 14:348-362 (2017)).

iv. HDAC Inhibitors

In some embodiments, drug resistance gene knockdown or inhibition is combined with HDAC inhibitors. Suitable HDAC inhibitors include but are not limited to romidepsin, belinostat, panobinostat, vorinostat, SAHA, givinostat, resminostat, abexinostat, quisinostat, rocilinostat, practinostat, entinostat, tacedinaline, mocestinostat, nicotinamide, sirtinol, cambinol, PCI-24781, AR-42, CUDC-101 (Eckschlager, T., et al., *Int J Mol Sci,* 18:1414 (2017)).

v. Growth Factor Receptor Inhibitors

In some embodiments, drug resistance gene knockdown or inhibition is combined with growth factor receptor inhibitors. Suitable EGFR inhibitors include but are not limited to gefitinib, erlotinib, lapatinib, cetuximab, neratinib, panitumumab, vandetanib, necitumumab, osimertinib dacomitinib, pelitinib, afatinib, and BMS599626. Suitable ERBB2 (HER2) inhibitors include but are not limited to trastuzumab, pertuzumab, lapatinib, neratinib, and ado-trastuzumab emtansine. Suitable FGFR inhibitors include but are not limited to erdafitinib, AZD4547, BGJ398, JNJ 42756493, PD173074, BAY1187982, MFGR1877S, and FP-1039 (Chae, Y. K., et al., *Oncotarget,* 8:16052-16074 (2017))

D. Therapeutic Regimen

Compositions and methods for treating cancer in a subject in need thereof are provided herein. One embodiment provides combination therapies including a compound that inhibits the PI3K-AKT-mTOR pathway, cell cycle, MEK-MAPK (ERK) pathway, or an HDAC inhibitor in combination with a compound that inhibits or reduces the expression of AXL, SLFN13, ANXA2, S100A11, KLHL5, SLC7A11, AVCVA, USP40 or a combination thereof.

In one embodiment the compound that inhibits or reduces the expression of a drug resistance gene is administered to the subject in need thereof before the inhibitor of PI3K-AKT-mTOR pathway, cell cycle, MEK-MAPK (ERK) pathway, or HDAC. The drug resistance gene inhibitor can be administered 1, 2, 3, 4, 5, 6, 7, 8, 9, 10, 11, 12, or more than 12 hours before the inhibitor of PI3K-AKT-mTOR pathway, cell cycle, MEK-MAPK (ERK) pathway, or an HDAC. In another embodiment, the drug resistance gene inhibitor is administered 1, 2, 3, 4, 5, 6, 7, or more than 7 days before the PI3K-AKT-mTOR pathway, cell cycle, MEK-MAPK (ERK) pathway, or HDAC. In one embodiment, the two inhibitors are administered simultaneously.

E. Pharmaceutical Compositions

Pharmaceutical compositions are provided. Pharmaceutical compositions containing the combinations of a gene inhibitor, and signal transduction inhibitor, a cancer therapeutic and combinations thereof. The compositions can be formulated for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed compositions as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed compositions, generally dosage levels of 0.001 to 20 mg/kg of body weight daily are administered to mammals. Generally, for intravenous injection or infusion, dosage may be lower.

In certain embodiments, the composition is administered locally, for example by injection directly into a site to be treated. Typically, the injection causes an increased localized concentration of the immunomodulatory agent composition which is greater than that which can be achieved by systemic administration. The immunomodulatory agent compositions can be combined with a matrix as described above to assist in creating an increased localized concentration of the polypeptide compositions by reducing the passive diffusion of the polypeptides out of the site to be treated.

The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more of the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

In embodiments the compositions are formulated for oral delivery. Oral solid dosage forms are described generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013, 556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) *J. Appl. Biochem.* 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

The disclosed compositions can be applied topically. Topical administration does not work well for most peptide formulations, although it can be effective especially if applied to the lungs, nasal, oral (sublingual, buccal), vaginal, or rectal mucosa.

The compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

The compositions disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Method of Use

The disclosed combination therapies can be used to enhance an immune response in a subject in need thereof. Exemplary methods are discussed in more detail below.
A. Immune Response Stimulation
1. Therapeutic Strategies Methods of inducing or enhancing an immune response in a subject are provided. Typically, the methods include administering a subject an effective amount of immunomodulatory agent, or cells primed ex vivo with the immunomodulatory agent. The immune response can be, for example, a primary immune response to an antigen or an increase effector cell function such as increasing antigen-specific proliferation of T cells, enhancing cytokine production by T cells, stimulating differentiation, or a combination thereof. In some embodiments, the agent can increase the development of naïve T cells into Th1, Th17, Th22, or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. In some embodiments, the agent can reduce or inhibit the activity of Tregs, reduce the production of cytokines such as IL-10 from Tregs, reduce the differentiation of Tregs, reduce the number of Tregs, reduce the ratio of Tregs within an immune cell population, or reduce the survival of Tregs. The immunomodulatory agent can be administered to a subject in need thereof in an effective amount to overcome T cell exhaustion and/or T cell anergy. Overcoming T cell exhaustion or T cell anergy can be determined by measuring T cell function using known techniques.

The methods can be used in vivo or ex vivo as immune response-stimulating therapeutic applications. Thus in some embodiments, the composition is administered directly to the subject. In some embodiments, the compositions is contacted with cells (e.g., immune cells) ex vivo, and the treat cells are administered to the subject (e.g. adoptive transfer). In general, the disclosed compositions can be used for treating a subject having or being predisposed to any disease or disorder to which the subject's immune system mounts an immune response. The agents can enable a more robust immune response to be possible. The disclosed compositions are useful to stimulate or enhance immune responses involving T cells.

2. Cancer

The disclosed compositions and methods can be used to treat cancer. Generally, the agents are used to stimulate or enhance an immune response to cancer in the subject by administering to the subject an amount of a composition that kills cancer cells in the patient.

Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS 1/4), ovarian carcinoma antigen (CA125), prostate specific antigen (PSA), carcinoembryonic antigen (CEA), CD19, CD20, HER2/neu, etc.).

The methods and compositions disclosed herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+ anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and cilliary body melanoma, and retinoblastoma; vaginal cancers, including, but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

B. Additional Therapeutics

1. PD-1 Antagonist

In some embodiments, compositions are co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U. S. A*, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods of this invention include antibodies that bind to PD-1 or ligands of PD-1, and other antibodies.

Suitable anti-PD-1 antibodies include, but are not limited to, those described in the following publications:
PCT/IL03/00425 (Hardy et al., WO/2003/099196)
PCT/JP2006/309606 (Korman et al., WO/2006/121168)
PCT/US2008/008925 (Li et al., WO/2009/014708)
PCT/JP03/08420 (Honjo et al., WO/2004/004771)
PCT/JP04/00549 (Honjo et al., WO/2004/072286)
PCT/IB2003/006304 (Collins et al., WO/2004/056875)
PCT/US2007/088851 (Ahmed et al., WO/2008/083174)
PCT/US2006/026046 (Korman et al., WO/2007/005874)
PCT/US2008/084923 (Terrett et al., WO/2009/073533)
Berger et al., *Clin. Cancer Res.*, 14:30443051 (2008).

A specific example of an anti-PD-1 antibody is an antibody described in Kosak, US 20070166281 (pub. 19 Jul. 2007) at par. 42), a human anti-PD-1 antibody, which in some embodiments is administered at a dose of 3 mg/kg.

Exemplary anti-B7-H1 antibodies include, but are not limited to, those described in the following publications:
PCT/US06/022423 (WO/2006/133396, pub. 14 Dec. 2006)
PCT/US07/088851 (WO/2008/083174, pub. 10 Jul. 2008)
US 2006/0110383 (pub. 25 May 2006)

A specific example of an anti-B7-H1 antibody is an antibody described (WO/2007/005874, published 11 Jan. 2007)), a human anti-B7-H1 antibody.

Additional anti-PD-1 and anti-B7-H1 antibodies are disclosed in 2014/0044738, which is specifically incorporated by reference herein in its entirety.

For anti-B7-DC antibodies see U.S. Pat. Nos. 7,411,051, 7,052,694, 7,390,888, and U.S. Published Application No. 2006/0099203.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., *Immunity*, Vol. 27, pp. 111-122, (2007)). Such fragments also include the soluble ECD portion of the PD-1 protein that includes mutations, such as the A99L mutation, that increases binding to the natural ligands (Molnar et al., *PNAS*, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

Other molecules useful in mediating the effects of T cells in an immune response are also contemplated as additional therapeutic agents. In some embodiments, the molecule is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., *Clinical Kidney Journal*, 3(2):135-137 (2010), published online December 2009.

In other embodiments, the antagonist is a small molecule. A series of small organic compounds have been shown to bind to the B7-1 ligand to prevent binding to CTLA4 (see Erbe et al., *J. Biol. Chem.*, 277:7363-7368 (2002). Such small organics could be administered alone or together with an anti-CTLA4 antibody to reduce inhibitory signal transduction of T cells.

2. Potentiating Agents

In some embodiments, additional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke *Crit Rev. Immunol.* 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al. *Cancer Immunol. Immunother.* 58:1219-1228 (2009). A similar result was observed in the HHD2 tumor model: adoptive transfer of CD4+CD25+ Treg after CTX pretreatment eliminated therapeutic response to vaccine (Taieb, J. *J. Immunol.* 176:2722-2729 (2006)).

Numerous human clinical trials have demonstrated that low dose CTX is a safe, well-tolerated, and effective agent for promoting anti-tumor immune responses (Bas, & Mastrangelo *Cancer Immunol. Immunother.* 47:1-12 (1998)).

The optimal dose for CTX to potentiate an anti-tumor immune response, is one that lowers overall T cell counts by lowering Treg levels below the normal range but is subtherapeutic (see Machiels et al. Cancer Res. 61:3689-3697 (2001)).

In human clinical trials where CTX has been used as an immunopotentiating agent, a dose of 300 mg/m$^2$ has usually been used. For an average male (6 ft, 170 pound (78 kg) with a body surface area of 1.98 m$^2$), 300 mg/m$^2$ is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. *Cancer Res.* 61:3689-3697 (2001), Hengst et al *Cancer Res.* 41:2163-2167 (1981), Hengst *Cancer Res.* 40:2135-2141 (1980)).

For larger mammals, such as a primate, such as a human, patient, such mg/m$^2$ doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22):6808-16.), anthracyclines, oxaliplatin, doxorubicin, TLR4 antagonists, and IL-18 antagonists.

IV. Methods of Identifying Drug Resistance Genes

One embodiment provides methods of identifying drug resistance genes. An exemplary method includes a genome-wide rankings strategy that leverages the NCI-60 dataset. In one embodiment, genes with large numbers of negative correlations to drugs are more likely to be candidate drug targets for cancer therapy or drug resistance genes. Pearson-correlations between gene expression and compound effect can be used for hypothesis building regarding relationships between drugs and genes. Rankings of genes can then be performed by calculating the number of compounds with Pearson correlation coefficients beyond −0.5 for negative correlation rankings. In one embodiment, the full correlation rankings (F-NCR) can use all sixty NCI-60 cell lines. In another embodiment, leukemia excluded correlation rankings (LE-NCR) use only fifty-four cell lines, and exclude cell lines derived from leukemia. In the preferred embodiment, LE-NCR methodology improves upon the full correlation rankings because leukemia cell lines are generally more sensitive to compounds and show distinct patterns of sensitivity.

In one embodiment, analysis of the top genes as identified using the LE-NCR methodology can be performed. Ingenuity pathway analysis can identify enriched networks, including key cancer signaling pathways. Pathways that can be included in pathway analysis include but are not limited to MEK, ER, Akt/PI3K, Hsp90, HDAC, PARP, NFkB, VEGF, and 26s Proteasome. In addition, enriched genes regulating molecular and cellular functions that can be identified include but are not limited to cell death and survival, cellular growth and proliferation, cell movement, cell-to-cell signaling and interaction, and cellular assembly and organization.

EXAMPLES

Materials and Methods
Experimental Model Details
Cell Culture

OVCAR-8, A549, SN12C, MEL-2, and SKOV-3 cell lines were obtained from the DTP, DCTC Tumor Repository. Their identities were confirmed with DNA fingerprinting. Cell lines were cultured in 1640-RPMI (Lonza) with 10% Fetal Bovine Serum (Sigma), and 1% Corning™ Cellgro™ Antibiotic-Antimycotic Solution (Thermo Fisher) with 100 IU Penicillin, 100 μg/ml of streptomycin, and 250 ng/ml of Amphotericin B at 37° C. with 5% $CO_2$. Experiments using 96-well plates utilized inner wells only with outer wells filled with PBS to minimize the effects of evaporation. Experiments using OVCAR-8 cells were performed within five passages from passage 6, which was obtained from DTP. Authentication of cell identity was performed using STR profiling and matched to known profiles in online databases. Cell lines tested negative for mycoplasma using Universal Mycoplasma Detection Kit (ATCC® 30-1012K™) (ATCC, Manassas, Virginia) following vendor protocols.

Method Details:
Cell Viability Assay

The Cell Counting Kit-8 (CCK-8) (Dojindo Molecular Technologies, Rockville, Maryland) was used to estimate cell viability. A mixture of 6 μl of 1640-RPMI and 3 μl CCK-8 was added to each well five hours prior to measuring OD values at 450 nm using a multifunctional microplate reader (Bio-Tek). Cell-free negative control was set to 0% and the same-plate average positive control growth reading (n=3) was set to 100%. The positive controls were sham treated with reagents relevant to each experiment (comparable DMSO concentration in experiments where drug testing was performed and/or equivalent knockdown reagents and protocols in the experiments using siRNA and shRNA.)

Gene Knockdown

Sequences for siRNA and Taqman probes for qRT-PCR as well as product numbers for shRNA lentivirus are listed in Supplementary Table S3. Gene knockdown using siRNA (Thermo Fisher) or shRNA (Santa Cruz) was performed using the manufacturer's instructions. siRNA was introduced into the cells using Lipofectamine® 2000 (Thermo Fisher). Serum-free, antibiotic-free 1640-RPMI media was utilized during knockdown. 30 μL of Lipofectamine in 970 μL media and 60 μL of 20 μM siRNA in 940 μL media were incubated separately for five minutes, then combined and incubated for 20 minutes. This mixture was added to 8 mL of media containing 2.5×10$^5$ cells/ml and plated in a 100 mm plate yielding a final siRNA concentration of 1.2 nM. After 16 hours incubation, cells were resuspended and transferred to 96-well plates at a concentration of 4000 cells per well in 100 μL of antibiotic-free, 10% FBS 1640-RPMI. Inner wells of the plate were used for experimentation and outer wells were filled with water. In combination studies, drugs were added six hours after plating into 96-well format.

Knockdown efficiency was tested for each experiment at plating to drug plates and seventy-two hours after drug addition. qRT-PCR was used to confirm knockdown efficiency at each time-point. Gene expression levels determined by using normalization of expression to the geometric mean of three reference genes (ESD, MRPL19, and IPO8) selected for their stability in expression (Wu, et al., *Am J Transl Res*, 8:5729-5740 (2016)).

Gene knockdown using shRNA lentiviral particle transduction: cells were plated in 100 μL of 1640-RPMI (antibiotic-free) in 96-well plate at $5 \times 10^4$/mL and incubated 12h. Cells were cultured in media containing 1 μL of lentiviral particles and 5 μg/mL polybrene for 24h prior to maintenance in antibiotic-free 1640-RPMI. Cell viability and knockdown efficacy were assessed 72h after exposure to the lentivirus. To establish and maintain stable cell lines, knockdown cells were selected by 2 μg/mL puromycin beginning 5 days after knockdown exposure with media replacement or expansion as necessary every 2-3 days. Knockdown was tested after seventy-two hours.

Drug Activity Assays

A library of 346 anticancer compounds that are FDA-approved for clinical use or for clinical trials was screened at a concentration of 100 nM (Selleckchem, Houston, Texas) The full list of compounds tested with mechanism classes are in Table 2. Comparisons of drug effect were performed using data generated on the same day. A minimum of two replicates was performed with drug library screening and a minimum of three replicates was done for all other tests.

Quantification and Statistical Analysis

Gene Selection

Genes with larger propensities for altered expression or altered survival in patient samples were selected. The data used for determining this was obtained from TCGA, Oncomine, and km-plot. Gene expression data from the TCGA gene expression comparing cancer to normal control utilizing RNAseq data (IlluminaHiSeq: log 2-normalized_count+1) was downloaded from Xena browser. Gene expression differences for the eighteen selected genes are shown in Table S1. Cancer versus adjacent normal data from Oncomine™ (Rhodes, D R, et al., *Neoplasia*, 9:166-180 (2007)) was used for exclusion of genes with few expression changes. The thresholds of P-Value (1E-4), Fold Change (2), Gene Rank (Top 10%), across all data were used, and any genes with expression changes in fewer than 4 studies were excluded. The Oncomine™ analysis for the selected genes is shown in Table 1. Kaplan-Meier meta-analysis of plots of patient data from clinical studies performed using the default settings of the 2017 edition of (Szasz, A. M., *Oncotarget*, (2016)). The observed Hazard Ratios (HR) of the four cancer types (Breast, Ovarian, Gastric, Lung) for the selected genes are shown in Table 1. Only genes that had clinical characteristics and had a large number of correlated compounds using leukemia excluded NCI-60 correlations were selected. NCI-60 correlations were performed using 54 cell lines (all except six leukemia cell lines) using drug effect and gene data obtained from CellMiner™. Pearson correlations were calculated between all genes and all compounds in the NCI-60 dataset using R software. Two correlations were performed between the gene expression z-score and the drug $GI_{50}$ z-score. Genes were ranked based on the sum of negatively correlated compounds with correlation R<−0.500.

Statistical Analyses

Statistical analyses were performed using the R language and environment for statistical computing (R version 3.3.1; R Foundation for Statistical Computing) and Microsoft Excel. Student's T-test (two-tailed, unpaired) was used to calculate p-values for confirmation of drug effect. $GI_{50}$ values were calculated using a four-parameter logistic function to obtain a classical "s" curve for drug titrations using SigmaPlot (Systat Software, San Jose, CA). Heatmaps were created using the R package "pheatmap". Clustering was done with WPGMA hierarchical clustering. QIAGEN's Ingenuity Pathway Analysis (IPA®, QIAGEN Redwood City) was utilized for assessment of network and pathway contributions of top genes identified using the NCI-60 correlations.

Classification of siRNA-Drug Interactions

Figure 6B:
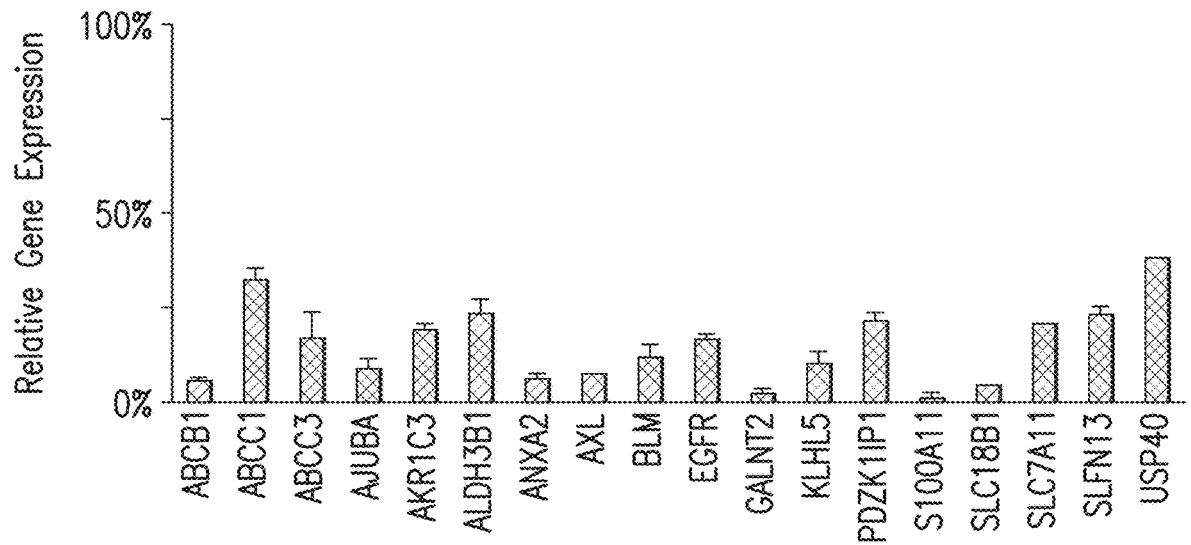
FIG. 6B shows knockdown efficiency by siRNA for each of the 19 selected genes. Gene expression in sham-treated OVCAR-8 cells was set to 100% and expression in siRNA treated cells were compared to controls. Data shown are for the time point after the initial 16 hours of exposure to siRNA. Similar knockdown effects were observed at 72 hours of growth after the initial 16-hour exposure. Data represents the mean±s. d. from the 3 replicate cultures.

Values were calculated for same-plate sham control (set to 100%), no cells (set to 0%), $V_A$ (drug only), $V_B$ (knockdown only), $V_A \times V_B$ (expected combinatorial result), and $V_{AB}$ (actual Combinatorial result). Combinatorial effects were classified using two measures of combinatorial action: 1) the coefficient of drug interaction (CDI), defined as ($V_{AB}/(V_A \times V_B)$) and 2) the distance in standard deviation (SD) of $V_{AB}-(V_A \times V_B)$. The standard deviation was determined by performing a regression on the experimental standard deviations as observed for all combination tests and the value used for calculation was based on the 99% confidence interval of the regression line (FIG. 6A). Based on the variance observed, the formula used for calculating standard deviation was: $SD=(V_{AB}-V_A \times V_B)/(0.0401V_{AB}+0.0105)$. Categorization of combinatorial data used thresholds set at SD±2.55 indicating a 99% 683 confidence interval for categorizing Synergy or Antagonism/Additive. The categories "Highly 684 Synergistic" and "Highly Antagonistic" used an SD threshold of SD±5.1. In confirmation studies significance was determined using a Student's T-test (two-tailed, unpaired) with p<0.05 indicating significance.

Example 1. Genes that Impact Drug Sensitivity and Resistance

Results:

This study explicitly demonstrates that expression of the receptor tyrosine kinase, AXL, impacts a wide array of drugs including chemotherapeutics which are unlikely to synergize with other gene knockdowns. AXL knockdown most profoundly sensitized cells to cell cycle inhibitors, EGFR inhibitors, HDAC inhibitors, and PI3K/mTOR inhibitors. The impact of AXL on drug sensitivity of targeted and chemotherapeutic compounds was previously established, although in a limited scope, in both patient studies and laboratory models (Hong, C. C., *Cancer Letters*, 268:314-324 (2008), Hong, J, et al., *Cancer Research*, 73:331-340 (2013), Byers, L. A., et al., *Clin Canc Res*, 19:279-290 (2013)); however, this study clearly demonstrates the scope of anticancer compounds on which the gene has an effect. Pharmacologic inhibition of AXL has shown potential in clinical studies demonstrating effective reversal or overcoming of drug resistance (Rho, J. K., et al., *Canc Res*, 74:253-262 (2014)).

S100A11 encodes the S100 calcium binding protein A11 (calgizzarin) and mediates growth signaling or suppression (Sakaguchi, M., et al., *Mol Biol Cell*, 19:78-85 (2008)), cell cycle regulation, and cellular survival by controlling p21 stability (Foertsch, F., et al., *The FEBS Journal*, 280:3840-3853 (2013)). S100A11 is overexpressed in cancers including colorectal (Niu, Y, et al., *Sci Rep*, 6:26112 (2016); Wang, G., et al., *Int J Colorectal Dis*, 23:675-682 (2008)) and prostate (Rehman, I., et al., *Human Pathology*, 35:1385-1391 (2004)) and is a marker of tumor aggressiveness and poor survival. S100A11 was one of the most interesting genes from the public patient data in terms of expression differences or survival differences. S100A11 expression was increased two-fold in ten of nineteen TCGA cancers and more than four-fold in cervical (CESC), glioblastoma (GBM), and uterine (UCEC) cancers. Higher S100A11 expression is also associated with poorer overall survival in lung (HR=1.35, p=2.83E-6), breast (HR=1.45, p=3.1E-11), and gastric (HR=1.85, 9.1E-13) cancers (Table 1).

KLHL5 knockdown increased sensitivity to Aurora kinase, cell cycle, and PI3K/Akt/mTOR axis inhibitors. Despite low magnitude of differences in mean expression levels between cancer and normal tissue in the TCGA dataset, the gene had some of the most significant survival differences comparing high and low expression. High expression of KLHL5 is associated with better overall survival in lung cancer (HR=0.67, p=1.6E-6) and breast cancer (HR=0.63, p=9.4E-9) but poorer survival in gastric cancer (HR=1.58, p=6.8E-5 (Table 1). KLHL5 is a largely unstudied member of the Kelch-like gene family. These genes are thought to function in the ubiquitination process, but specific function or substrate binding remain unknown for most family members (Dhanoa, B. S., et al., *Hum Gen*, 7:13 (2013)). USP40, SLFN13, and SLC7A11 strongly synergized with numerous compounds. USP40 has not previously been reported as implicated in cancer. The gene is involved in de-ubiquityling activity (Quesada, V., et al., *Biochem and Biophy Res Comm*, 314:54-62 (2004)) and cell junction strength in glomeruli (Takagi, H., et al., *Am J Physiol Renal Physiol*, 312:F702-F715 (2017)). SLFN13 is a Schlafen family gene that our study indicates has drug sensitivity effects much like family member SLFN11 which influences sensitivity of numerous chemotherapeutic agents (Zoppoli, G., et al., *Proceedings of the National Academy of Sciences of the United States of America*, 109:15030-15035 (2012)), and predicts patient survival after treatment with those drugs (Deng, Y., et al., *BMC Cancer*, 15:833 (2015)). SLC7A11 has been associated with resistance to several drugs including Hsp90 inhibitors and can serve as a prognostic marker for some cancers, especially gliomas (Takeuchi, S., et al., *Neurosurgery*, 72:33-41 (2013)). The impact of SLC7A11 on drug sensitivity of numerous compounds was confirmed, including cell cycle inhibitors and HDAC inhibitors.

Example 2. Identification of Candidate Genes Via Gene-Drug Correlations

Figure 1B:
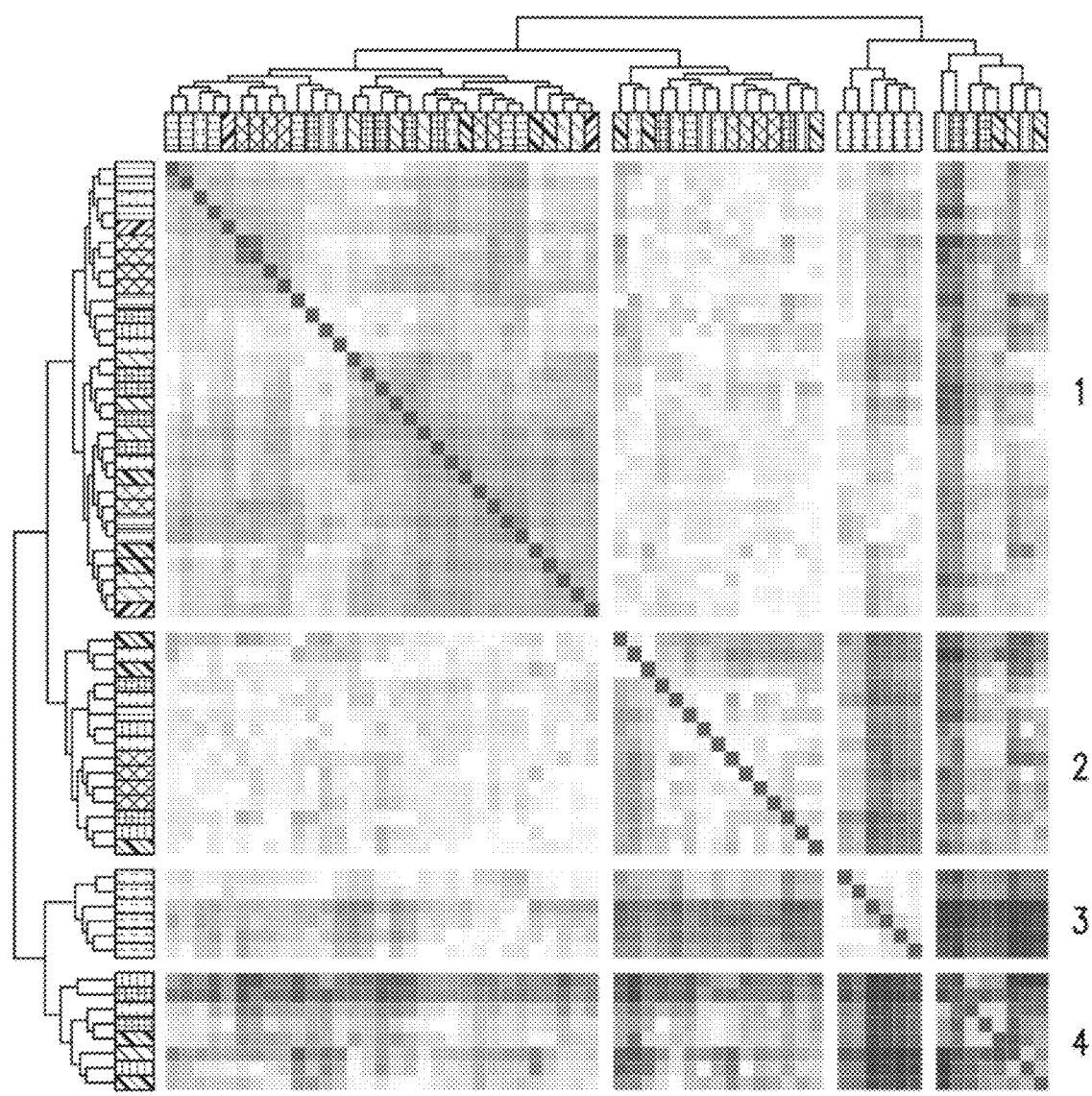
FIGS. 1B-1D shows a clustering of NCI-60 cell lines based on the pairwise correlations calculated using $GI_{50}$ of 20,000 compounds against each cell line.

Results:

A ranking system centered on the number of compounds that show negative correlations to each gene within the NCI-60 dataset was developed. The rankings utilized correlation values calculated using the fifty-four solid tumor cell lines after excluding the leukemia cell lines in contrast to previous studies that used the full dataset. Leukemia represents a different disease with different cellular properties and molecular characteristics from the solid tumor CCLs. The myeloid lineage and suspended culture for leukemia versus the epithelial origin and adherent nature of solid cancers are some examples of their distinctions that scale from the visible to the molecular level. Leukemia respond differently to therapeutics than the other NCI-60 CCLs as illustrated by patterns of the $GI_{50}$ values of the 20,000+ compounds titration screened across all NCI-60 CCLs. First, leukemia is typically more sensitive to compounds with an average median $GI_{50}$ of 6 μM versus 15 μM in solid tumors (FIG. 1A). Second, leukemia CCLs are clustered together by the pairwise correlations of the $GI_{50}$ values between cell lines, indicating a similar response to most drugs (FIG. 1B). These differences lead to the conclusion that leukemia cell lines are generally more sensitive to compounds compared to the remaining set of cell lines. Due to the uniqueness of leukemias, gene-drug correlations calculated with leukemias may not be indicative of the true relationships between genes and compounds.

While the previous rankings were based the strength of the correlations, our approach ranks genes using the number of compounds correlated with the gene beyond a threshold. The threshold for Pearson correlation coefficients (R) was set at −0.5 to determine the number of correlated compounds for every gene. Genes are ranked by the number of compounds with R<0.5, with the assumption that more correlated compounds indicate higher likelihood as drug resistance genes.

Figure 1C:
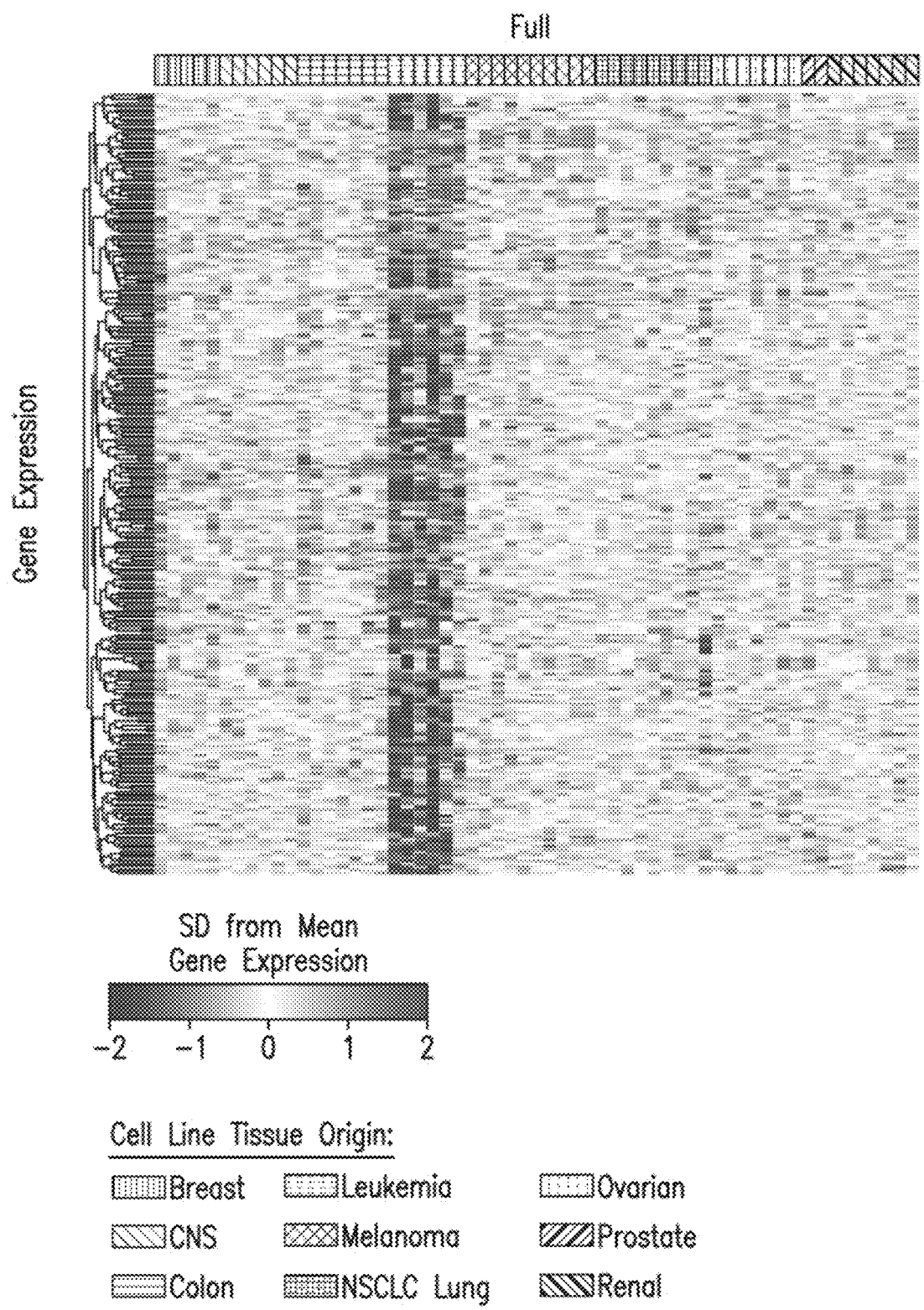
Figure 1D:
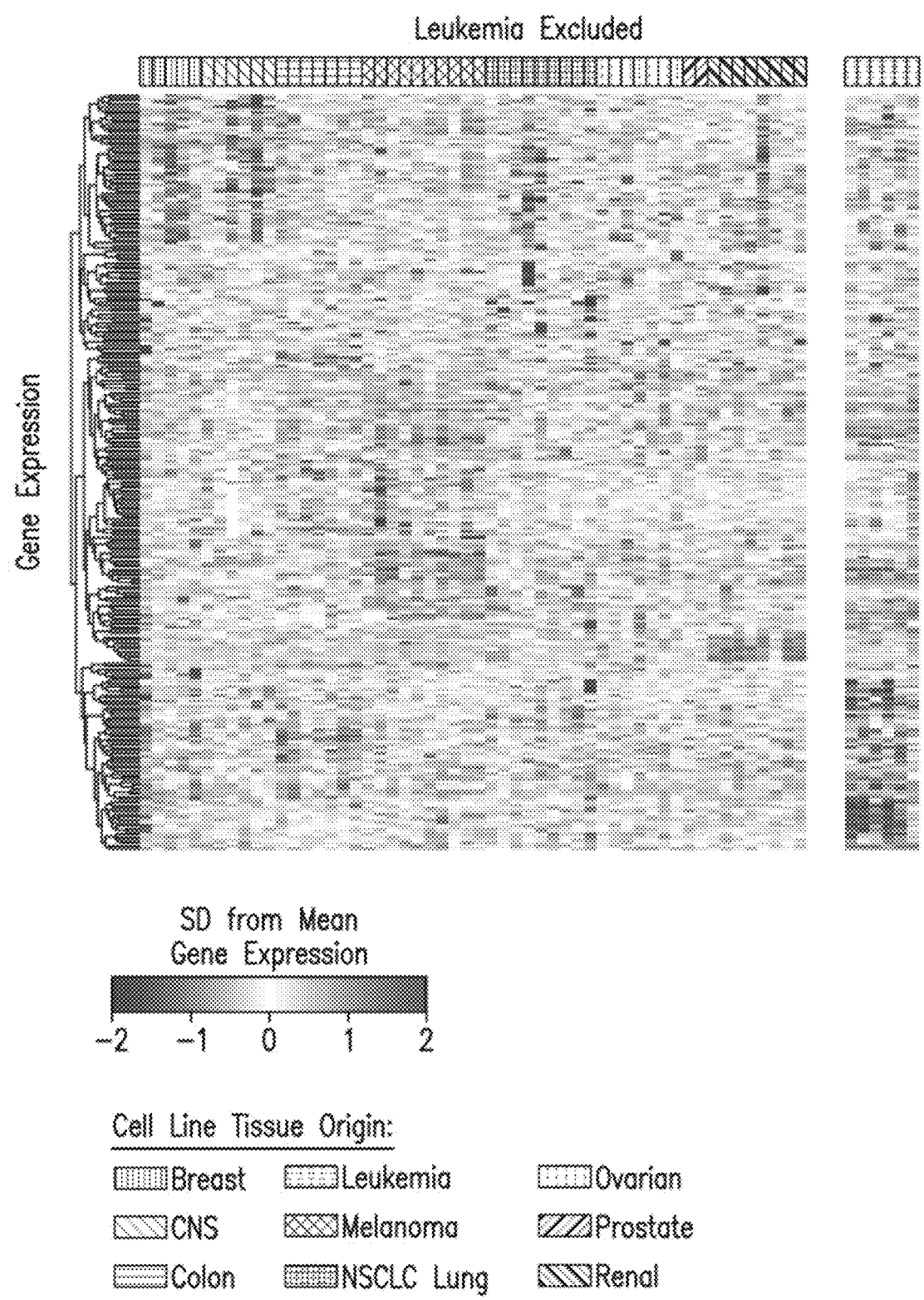
Figure 1E:
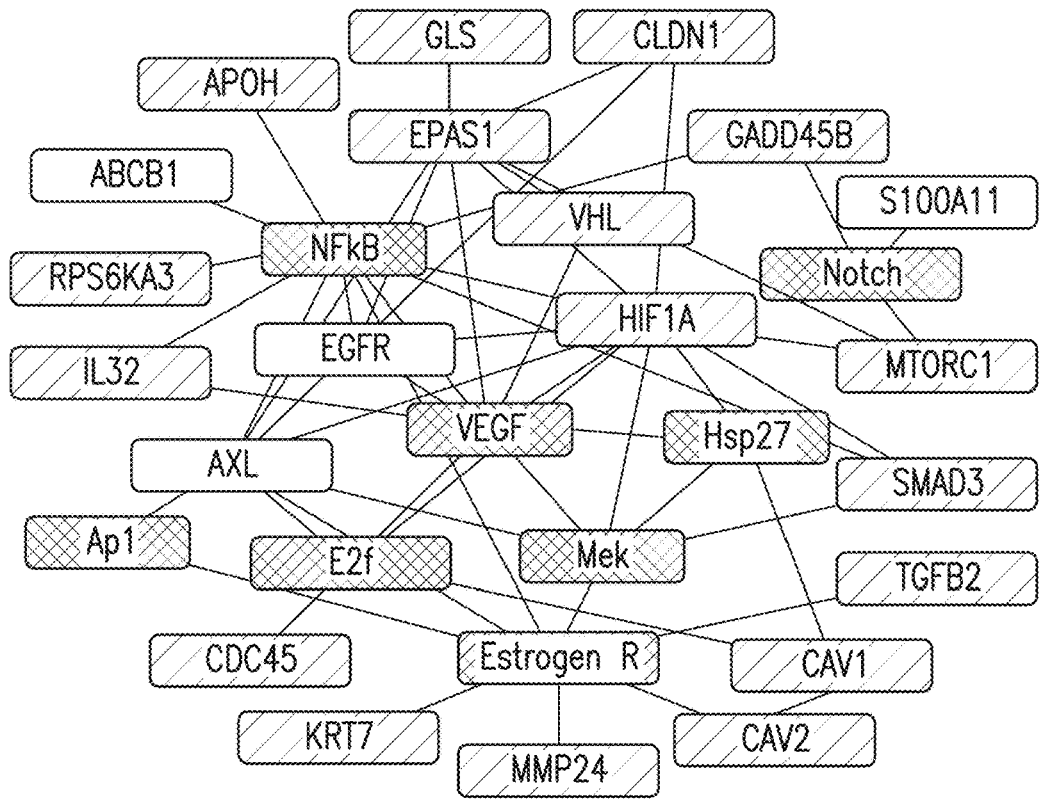
FIGS. 1E-1G show the top three enriched networks from Ingenuity Pathway Analysis (IPA) using the top 260 ranking genes (FIG. 1D shows leukemia excluded). Genes selected for this study are depicted in white while other high-ranking genes are depicted in gray. Closely associated genes or pathways identified by IPA are depicted in black and include genes or pathways frequently targeted by anti-cancer treatment strategies.
Figure 1F:
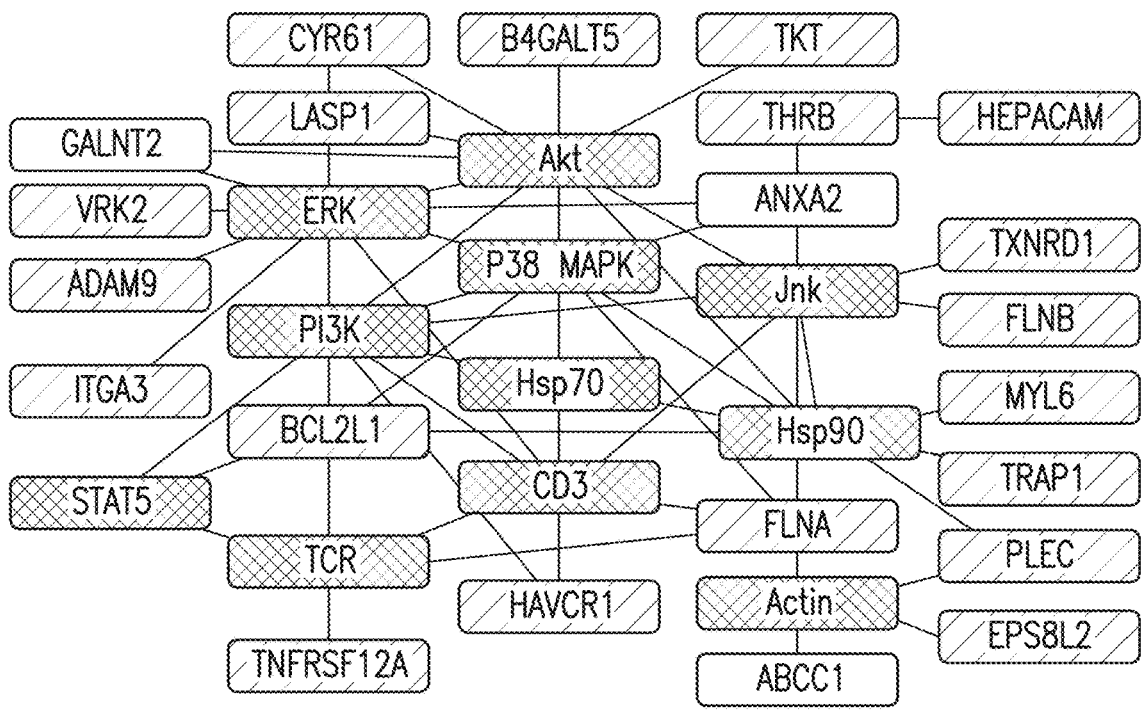
Figure 1G:
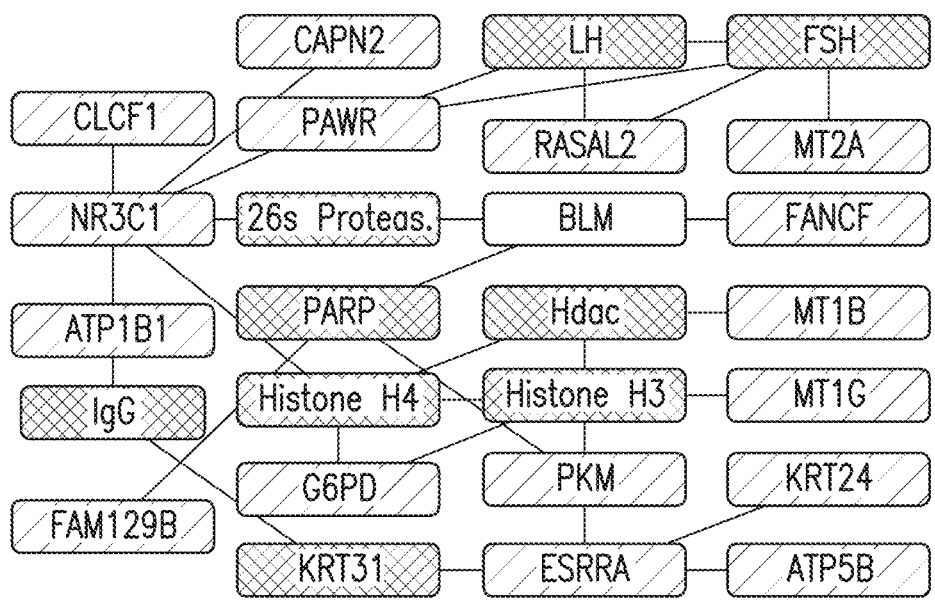

The top 1% (260) genes were further analyzed for their biological and molecular functions. The Ingenuity Pathway Analysis identified the top three enriched networks as key cancer signaling pathways which are currently targeted by therapeutics: MEK, ER, Akt/PI3K, Hsp90, HDAC, PARP, NFkB, VEGF, and 26s Proteasome (FIG. 1C). Molecular and cellular functions enriched among the top genes were highlighted by cell death and survival (67 genes, p116=6.37E-9), cellular growth and proliferation (67 genes, p=7.46E-7), cell movement (40 genes, p=7.61E-6), cell-to-cell signaling and interaction (20 genes, p=9.98E-6), and cellular assembly and organization (28 genes, p=9.98E-6). These results indicate that the top-ranking genes are, or interact with, known anticancer drug targets and thus have a higher likelihood to be implicated in cancer.

The top 260 genes were also examined for other clinical evidence in cancer patients including increased expression in cancers, degree of expression differences, differential patient survival based on expression levels. The drug-gene ranking and clinical evidence, eighteen genes were selected for subsequent confirmation studies (Table 1). Several well-known drug resistance genes (ABCB1, ABCC1, ABCC3, AXL, and EGFR) were included as positive controls, some have limited evidence to be involved in drug sensitivity (AKR1C3 and SLC7A11), while others have scant literature knowledge but may represent yet unidentified drug resistance genes.

TABLE 1

Gene expression data for 18 candidate genes in public domain.

| Gene | Entrez Gene ID | Oncomine Inc. | Oncomine Dec. | BLCA | BRCA | CESC | COAD | GBM | HNSC | KICH | KIRC | KIRP | LIHC |
|---|---|---|---|---|---|---|---|---|---|---|---|---|---|
| ABCB1 | 5243 | 2 | 40 | −2.3 | −2.7 | −4.3 | −2.4 | −0.7 | −1.2 | −6.4 | −2.4 | −0.3 | −0.9 |
| ABCC1 | 4363 | 23 | 3 | −0.2 | 0.2 | 0.9 | 1.1 | 0.3 | 0.7 | 0.1 | 0.7 | 0.5 | 0.7 |
| ABCC3 | 8714 | 28 | 6 | 1.1 | −0.3 | 1.8 | −1.0 | 5.3 | 0.1 | −3.3 | 2.4 | 2.0 | −0.2 |
| AJUBA | 84962 | 30 | 7 | 1.0 | −0.4 | 1.3 | 3.1 | 3.1 | 1.0 | −2.9 | −0.3 | −0.3 | 0.1 |
| AKR1C3 | 8644 | 11 | 36 | −0.4 | −2.7 | −0.6 | −1.5 | −0.3 | 0.3 | −4.4 | 0.6 | 0.5 | 1.4 |
| ALDH3B1 | 221 | 13 | 19 | −0.6 | 0.3 | −0.2 | 0.2 | 1.4 | −1.2 | −2.2 | 1.0 | 1.1 | 0.3 |
| ANXA2 | 302 | 45 | 11 | 0.4 | −0.2 | 1.4 | 0.2 | 3.4 | 0.0 | −0.5 | 0.8 | 1.6 | 1.2 |
| AXL | 558 | 13 | 23 | −1.8 | −0.8 | −2.1 | −1.4 | 0.3 | 0.6 | −1.0 | 1.6 | 1.0 | −1.5 |
| BLM | 641 | 22 | 2 | 2.5 | 1.8 | 5.3 | 1.3 | 2.1 | 1.1 | 0.5 | 1.5 | 1.3 | 2.5 |
| EGFR | 1956 | 27 | 38 | −0.1 | −3.3 | 1.2 | −0.8 | 4.0 | 0.4 | −0.1 | 1.1 | −0.3 | −0.9 |
| GALNT2 | 2590 | 14 | 3 | 0.6 | 0.4 | 0.5 | 0.3 | 1.0 | 1.0 | −0.4 | 0.6 | 0.0 | −0.2 |
| KLHL5 | 51088 | 12 | 6 | −1.2 | −0.5 | −0.2 | −0.5 | 0.6 | 1.1 | −0.7 | −0.2 | −1.0 | 0.3 |
| PDZK1IP1 | 10158 | 22 | 11 | 2.4 | −0.2 | 4.1 | 0.7 | 1.7 | −0.9 | −6.9 | 0.3 | 0.3 | 1.5 |
| S100A11 | 6282 | 54 | 15 | 1.4 | 1.0 | 2.7 | 1.8 | 3.1 | 0.0 | −0.2 | 0.6 | 1.8 | 0.5 |
| SLC18B1 | 116843 | 4 | 2 | −0.3 | −0.9 | 0.3 | −0.2 | 0.1 | −0.9 | −0.4 | −0.9 | −0.4 | 0.4 |
| SLC7A11 | 23657 | 29 | 3 | −0.3 | 1.5 | 3.5 | 2.7 | −0.7 | 1.1 | 3.1 | 1.9 | 2.1 | 3.5 |
| SLFN13 | 146857 | 5 | 3 | 0.9 | −1.3 | 3.1 | −1.3 | 2.0 | −0.1 | 0.2 | 2.1 | 2.6 | −0.4 |
| USP40 | 55230 | 2 | 2 | 0.1 | −0.2 | 0.0 | 0.4 | 0.6 | 0.1 | −0.5 | −0.1 | 0.4 | 0.2 |

| Gene | Entrez Gene ID | LUAD | LUSC | PAAD | PRAD | READ | SARC | SKCM | THCA | UCEC | Breast HR | Breast pval |
|---|---|---|---|---|---|---|---|---|---|---|---|---|
| ABCB1 | 5243 | −1.7 | −2.9 | −0.8 | 1−0.2 | −1.5 | −2.4 | −2.9 | −0.2 | −3.5 | 0.58 | 1.0E-16 |
| ABCC1 | 4363 | 0.1 | 1.5 | −0.1 | 0.3 | 1.1 | 0.4 | 0.0 | −0.5 | 1.0 | 1.06 | 2.7E-01 |
| ABCC3 | 8714 | 2.2 | −0.5 | 0.7 | −1.2 | −0.3 | 0.0 | −3.2 | 2.5 | 1.6 | 0.97 | 6.0E-01 |
| AJUBA | 84962 | −0.6 | 0.5 | 0.5 | −1.4 | 2.7 | −0.9 | 1.1 | 0.2 | −0.2 | 0.94 | 4.2E-01 |
| AKR1C3 | 8644 | 0.2 | 1.5 | 1.1 | −0.3 | −0.4 | −1.8 | 0.2 | −0.8 | −0.5 | 0.96 | 9.6E-01 |
| ALDH3B1 | 221 | −1.3 | −3.9 | 1.0 | −0.9 | 0.2 | −0.8 | 0.0 | 2.3 | 0.0 | 1.02 | 7.6E-01 |
| ANXA2 | 302 | −0.5 | −0.1 | 0.8 | −1.2 | 0.1 | 0.6 | 0.6 | 0.6 | 0.8 | 1.09 | 1.3E-01 |
| AXL | 558 | −1.2 | −1.7 | −0.1 | −0.8 | −1.7 | 0.8 | −1.2 | 0.3 | −2.3 | 0.82 | 3.9E-04 |
| BLM | 641 | 2.2 | 3.0 | 0.2 | 0.8 | 1.2 | 3.5 | −0.4 | 0.3 | 3.1 | 1.02 | 7.6E-01 |
| EGFR | 1956 | −0.2 | 0.8 | 0.9 | −0.9 | −0.6 | 0.3 | 0.9 | 0.0 | −1.2 | 0.87 | 7.4E-02 |
| GALNT2 | 2590 | 0.7 | 0.8 | 0.3 | 0.0 | 0.3 | 0.6 | 1.3 | 0.2 | 0.4 | 0.84 | 2.3E-03 |
| KLHL5 | 51088 | 0.4 | 0.6 | −0.7 | −0.9 | −1.5 | −0.4 | −1.1 | 0.0 | −0.8 | 0.63 | 9.4E-09 |
| PDZK1IP1 | 10158 | 0.3 | −1.3 | 1.5 | 0.0 | 0.8 | −6.4 | 2.8 | 3.5 | 1.8 | 0.92 | 1.4E-01 |
| S100A11 | 6282 | 0.5 | 1.1 | 0.7 | −0.2 | 1.7 | 0.7 | 0.2 | 1.5 | 2.0 | 1.45 | 3.1E-11 |
| SLC18B1 | 116843 | 0.3 | 0.3 | −0.5 | −0.3 | −0.5 | −0.2 | 1.1 | −0.7 | 0.5 | 0.87 | 6.9E-02 |
| SLC7A11 | 23657 | 2.3 | 3.0 | 2.4 | 1.6 | 1.9 | 2.4 | 1.8 | −0.1 | 2.2 | 1.01 | 8.9E-01 |
| SLFN13 | 146857 | 1.6 | 0.0 | 0.2 | −1.2 | −1.5 | 1.9 | −1.6 | 0.6 | −0.4 | 0.92 | 2.8E-01 |
| USP40 | 55230 | 0.2 | −0.4 | −0.1 | 0.2 | 0.6 | −0.6 | 0.2 | −0.4 | 0.2 | 0.6 | 1.689.8E-06 |

| Gene | Entrez Gene ID | Ovarian HR | Ovarian pval | Lung HR | Lung pval | Gastric HR | Gastric pval |
|---|---|---|---|---|---|---|---|
| ABCB1 | 5243 | 0.99 | 8.2E-01 | 0.96 | 5.7E-01 | 1.4 | 2.1E-04 |
| ABCC1 | 4363 | 1.08 | 2.5E-01 | 0.91 | 1.7E-01 | 1.36 | 4.4E-04 |
| ABCC3 | 8714 | 1.08 | 5.4E-01 | 0.73 | 1.2E-06 | 1.49 | 1.1E-05 |
| AJUBA | 84962 | 1.24 | 2.4E-02 | 0.88 | 1.2E-01 | 0.65 | 2.1E-04 |
| AKR1C3 | 8644 | 0.91 | 1.6E-01 | 1.09 | 1.7E-01 | 0.83 | 5.2E-02 |
| ALDH3B1 | 221 | 0.96 | 5.1E-01 | 0.85 | 1.3E-02 | 1.28 | 4.2E-03 |
| ANXA2 | 302 | 0.95 | 4.4E-01 | 1.56 | 4.5E-12 | 1.43 | 1.4E-04 |
| AXL | 558 | 1.36 | 2.0E-06 | 0.71 | 7.6E-08 | 1.42 | 4.9E-05 |
| BLM | 641 | 0.89 | 7.1E-02 | 1.49 | 5.1E-10 | 1.22 | 4.0E-02 |
| EGFR | 1956 | 1.04 | 7.0E-01 | 0.82 | 2.3E-02 | 1.35 | 9.2E-03 |
| GALNT2 | 2590 | 1.04 | 5.3E-01 | 0.74 | 3.8E-06 | 1.7 | 9.3E-10 |
| KLHL5 | 51088 | 0.95 | 5.9E-01 | 0.67 | 1.6E-06 | 1.58 | 6.8E-05 |
| PDZK1IP1 | 10158 | 0.88 | 4.4E-02 | 0.93 | 2.5E-01 | 0.73 | 3.9E-04 |
| S100A11 | 6282 | 0.97 | 6.7E-01 | 1.35 | 2.8E-06 | 1.85 | 9.1E-13 |
| SLC18B1 | 116843 | 0.93 | 4.4E-01 | 0.8 | 9.0E-03 | 0.54 | 2.5E-08 |

TABLE 1-continued

Gene expression data for 18 candidate genes in public domain.

| | | | | | | | |
|---|---|---|---|---|---|---|---|
| SLC7A11 | 23657 | 0.98 | 7.5E−01 | 1.15 | 2.6E-02 | 0.73 | 2.4E-04 |
| SLFN13 | 146857 | 1.01 | 9.5E−01 | 0.87 | 1.0E−01 | 1.68 | 9.8E-06 |
| USP40 | 55230 | 0.97 | 7.6E−01 | 0.66 | 7.4E-07 | 1.59 | 4.6E-05 |

*Italicized font* => 10 oncomine studies where cancer expression significantly higher than surrounding normal
Doubleunderlinedfont => 10 oncomine studies where cancer expression significantly lower than surrounding normal
Underlined font = TCGA cancer type where cancer expression significantly higher than surrounding normal or normal control
Bold font = TCGA cancer type where cancer expression significantly lower than surrounding normal or normal control
Hatched underlined font = Hatched underlined font = survival significantly poorer in patients with high expression of gene
Wavy underlined font = survival significantly poorer in patients with low expression of gene Table 1 shows gene expression data for the 18 candidate genes in public domains. The left section presents the number of studies with significant gene expression changes in the Oncomine™ meta-analysis of gene expression changes in Cancer vs. Normal across numerous studies for 20+ cancer types. The thresholds used for a call for significance are p-value <1E-4, fold change >2 and gene rank (Top 10%) across all data. The center section depicts the fold change across the TCGA gene expression dataset across cancer types (cancer/control) as determined by RNAseq. Significant differences in gene expression (p<0.01) are shaded. The right section indicates hazard ratios (HR) and associated p values in progression free survival analyses for subgroups defined by gene expression. Data were extracted from the 2017 edition and the default settings in. NCI-60 Data indicates the number of negatively correlated compounds (R<−0.500) with each gene using leukemia excluded correlations.

Example 3. Identified Genes Decrease Cancer Cell Viability and/or Proliferation

Figure 2A:
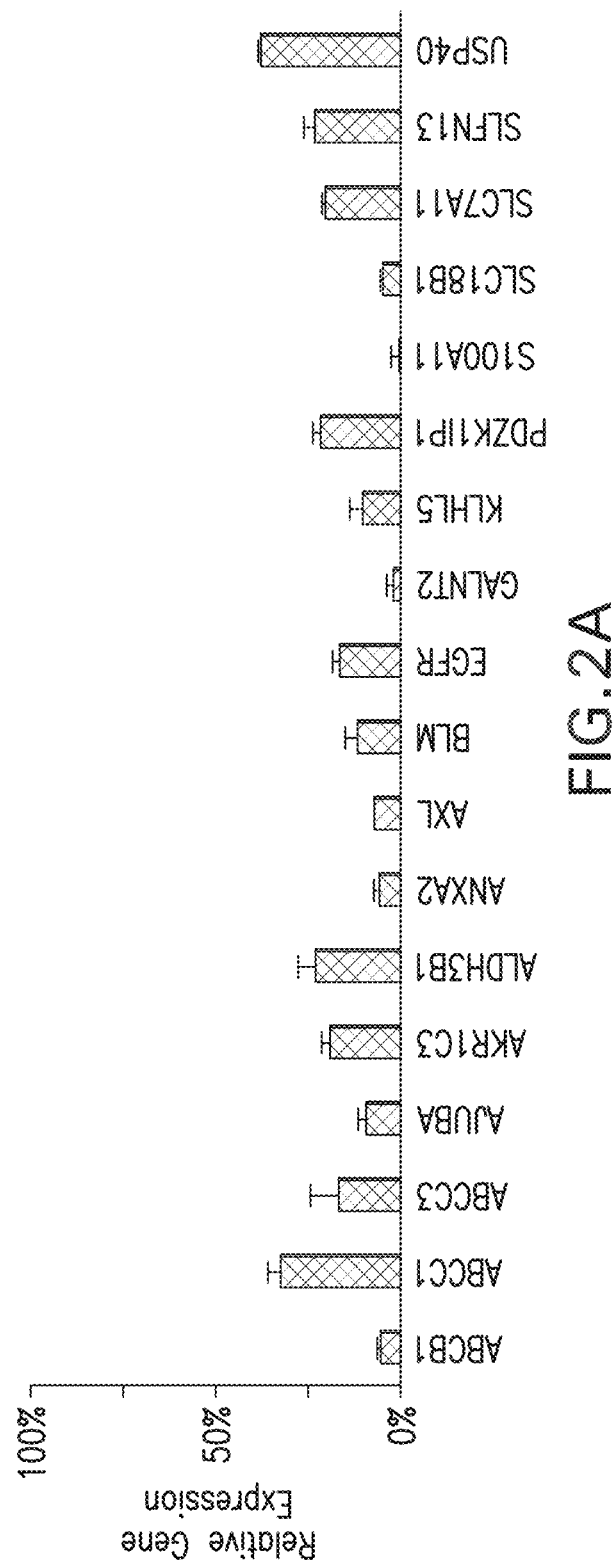
FIG. 2A is a bar graph showing relative gene expression compared to controls after 16 hours of siRNA exposure to OVCAR-8 cells.
Figure 2N:
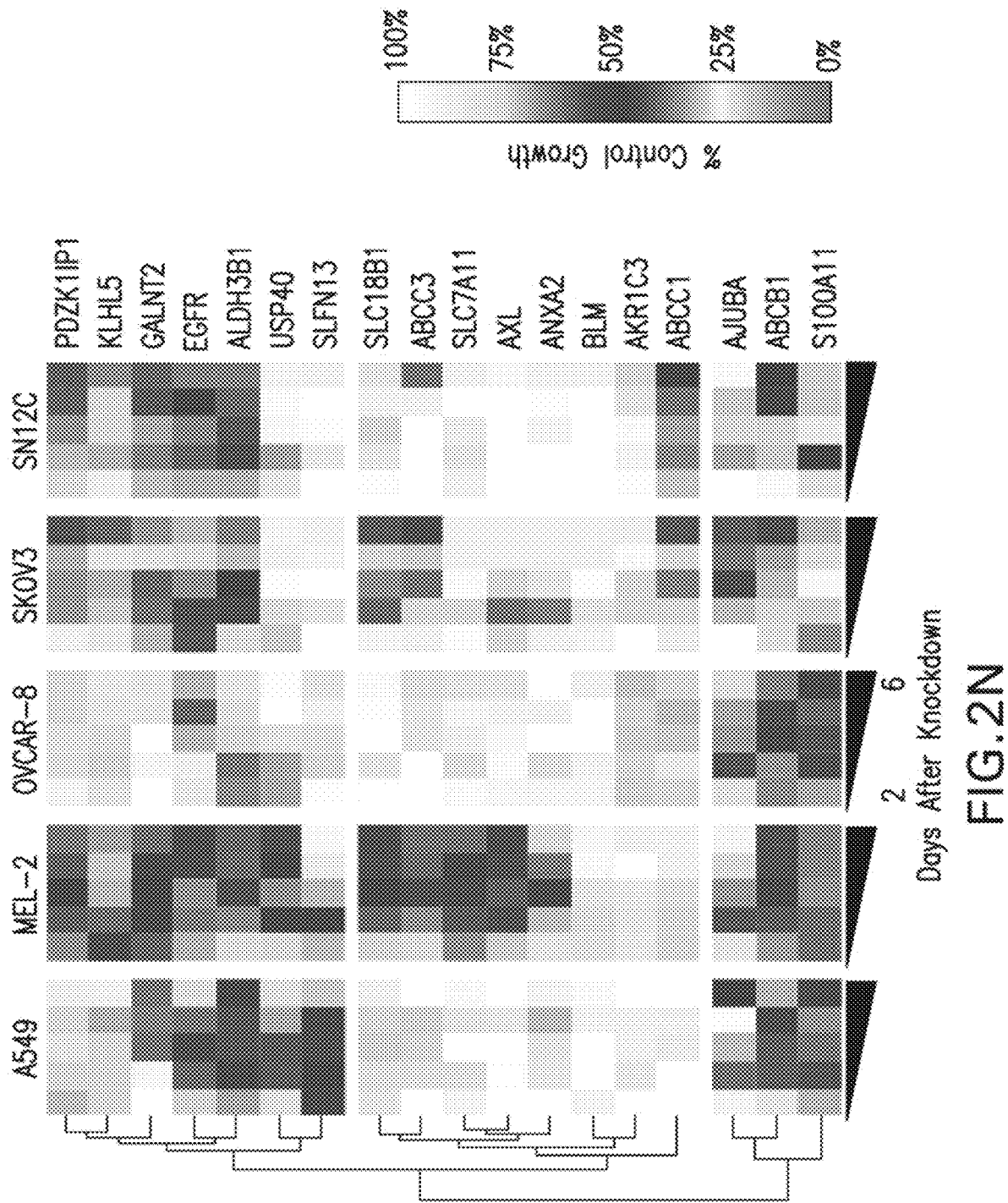
FIG. 2N shows time course data of siRNA knockdown on viability in five NCI-60 cell lines: A549 (basal alveolar lung adenocarcinoma), MEL-2 (metastatic melanoma), OVCAR-8 (high grade ovarian serous adenocarcinoma), SKOV-3 (ovarian adenocarcinoma), and SN12C (renal cell carcinoma). Time points shown are for 2, 3, 4, 5, and 6 days after the 16-hour knockdown exposure. Data represent mean of 3 replicates.
Figure 6C:
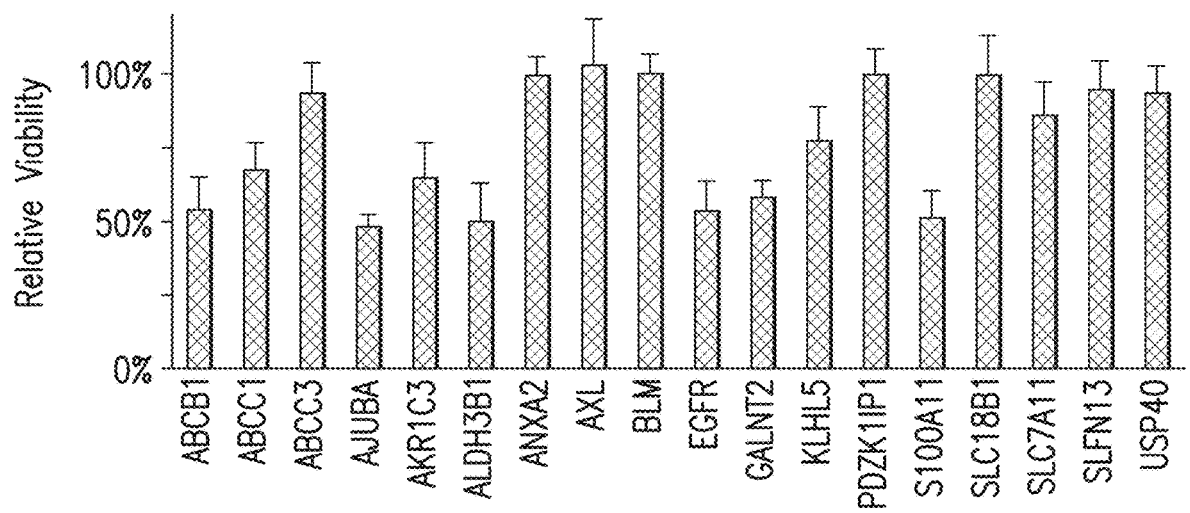
FIG. 6C shows viability as the percentage of controls at 72 hours after 16-hour siRNA exposure to OVCAR-8 cells. Data represents the mean±s. d. from 3 replicate cultures.

Results:

Gene knockdown was carried out using two complementary technologies, shRNA and siRNA. The lentiviral shRNA system used in this study allows permanent knockdown due to integration into the host genome. Knockdown efficiencies for most genes were excellent for all but six genes (ABCB1, AJUBA, BLM, EGFR, SLC18B1, and SLFN13) (FIG. 6A). Imaging analysis was performed after three days to assess the impact of knockdown on cells and knockdown of eight genes (ABCC1, ABCC3, GALNT2, KLHL5, PDZK11P1, S100A11, SLC7A11, or USP40) showed a decrease in viability in OVCAR-8 cells (FIG. 2A). The impact of shRNA knockdown on four cell lines assessed after five days indicated that knockdown of eleven genes reduced cell viability to below 75% in at least one cancer cell line and that four genes (GALNT2, PDZK11P1, S100A11, and USP40) reduced viability in multiple cell lines (FIG. 6C). Puromycin selection of the knockdown cells further reduced the number of viable cells. Permanent OVCAR-8 cell lines were established after puromycin selection and maintained for over a twenty-one day period for all but seven genes where there were few or no surviving cells after 21 days (GALNT2, PDZK11P1, S100A11, USP40, KLHL5, PDZK11P1, and ALDH3B1) (data not shown). This result is likely indicative of the severe impact of these genes on cell survival.

Since the shRNA knockdown was not efficient for several genes and permanent cell lines could not be established for seven genes, the impact of each gene on cell viability was further tested using a siRNA-based temporal knockdown system. Three to five siRNAs were designed, synthesized, and screened for their gene knockdown efficiencies via qRT-PCR analysis and the most efficient siRNA was selected for subsequent studies and typically had a >80% knockdown efficiency. The impact on viability was tested daily in five different cancer cell lines representing different cancer types (FIG. 2B-2N). Overall, all eighteen genes except for BLM reduced cell viability to below 80% in at least one cell line. S100A11 and AJUBA consistently reduced viability 50% or more across all five tested cell lines.

Example 4. Gene Knockdown Increases Sensitivity to a Large Proportion of Anticancer Compounds Results:

To measure the effect of a gene on drug effect, comparisons were made between high expressers of each gene and the wild type cells exposed to sham reagents. The impact of each gene on drug sensitivity was assessed using the temporal siRNA knockdown system on the OVCAR-8 cell line and a library of 346 drugs approved by FDA for clinical use or clinical trial represent a diversity of anticancer mechanisms emphasizing targeted therapies (Table 2). Statistical analysis was performed to determine the combinatorial effects (synergy or antagonism) of all pair-wise combinations of 18 genes against 346 drugs. Because the genes were putative drug resistance genes, synergism was expected to be detected in greater amounts than antagonism.

TABLE 2

Scoring of compounds by sum of observed SD values for 18 genes.

| Drug Cat. | Score | Drug Cat. | Score |
|---|---|---|---|
| DHFR - Pemetrexed | 73.43 | PDGFR - Sorafenib | 8.95 |
| JAK - Fedratinib | 56.68 | PI3K - Buparlisib | 8.79 |
| NA Syn - Floxuridine | 48.46 | HSP - AUY922 | 8.46 |
| DHFR - Methotrexate | 47.16 | HSP - Ganetespib | 8.4 |
| NA Syn - Raltitrexed | 44.53 | Transferase - APO866 | 7.8 |
| NA Syn - Gemcitibine HCI | 35.88 | PLK - Rigosertib | 6.43 |
| NA Syn - Gemcitibine | 34.12 | IL - Dexamethasone Acetate | 6.26 |
| NA Syn - Clofarabine | 33.4 | Aminopeptidase - Tosedostat | 5.66 |
| NA Syn - Cladribine | 29.78 | Aurora Kinase - JNJ - 7706621 | 5.07 |
| Raf - SB590885 | 27.34 | | |
| Topo. - Daunorubicin HCI | 24.68 | Bcr-Abl - Imatinib Mesylate | 4.83 |
| | | IkB/IKK-TPCA-1 | 4.7 |
| Topo. - Mitoxantrone HCI | 23.85 | PLK - GSK461364 | 4.65 |
| Raf - GDC - 0879 | 23.19 | HSP - Geldanamycin | 4.47 |
| Microtubule - Docetaxel | 21 | Androgen - Flutamide | 3.96 |
| Aurora Kinase - Barasertib | 20.03 | VEGFR - Regorafinib | 3.75 |
| | | Others - Epigallocatechin gallate | 3.64 |
| HSP - 17 - DMAG HCI | 19.7 | Hedgehog - Vismodegib | 3.36 |
| NA Syn - Bleomycin Sulfate | 19.53 | Hydroxylase - Isotretinoin | 3.36 |
| | | Hedgehog - Erismodegib | 3.22 |
| Bcr - Abl - Rebastinib | 17.66 | Bcr-Abl - WP1130 | 3.15 |
| Microtubule - | 17.57 | Hedgehog - Cyclopamine | 3.03 |

TABLE 2-continued

Scoring of compounds by sum of observed SD values for 18 genes.

| Drug Cat. | Score | Drug Cat. | Score |
|---|---|---|---|
| Epothilone B Microtubule - Epothilone A | 16.97 | Alkylating agent - Bendamustine HCL | 2.83 |
| Topo. - Topotecan HCl | 16.12 | ATM/ATR-CP-466722 | 2.79 |
| mTOR - CH5132799 | 15.96 | PARP - AG14361 | 2.72 |
| Topo. - Doxorubicin | 15.09 | c-Met - JNJ-38877605 | 2.72 |
| Src - Dasatinib | 14.95 | Proteasome - Bortezomib | 2.57 |
| PI3K - IC - 87114 | 14.65 | Alkylating agent - Altretamine | 1.75 |
| Topo. - Idarubicin HCl | 14.07 | NA Syn - Cytarabine | 1.63 |
| Microtubule - Paclitaxel | 13.63 | Folic Acid - Leucovorin Calcium | 1.29 |
| Src - KX2-391 | 13.4 | HDAC - Mocetinostat | 1.27 |
| Topo. - Epirubicin HCl | 12.82 | Kinesin - Ispinesib | 1.22 |
| Gamma-secretase-DAPT-(GSI-IX) | 12.69 | Others - Streptozotocin | 1.09 |
| PLK-BI2536 | 12.6 | NA Syn - Fludarabine | 0.4 |
| Aurora Kinase - AT9283 | 12.54 | Metabolite-D-glutamine | 0.27 |
| HDAC - Entinostat | 12.38 | CCR5 - Maraviroc | 0.11 |
| c-Kit - Amuvatinib | 12.37 | c-Kit - OSI-930 | -0.3 |
| Aurora Kinase - AMG 900 | 11.64 | c-Met - SU11274 | -0.42 |
| mTOR - Palomid 529 | 11.53 | DNMT - RG108 | -0.52 |
| HSP - Elesclomol | 11.26 | JAK - Momelotenib | -0.52 |
| PLK - Volasertib | 10.79 | Vitamin D2 analog - Doxercalciferol | -0.53 |
| TNF-alpha - Lenalidomide | 10.51 | TGF-beta - LY2157299 | -0.82 |
| Raf - Vemurafenib | 10.18 | Aurora Kinase - SNS-314 Mesylate | -1.05 |
| Endothelin - Zibotentan | 10.07 | Microtubule - Vincristine | -1.14 |
| Bcr-Abl - Nilotinib | 9.71 | HDAC - Vorinostat | -6.49 |
| Carbonic Anhydrase - Dorzolamide HCl | 9.66 | PKC - Enzastaurin | -6.53 |
| | | HSP - 17-AAG | -6.69 |
| Androgen -e Enzalutamid | -1.24 | NA Syn - Nelarabine | -6.77 |
| | | c-Met - PF-04217903 | -6.89 |
| Retinoid Bexarotene | -1.35 | Androgen - Andarine | -7.28 |
| Sodium Channel - Vinpocetine | -1.42 | Topo. - Irinotecan HCl | -7.65 |
| | | Microtubule - Nocodazole | -7.78 |
| Survivin - YM155 | -1.58 | ER/PR - Raloxifene HCl | -7.91 |
| NA Syn - Mercaptopurine | -1.59 | DNMT - Decitabine | -7.95 |
| | | PDE - Anagrelide HCl | -8.01 |
| CDK - Seliciclib | -1.72 | Transferase - Tipifarnib | -8.23 |
| APC - TAME | -1.98 | PI3K - LY294002 | -8.41 |
| Blinds metabolite - Dimesna | -2.17 | c-Met - SGX-523 | -8.5 |
| | | Microtubule - Vinblastine | -8.63 |
| Sirtuiin - Sirtinol | -2.18 | Aromatase - Aminoglutethimide | -9.32 |
| HDAC - JNJ-26481585 | -2.31 | NA Syn - Ftorafur | -9.75 |
| COX - Celecoxib | -2.38 | c-Kit - Pazopanib | -9.8 |
| Other - Pamidronate Disodium | -2.39 | Bcl-2-Obatoclax mesylate | -10.02 |
| GSK-3 - CHIR-99021 | -2.4 | mTOR - XL765 | -10.06 |
| Aurora Kinase - Alisertib | -2.8 | DNA-PK - NU7441 | -10.42 |
| | | IGF-1R - GSK1904529A | -10.83 |
| Aurora Kinase - Danusertib | -2.99 | NA Syn - Fludarabine Phosphate | -11.05 |
| Dehydrogenase - Mycophenolate mofetil | -3.2 | Calcium Channel - Ranolazine | -11.08 |
| IL - Dexamethasone | -3.28 | Liver X - GW3965 HCl | -11.35 |
| PARP - Rucaparib | -3.34 | VEGFR - Cediranib | -11.55 |
| TNF-alpha - Pomalidomide | -3.4 | GSK-3 - SB216763 | -11.62 |
| | | Others - GSK650394 | 12.12 |
| Topo. - Etoposide | -3.45 | c-Kit - Motesanib | -12.16 |
| VEGFR - Vatalanib 2HCl | -3.51 | Diphosphate FXR - GW4064 | -12.2 |
| Topo. - Teniposide | -3.64 | Pim - SGI - 1776 | -12.21 |
| Aurora Kinase - Tozasertib | -4.08 | JAK - Ruxolitinib | -12.37 |
| | | FLT3 - Quizartinib | -12.85 |
| Kinesin SB 743921 | -4.09 | DprEl - BTZ043 | -13.06 |
| Alkylating agent - Procarbazine HCl | -4.1 | JAK - Tofacitinib | -13.15 |
| | | ER/PR - | -13.23 |
| Alkylating agent - Busulfan | -4.1 | Tamoxifen Citrate | |
| c-Kit - Masitinib | -4.23 | Dehydrogenase - Gossypol | -13.34 |
| Syk - Fostamatinib | -4.27 | P450 - Itraconazole | -13.51 |
| NA Syn - Capecitabine | -4.37 | Caspase - PAC - 1 | -13.56 |
| Casein Kinase - Silmitasertib | -4.51 | Bcl-2 - Navitoclax | -13.79 |
| | | mTOR - WYE-354 | -13.86 |
| Others - Coenzyme Q10 | -4.69 | HMG-CoA Reductase - Fluvastatin | -20.51 |
| PDGFR - Imatinib | -5.05 | | |
| EGFR - Chrysophanol | -5.16 | PI3K - PIK-93 | -20.62 |
| c-Kit - Telatinib | -5.24 | Glucocorticoid - Prednisone | -20.64 |
| E3 Ligase - Nutlin-3 | -5.25 | | |
| Cholesterol Absorption - Ezetimibe | -5.31 | HDAC - Belinostat | -20.81 |
| | | Dehydrogenase - Mycophenolic acid | -20.87 |
| PI3K - Quercetin | -5.63 | NA Syn - Cisplatin | -21 |
| E2 conjugating - BAY 11-7082 | -5.7 | ER/PR - Estrone | -21.19 |
| | | Glucocorticoid - Hydrocortisone | -21.54 |
| Bcl-2 - ABT-737 | -5.9 | | |
| UAK - S-Ruxolitinib | -6.2 | PARP - Iniparib | -21.58 |
| Androgen - Megestrol Acetate | -6.46 | Antibiotics - Salinomycin | -21.61 |
| | | E3 Ligase - Thalidomide | -21.65 |
| Microtubule - ABT-751 | -13.93 | mTOR - GSK2126458 | -22.4 |
| c-Met - PHA-665752 | -13.95 | Sirtuin - EX 527 | -22.45 |
| Autophagy - Temozolomide | -14.24 | Kinesin - AZ 3146 | -22.56 |
| | | ER/PR - Mifepristone | -22.75 |
| ATM/ATR - KU-55933 | -14.37 | AMPK - A-769662 | -22.81 |
| | | ER/PR - Toremifene Citrate | -22.88 |
| VEGFR - Brivanib | -14.38 | | |
| Androgen - Ostarine | -14.47 | c-Kit - Dovitinib | -22.96 |
| c-Met - BMS 777607 | -14.73 | NA Syn - Dacarbazine | -23.22 |
| IkB/IKK - BX-795 | -14.94 | Androgen - Bicalutamide | -23.24 |
| Aromatase - Formestane | -14.97 | Substance P - Aprepitant | -23.29 |
| FLT3 - Tandutinib | -14.99 | Akt - MK-2206 2HCl | -23.29 |
| NA Syn - Hydroxyurea | -15.1 | c-Met - BMS 794833 | -23.46 |
| Retinoid - Tretinoin | -15.11 | Src - Bosutinib | -23.5 |
| Alkylating agent - Lomustine | -15.64 | CDK - Flavopiridol | -23.63 |
| | | Alkylating agent - Cyclophosphamide | -23.81 |
| SGLT - Dapagliflozin | -15.72 | | |
| Adjuvent - Mesna | -15.88 | CDK - AT7519 | -24.02 |
| ERCC3 - Triptolide | -15.95 | Aromatase - Exemestane | -24.27 |
| PKC - Sotrastaurin | -16.11 | Immune - STF-62247 | -24.47 |
| SGLT - Phloretin | -16.21 | NA Syn - Carboplatin | -24.62 |
| HDAC - Sodium butyrate | -16.25 | PI3K - 3-Methyladenine | -24.92 |
| | | CSF-1R - Linifanib | -25.28 |
| c-Kit - Tivozanib | -16.34 | SGLT - Canagliflozin | -25.46 |
| Telomerase - BIBR 1532 | -16.4 | ATM/ATR - KU-60019 | -25.5 |
| | | Glucocorticoid - Meprednisone | -25.82 |
| Aerobic glycolysis - Lonidamine | -16.85 | Aromatase - Anastrozole | -26.38 |
| EGFR - Lapatinib Ditosylate | -16.97 | ER/PR - Estradiol | -26.58 |
| | | ALK - Crizotinib | -26.66 |
| Immune - Imiquimod | -17.18 | Glucocorticoid - Triamcinolone | -26.66 |
| NA Syn - Ifosfamide | -17.33 | | |
| Arginyl aminopeptidase-Ubinimex | -17.36 | EGFR - OSI-420 | -27.08 |
| | | PPAR - Rosiglitazone | -27.32 |
| | | VEGFR - Lenvatinib | -27.5 |
| FAK - PF - 562271 | -17.41 | ER/PR - Fulvestrant | -27.59 |
| Immune - Cyclosporin A | -17.68 | MEK - PD0325901 | -37.42 |
| | | PPAR - Pioglitazone | -37.6 |
| HDAC - Sodium valproate | -17.88 | ALDH1 - Disulfiram | 37.83 |
| | | IAP - AT406 | -38.03 |
| Xanthine Oxidase - Febuxostat | -18.04 | Gamma-secretase - 0YO-1027 | -38.72 |
| PDGFR - Crenolanib | -18.09 | PARP - Veliparib | -38.85 |
| NA Syn - Carmofur | -18.23 | HDAC - Trichostatin A | -38.93 |
| EGFR - Lapatinib | -18.34 | HER2 - Neratinib | -39.86 |
| NA Syn - Fluorouracil | -19 | MEK - TAK-733 | -40.08 |
| PARP - Olaparib | -19.18 | TGF-beta - LY2109761 | -40.45 |
| Aromatase - Letrozole | -19.26 | p38 MAPK - SB 203580 | -40.85 |
| DNA-PK - PIK-75 | -19.42 | HER2 - BMS-599626 | -40.89 |
| c-Kit - Sunitinib Malate | -19.63 | EGFR-NVP-AEE788 | -41.08 |
| 5-lipoxygenase - Zileuton | -19.64 | EGFR - WZ4002 | -41.61 |
| | | mTOR - Ku-0063794 | -41.94 |
| DNMT - Azacitidine | -19.79 | CDK - PHA-793887 | -42.75 |
| NA Syn - Oxaliplatin | -19.87 | HDAC - Pracinostat | -43.48 |
| HMG-COA Reductase - Simvastatin | -20.34 | Chk - AZD7762 | -43.68 |
| | | JAK - NVP-BSK805 2HCl | -43.77 |
| P450 - Abiraterone | -20.38 | Raf - AZ628 | -43.85 |
| JAK - CEP33779 | -27.66 | PI3K - PIK-90 | -44.52 |
| MEK - Trametinib | -27.77 | mTOR - INK 128 | -44.98 |
| PI3K - CAL-101 | -27.89 | MEK - CI-1040 | -45.66 |
| ALK - LDN193189 | -28.37 | FGFR - PD173074 | -46.63 |
| Purine analog - | -28.48 | EGFR - CUDC-101 | -46.83 |

TABLE 2-continued

Scoring of compounds by sum of observed SD values for 18 genes.

| Drug Cat. | Score | Drug Cat. | Score |
|---|---|---|---|
| Azathioprine | | Aurora Kinase - | −47.04 |
| Syk - R406 | −28.54 | ENMD-2076 | |
| Bcr-Abl - Ponatinib | −28.62 | mTOR - Rapamycin | <u><u>−48.37</u></u> |
| IGF - 1R - Linsitinib | −28.72 | Akt - Triciribine | <u><u>−49.23</u></u> |
| VDA chemical - | −28.75 | p38 MAPK - | <u><u>−50.99</u></u> |
| Vadimezan | | Doramapimod | |
| FAK - PF 573228 | −28.79 | mTOR - AZD8055 | <u><u>−51.01</u></u> |
| Aurora Kinase - | −28.81 | FAAH - PF-3845 | <u><u>−51.78</u></u> |
| CYC116 | | Chk - LY2603618 | <u><u>−52.09</u></u> |
| Tie-2 - Tie2 kinase | −28.87 | Proteasome - Ixazomib | <u><u>−52.76</u></u> |
| ROCK - Y-27632 | −28.91 | PI3K - ZSTK474 | <u><u>−52.94</u></u> |
| 2HCl | | | |
| VEGFR - Vandetanib | −29.2 | Src - Saracatinib | <u><u>−53.14</u></u> |
| Wnt/beta-catenin - | −29.25 | EGFR - Pelitinib | <u><u>−54.75</u></u> |
| XAV-939 | | EGFR - Afatinib | <u><u>−54.76</u></u> |
| E3 Ligase - Serdemetan | −29.35 | HDAC - PCI-24781 | <u><u>−54.91</u></u> |
| FXR - WAY-362450 | −29.97 | | |
| EGFR - Gefitinib | −30.02 | mTOR - Temsirolimus | <u><u>−56.85</u></u> |
| Aurora Kinase - PF- | −30.13 | PI3K - PI-103 | <u><u>−56.96</u></u> |
| 03814735 | | PI3K - GDC-0941 | <u><u>−58.02</u></u> |
| CDK - Palbociclib | −30.45 | BTK - Ibrutinib | <u><u>−58.62</u></u> |
| TGF-beta - SB 431542 | −30.82 | CDK - SNS-032 | <u><u>−62.71</u></u> |
| VEGFR - Axitinib | −30.9 | mTOR - Everolimus | <u><u>−63.1</u></u> |
| PI3K - XL147 | −30.94 | | |
| p38 MAPK - | −30.98 | | |
| LY2228820 | | | |
| CETP - Dalcetrapid | −31.1 | | |
| HIF - | −31.84 | | |
| 2-Methoxyestradiol | | | |
| TGF-beta - SB 525334 | −32.05 | | |
| ATM/ATR - Torin 1 | −32.55 | | |
| PI3K - YM201636 | −32.89 | | |
| HSP - BIIB021 | −33.01 | | |
| Proteasome - MLN9708 | −34 | | |
| Sirtuin - SRT1720 | −34.27 | | |
| EGFR - Erlotinib HCl | −34.42 | | |
| Gamma secretase - | −34.92 | | |
| MK-0752 | | | |
| mTOR - Deforolimus | −35.43 | | |
| ALK - TAE684 | −35.61 | | |
| mTOR - BEZ235 | −35.65 | | |
| ER/PR - | −35.82 | | |
| Medroxyprogesterone | | | |
| Topo. - Irinotecan | −36.08 | | |
| FGFR - Nintedanib | −36.11 | | |
| Bcl-2 - TW-37 | −36.72 | | |
| HDAC - AR-42 | −36.88 | | |
| S1P - Fingolimod | −37.06 | | |
| ATM/ATR - Torin 2 | −37.17 | | |
| MEK - Selumetinib | <u><u>−63.99</u></u> | | |
| Wee1 - MK-1775 | <u><u>−64.04</u></u> | | |
| p38 MAPK - | <u><u>−64.86</u></u> | | |
| PH-797804 | | | |
| EGFR - Dacomitinib | <u><u>−68.29</u></u> | | |

Table 2 shows scoring of compounds by sum of observed SD values for 18 genes. Maximum and minimum contribution of a single gene is +5 and −5. Scores beyond the thresholds selected for charts in FIG. 4 are double underlined.

Figure 3A:
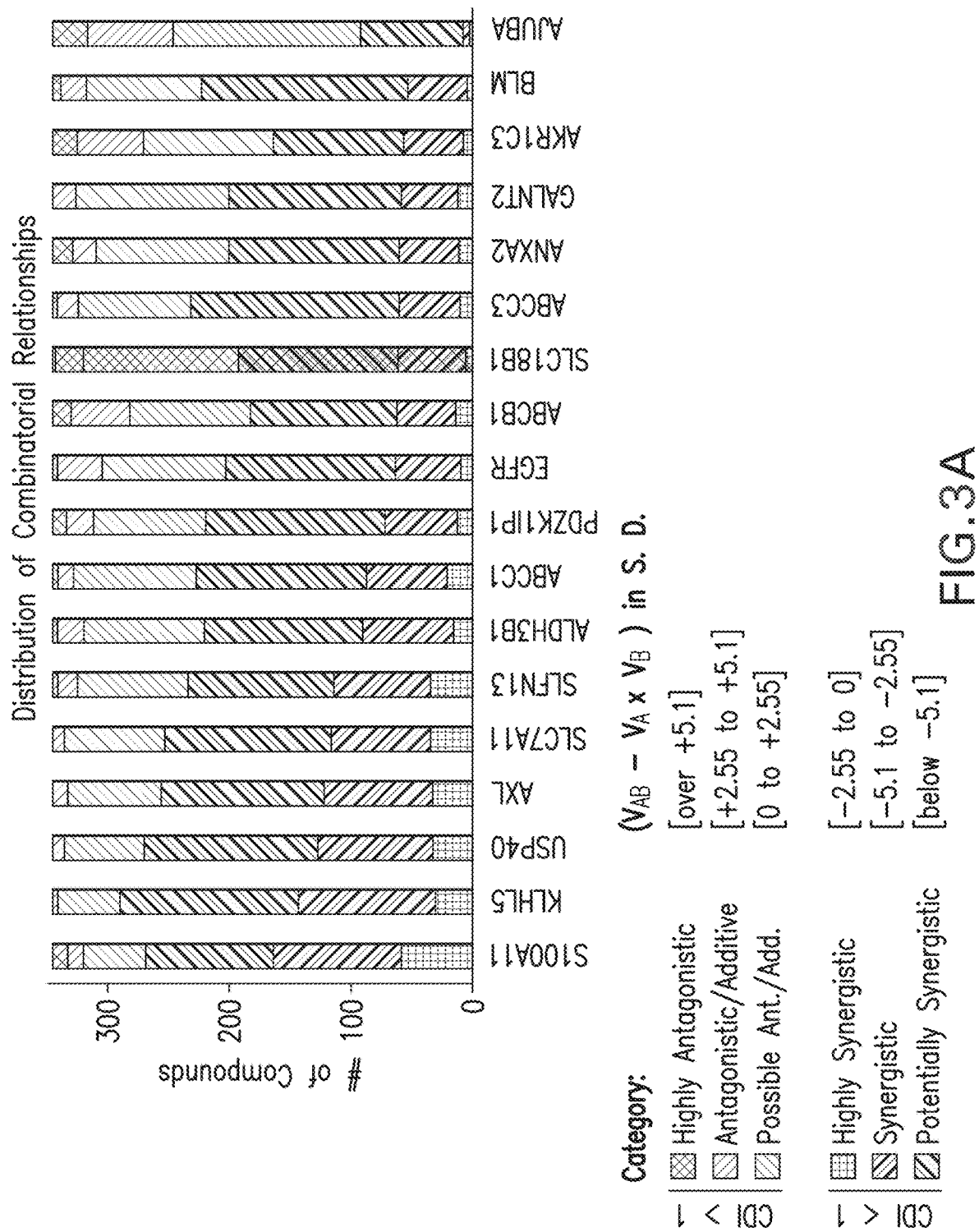
FIG. 3A is a histogram showing frequency of interactions observed with the 6,593 drug-siRNA knockdown combinations as categorized into six groups. Synergy has a Coefficient of Drug Interaction (CDI)<1 while Antagonism/Additive is >1. Compounds are further categorized by the strength of the interaction as defined by difference between $V_{AB}-V_A \times V_B$ measured in standard deviations (S.D.). Slight differences from $V_{AB}$ are in light shading. Moderate differences (>2.55 S.D.) are in medium shading. Large differences (>5.1 S.D.) are in dark shading ("Highly Synergistic" and "Highly Antagonistic").

Drug-siRNA interactions are determined by observed viability for drug only ($V_A$), viability for siRNA knockdown only ($V_B$), and viability for combination treatment with siRNA and drug ($V_{AB}$). Synergy is often measured using the coefficient of drug interaction ($CDI=V_AB/V_A \times V_B$) which compares the observed combination effect with the product of the single treatment. In theory, CDI<1 is indicative of synergy while CDI>1 is indicative of antagonism or additive effect in a multiplicative model. In this study, drug-siRNA interactions are classified into six categories based on the observed viability difference between the observed $V_A$ Band expected $V_A \times V_B$ as measured by standard deviations (SD) of viability (FIG. 3A). The first threshold represents a 99% confidence interval (2.55 SD) and the second is doubly stringent (5.1 SD). If the differences are beyond the 5.1 SD, the interactions are considered as highly synergistic (difference <−5.1 SD) or highly antagonistic (Difference >5.1 SD). Interactions with differences between the two thresholds are considered synergistic (−2.55 SD to −5.1 SD) or antagonistic/additive (2.55 SD to 5.1 SD). Interactions with differences between 0 and −2.55 SD are likely synergistic while those interactions with differences between 0 and 2.55 SD are likely antagonistic/additive.

Figure 3B:
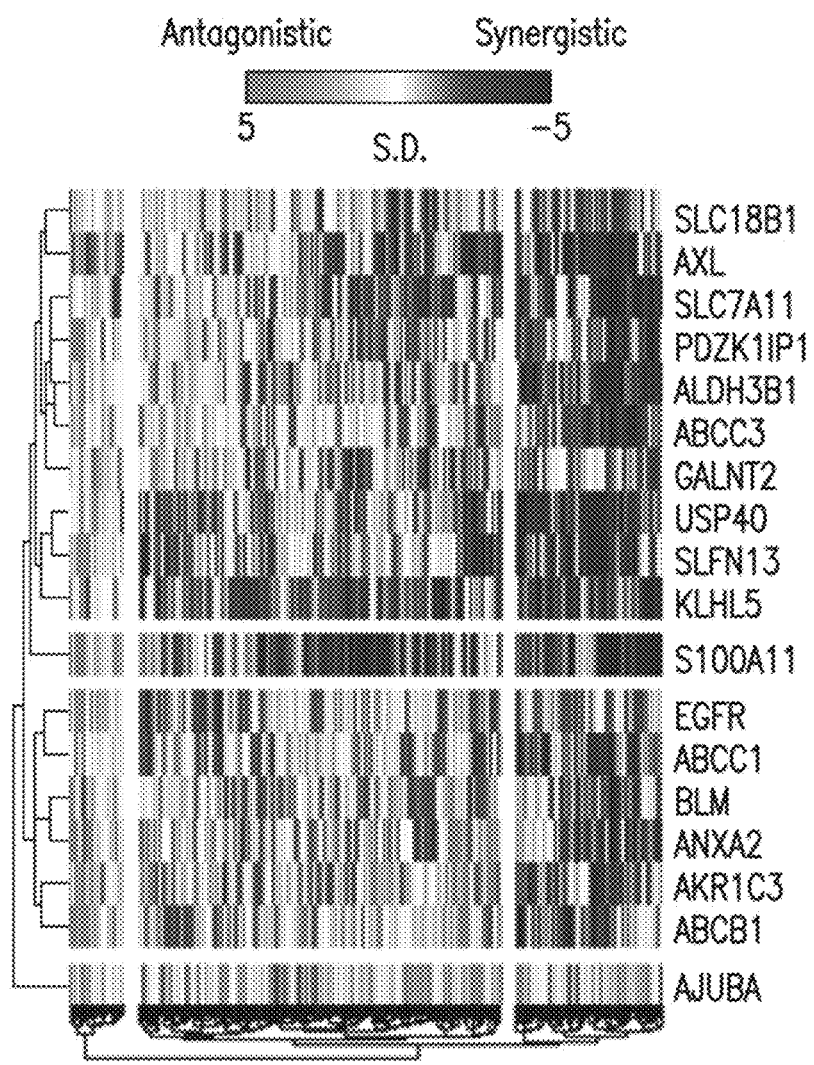
FIG. 3B shows hierarchical clustering of genes (horizontal) and drugs (vertical) using gene-siRNA combinatorial effects for all siRNA-drug pairs.
Figure 3C:
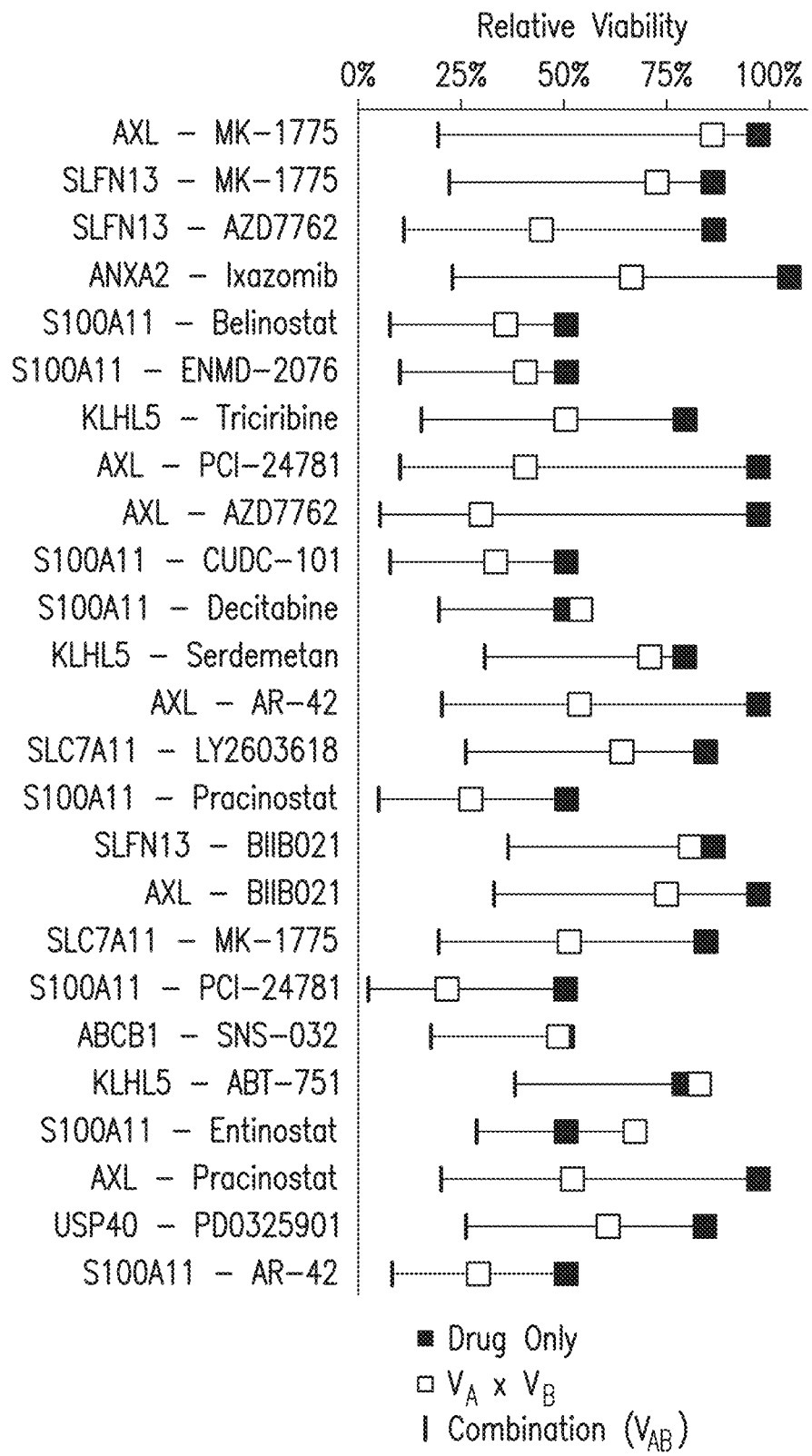
FIG. 3C is a graph showing top combinatorial pairs. The graph shows gene-knockdown combinations with the highest difference between observed and expected results. ■ represents drug only; □ represents $V_A \times V_B$; horizontal line represents combination ($V_{AB}$). Graph features synergy combinations with highest significance (<−9.5 S.D.).

Use of standard deviation as part of the synergy/antagonism determination improves upon CDI alone as it accounts for observed experimental variance and does not over-predict synergy/antagonism for combinations at low viabilities. In practice, it excludes synergistic or antagonistic combinations near CDI of 1 and combinations with small differences between observed and expected combination effect (FIG. 3C). Overall, 1535 (24.6%) of the 6228 (18× 346) studied combinations are categorized as synergy (SD<−2.55), with 5.7% as highly synergistic and 18.9% as synergistic. There are 7.1% antagonistic/additive combinations (SD>2.55), of which 2.1% are highly antagonistic (FIG. 3A). These results are consistent with patterns expected of genes that promote drug resistance genes.

Figure 7A:
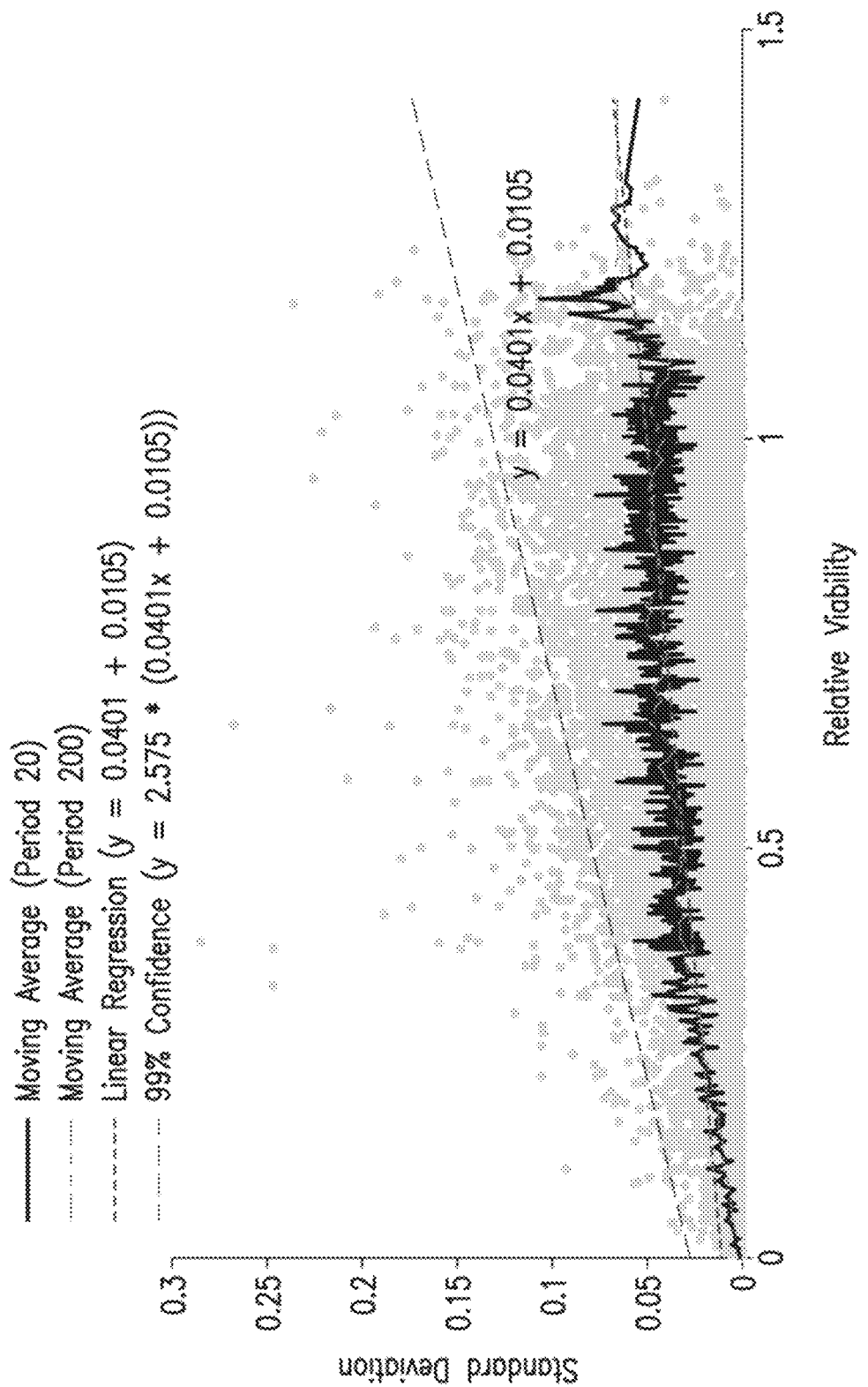
FIGS. 7A-7C show drug-siRNA interactions.
Figure 7B:
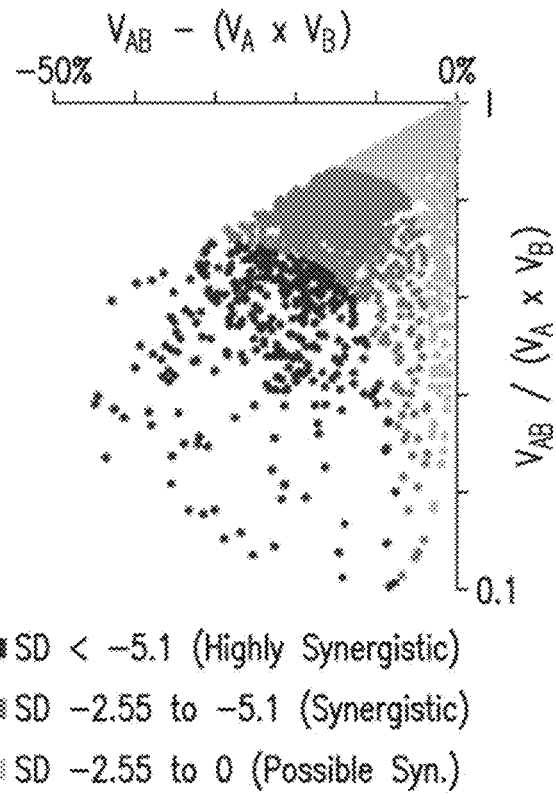
Figure 7C:
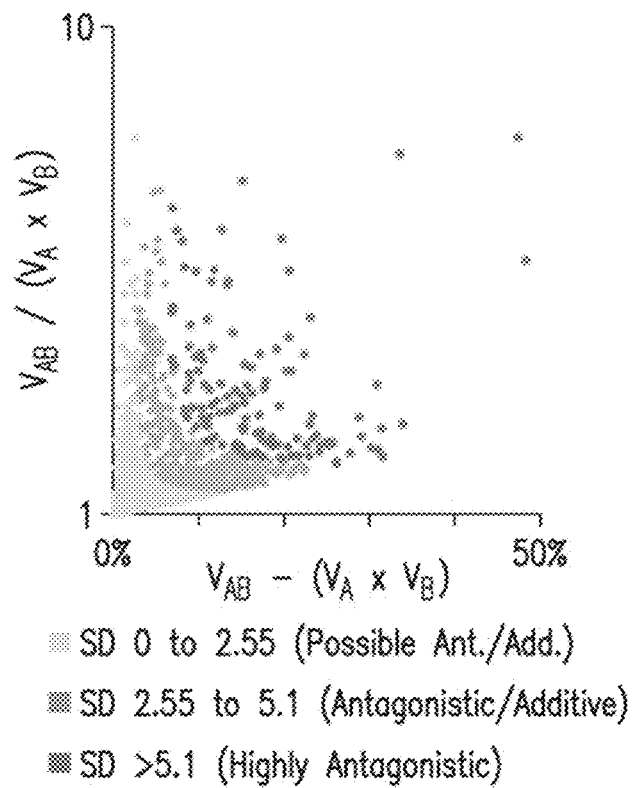

The number and types of drugs showing synergy with siRNA depend on the genes. In the initial screening, 17 of 18 genes (with the exception of AJUBA) showed synergy with over 50 compounds (FIG. 7A). The most synergistic gene knockdowns were S100A11, KLHL5, USP40, AXL, and SLC7A11, which feature more than 100 synergistic combinatorial relationships with compounds with over 30 being highly synergistic. Twelve or fewer antagonistic/additive or highly antagonistic compounds were identified with knockdown of KLHL5, USP40, AXL or SLC7A11. Hierarchical clustering of the drug-siRNA interaction data matrix was used to cluster the genes to elucidate their relationship for drug interaction. The clustered heatmap of all 18 genes by 346 drugs (FIG. 3B) presents a global view of drug-gene relationships. Six compounds have a highly antagonistic pattern, shown at the top of cluster 1. The second cluster contains compounds that have relatively few synergistic or antagonistic pairs, with the occasional signal of synergy with EGFR, ABCC1, USP40, SLFN13, KLHL5, AXL, or S100A11. The third cluster contains compounds with a primarily synergistic signature. Antagonistic combinations were rare for drugs in Clusters 2 and 3, although strong antagonism was occasionally observed with knockdowns of ANXA2, S100A11, AKR1C3, ABCB1, or AJUBA. The predominance of synergistic relationships in seventeen genes indicates that high expression of these genes effectively decrease drug efficacy, suggesting that the gene panel is predominantly comprised of drug resistance genes.

Example 5. Identification of Strongly Synergistic siRNA-Drug Combination Pairs

Results:

FIG. 3C presents specific drug-siRNA pairs with the strongest synergies between siRNA and drugs observed in this study. These pairs have small CDI as well as large deviation of viability from expectation. Eight of the best siRNA-drug pairs involve S100A11, which interacts with inhibitors for various classes of compounds including five HDAC inhibitors (Belinostat, Pracinostat, PCI-24781, AR-42, and CUDC-101). HDAC inhibitors also possess strong synergies with five other genes (AXL, SLC7A11, GALNT2, USP40, and PDZK11P1). Frequently among the top synergizing pairs are MK-1775 [WEE1 inhibitor], AZD7762 [CHK1 inhibitor], and BIIB021 [Hsp90 inhibitor]. The genes showing strong synergies are also those with numerous synergistic compounds. Of the interactions depicted in FIG. 3C, several siRNA-drug combinations result in the near-complete killing of the cells. These combinations, due to their strong killing effect, have intriguing potential for therapeutic development for combination therapy.

Example 6. Synergy and Antagonism Atlas for Anticancer Drugs

Results:

In order to determine the synergy or antagonism potential of drugs, each was scored based on the mean deviation from synergistic expectation of viability synergy across the 18 gene panel (Table 2). The mean value of synergy/antagonism for each drug is graphically shown in FIG. 4A, which clearly revealed that drugs with several mechanisms of action have high synergistic potential. These include drugs that inhibit (1) the GFR-PI3K-AKT-mTOR pathway, (2) Cell Cycle Inhibitors, (3) the MEK-MAPK (ERK) pathway, and (4) Epigenetics related compounds (HDAC inhibitors). Antagonistic relationships between drugs and siRNA were far less frequent. The mechanisms that frequently had antagonistic relationships included: 1) DHFR (dihydrofolate reductase) inhibitors, 2) inhibitors of nucleic acid synthesis, microtubules, and topoisomerase, 3) Raf inhibitors. A hierarchical clustered heatmap shows the individual synergy score for the siRNA-drug pairs between all 18 genes and the top 38 most synergistic compounds (score less than −2.25) (FIG. 4B) and top 16 most antagonistic compounds (scores greater than 1) (FIG. 4C) as ranked the mean standard deviation value. Drugs with similar mechanisms of action usually clustered together in both heatmaps.

Example 7. Commonly Synergized Compounds

Figure 8A:
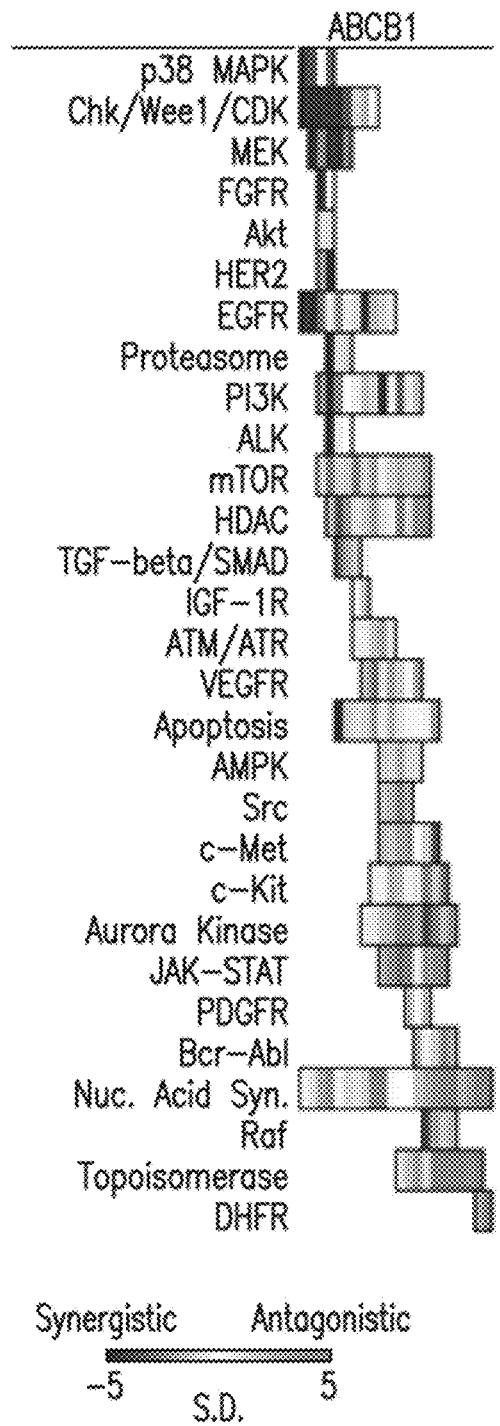
FIGS. 8A-8R show combinatorial relationships between genes and drugs of selected mechanisms. Mechanism map indicating the relationship of each anti-cancer compound (grouped by mechanism of action). Scoring for each drug is the mean of the observed distance $V_{AB}-V_A \times V_B$ measured in standard deviations (S.D.). Order of compounds is consistent across figures as well as FIGS. 3A-3C.
Figure 8B:
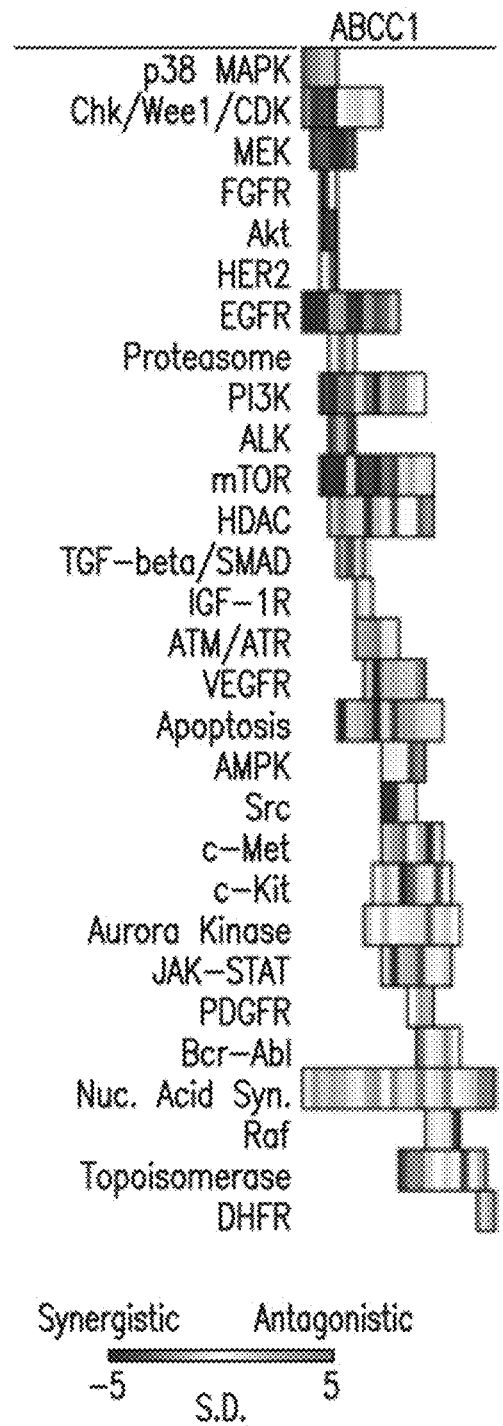
Figure 8C:
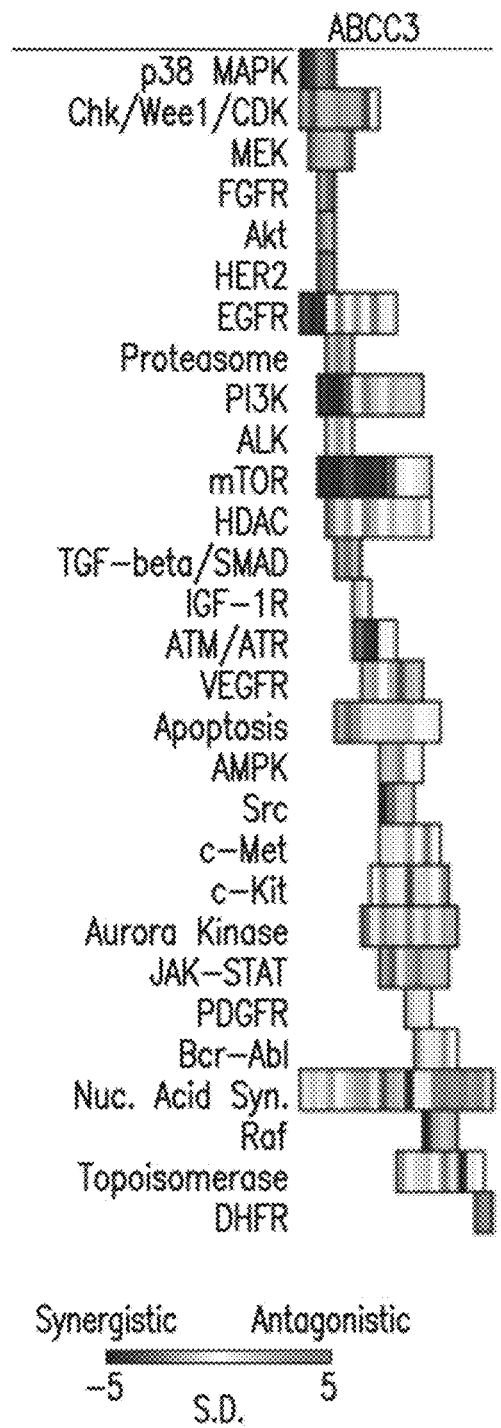
Figure 8D:
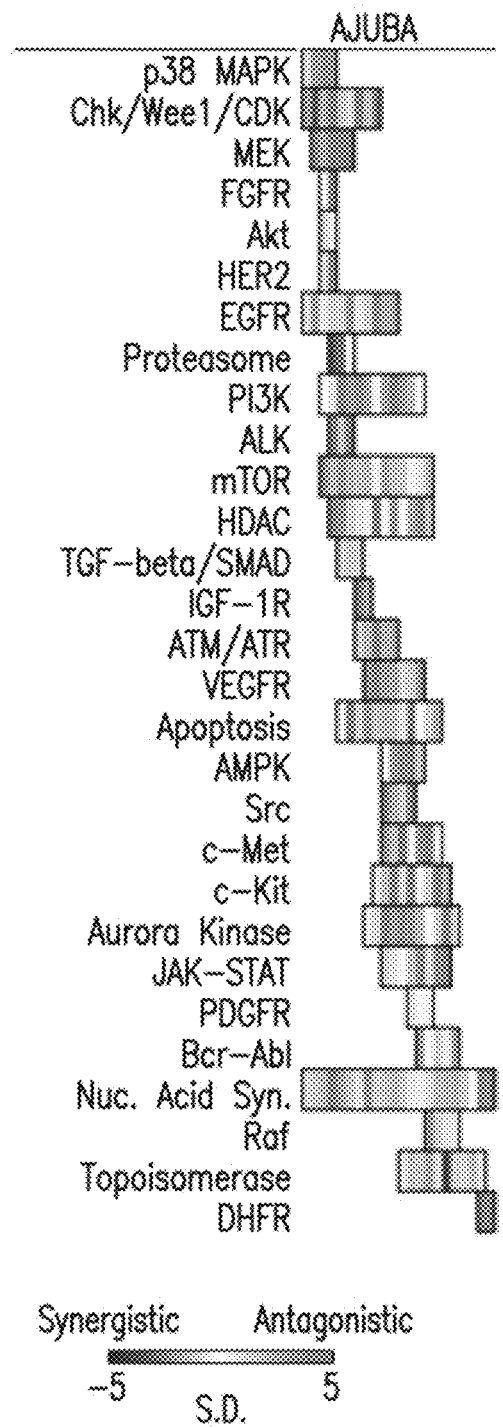
Figure 8E:
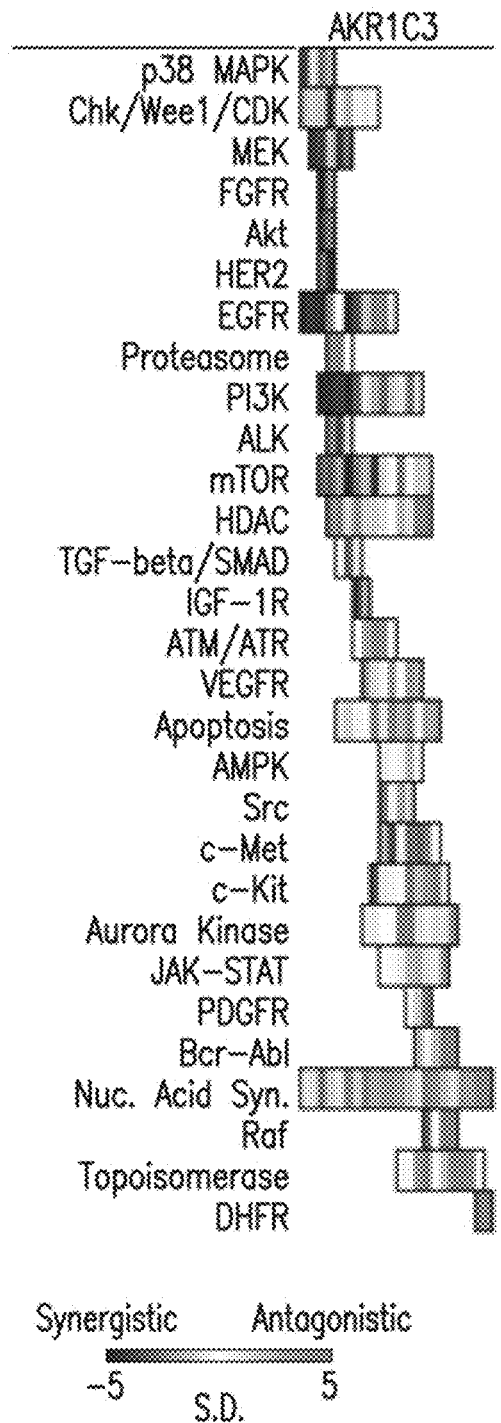
Figure 8F:
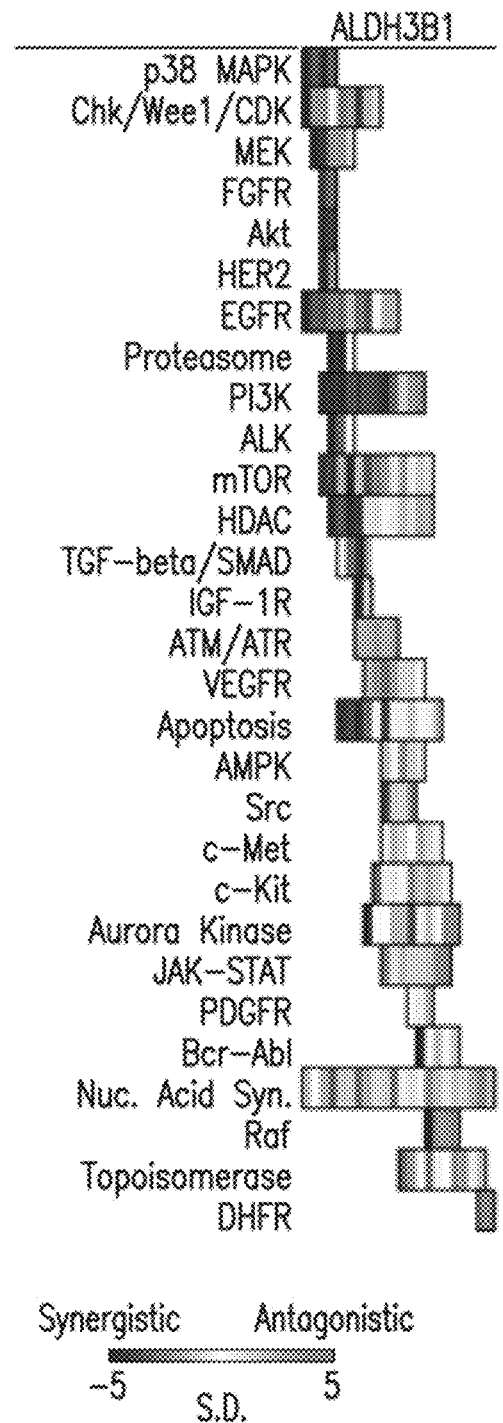
Figure 8G:
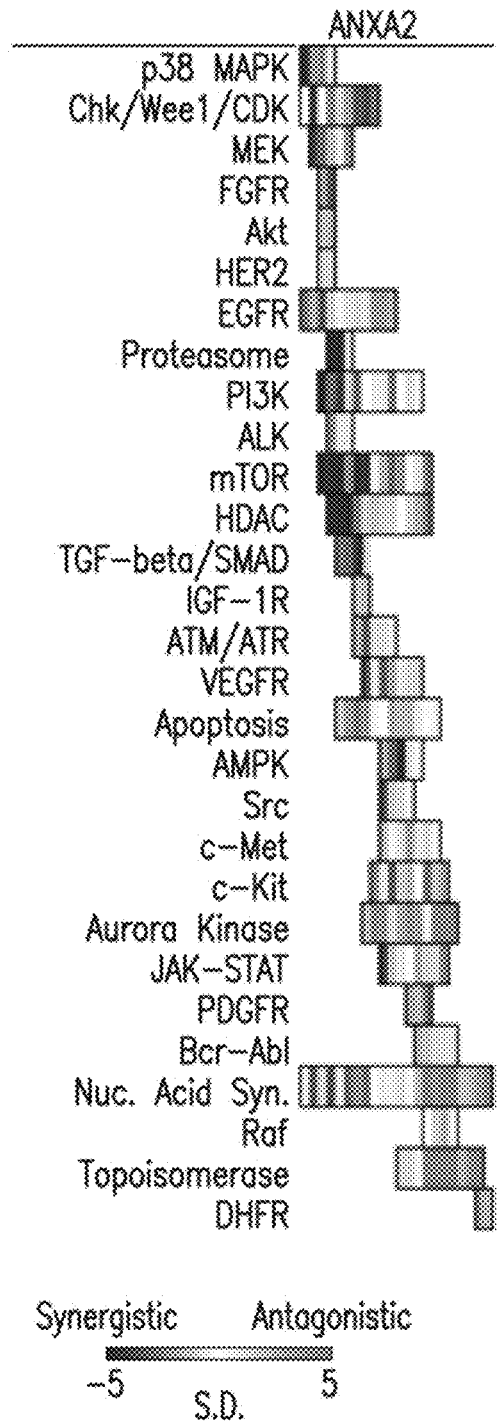
Figure 8H:
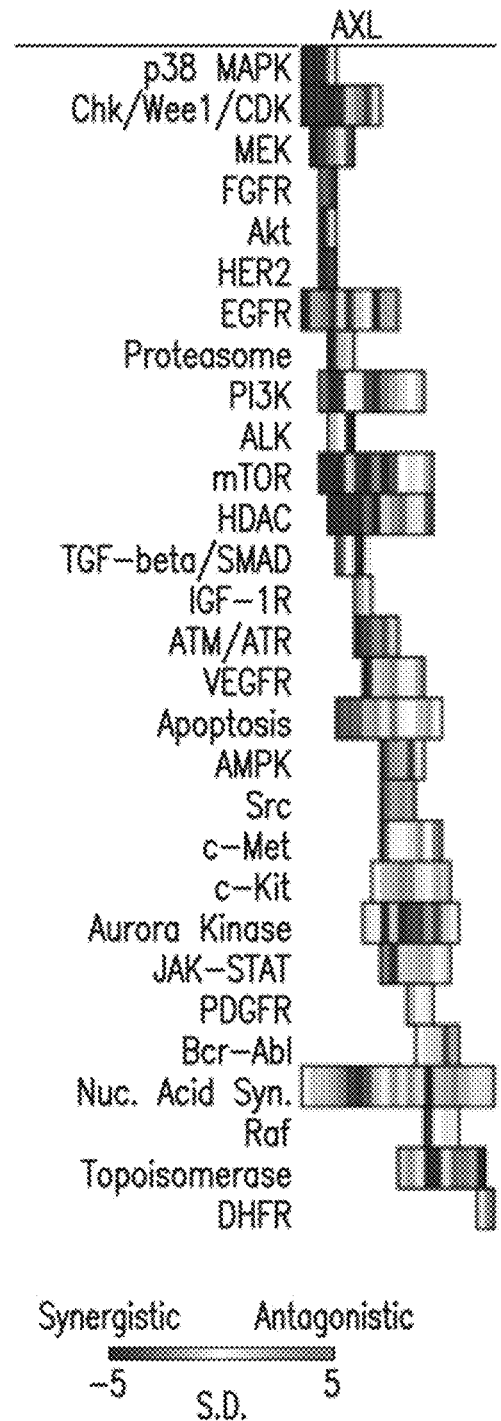
Figure 8I:
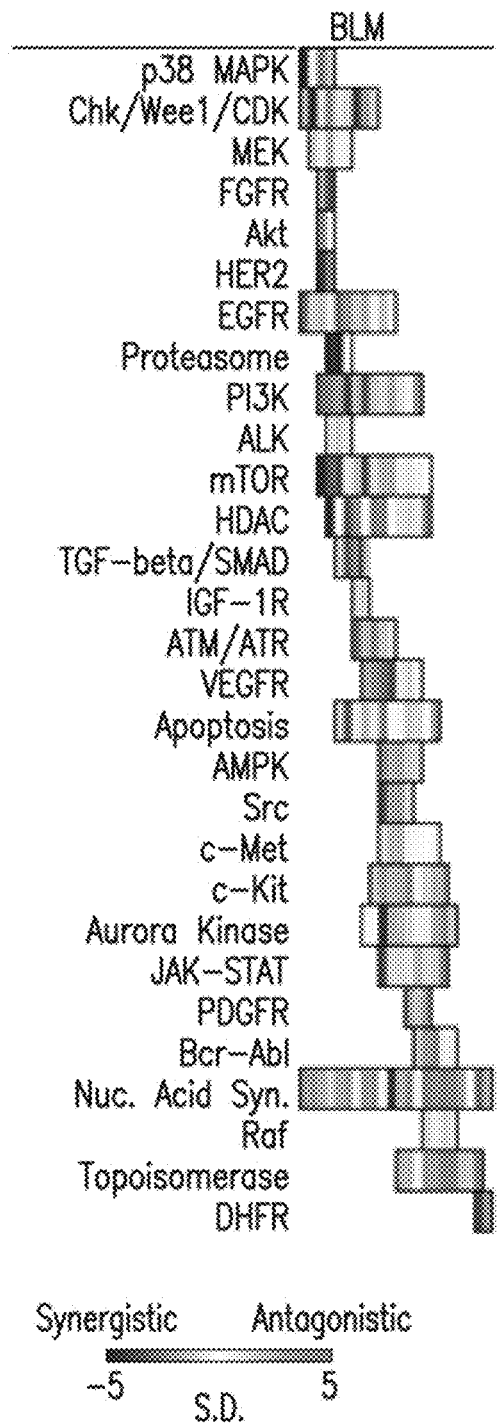
Figure 8J:
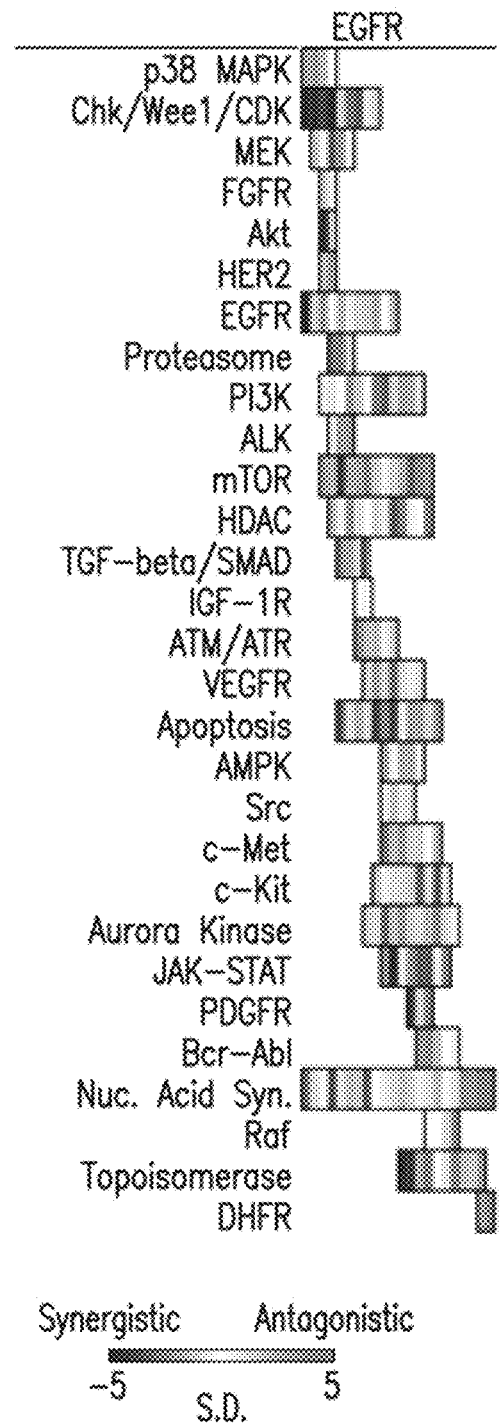
Figure 8K:
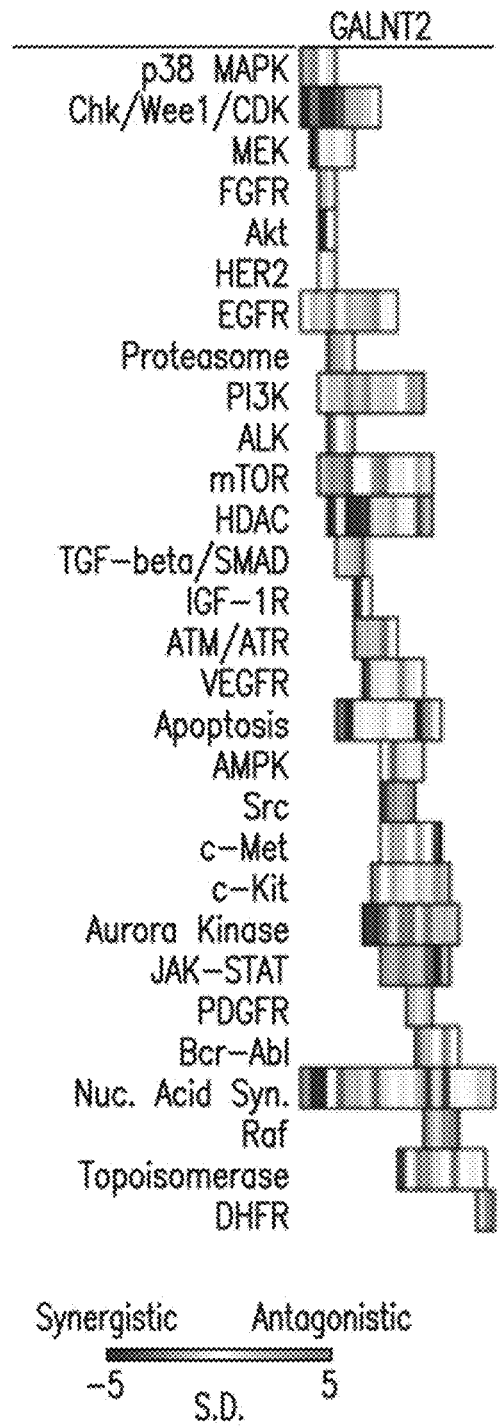
Figure 8L:
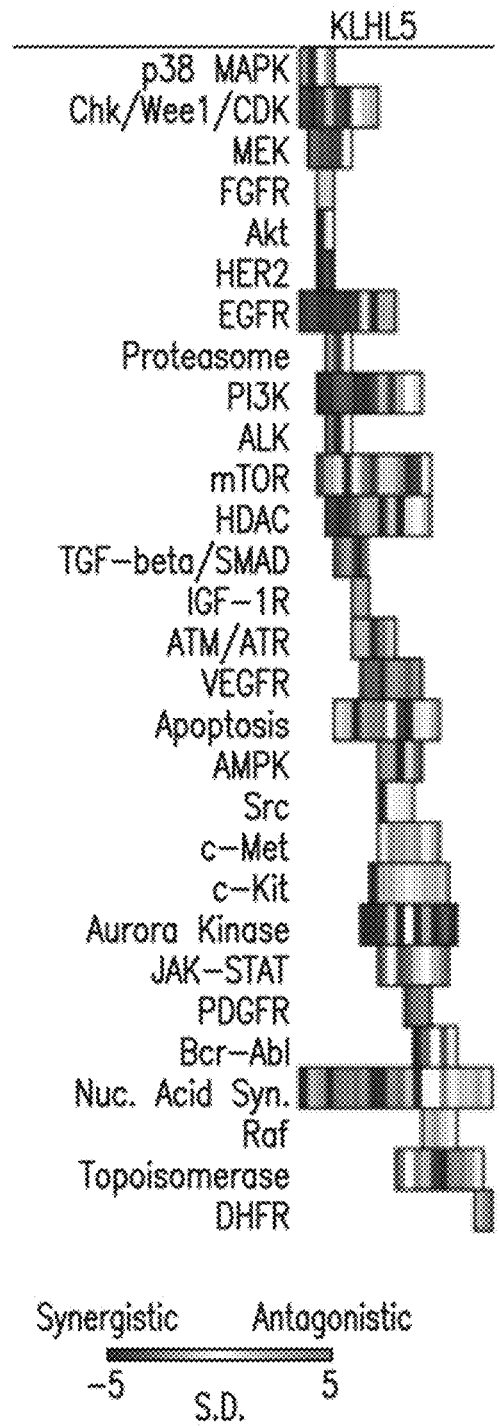
Figure 8M:
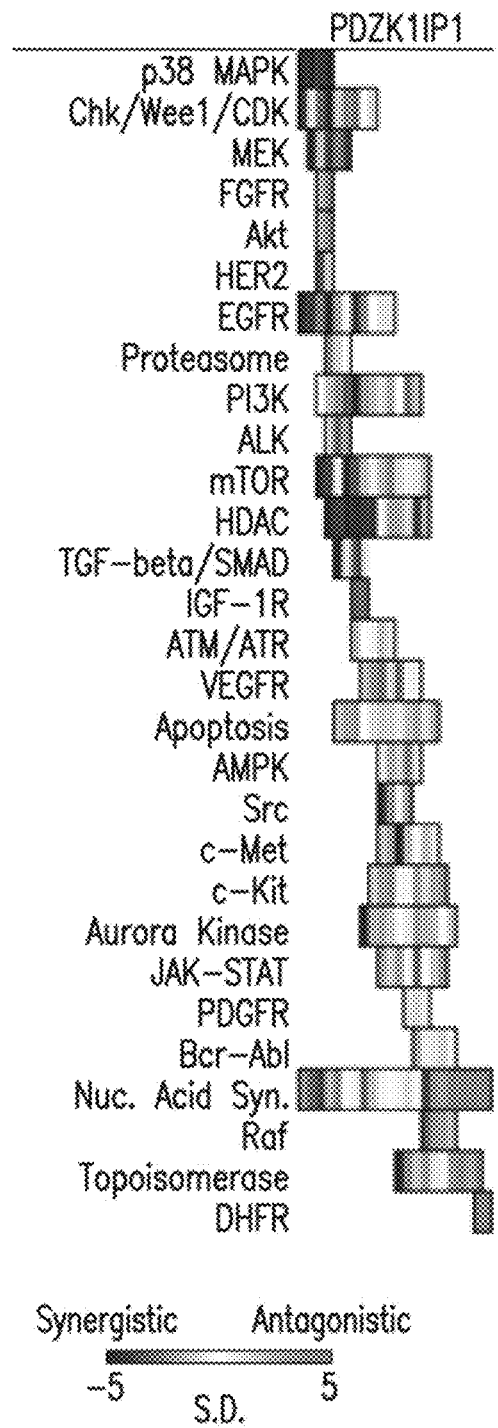
Figure 8N:
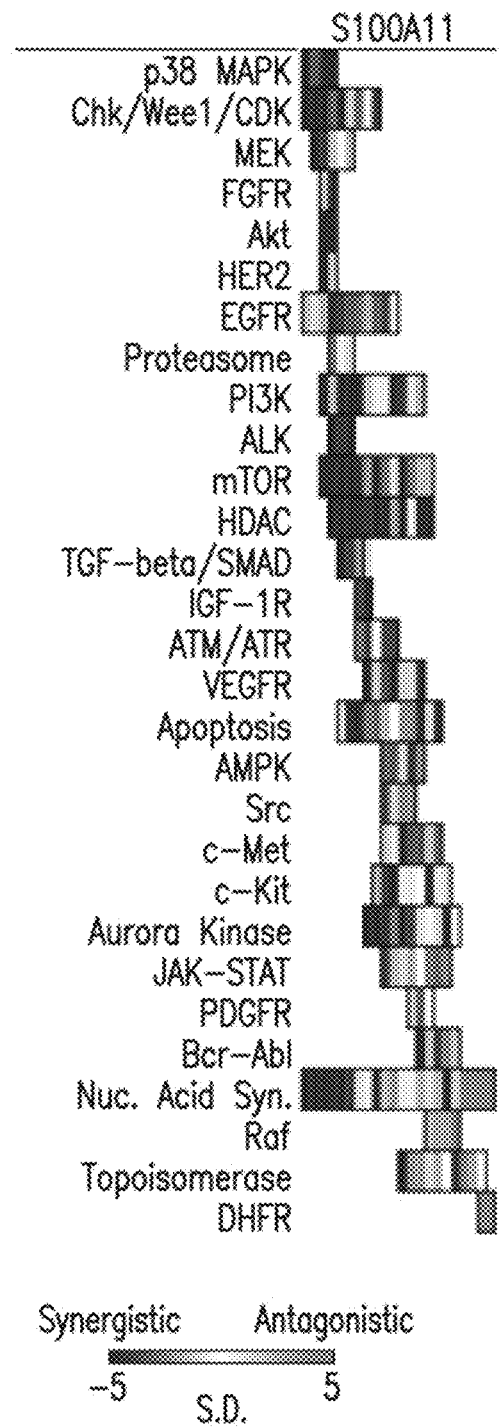
Figure 8O:
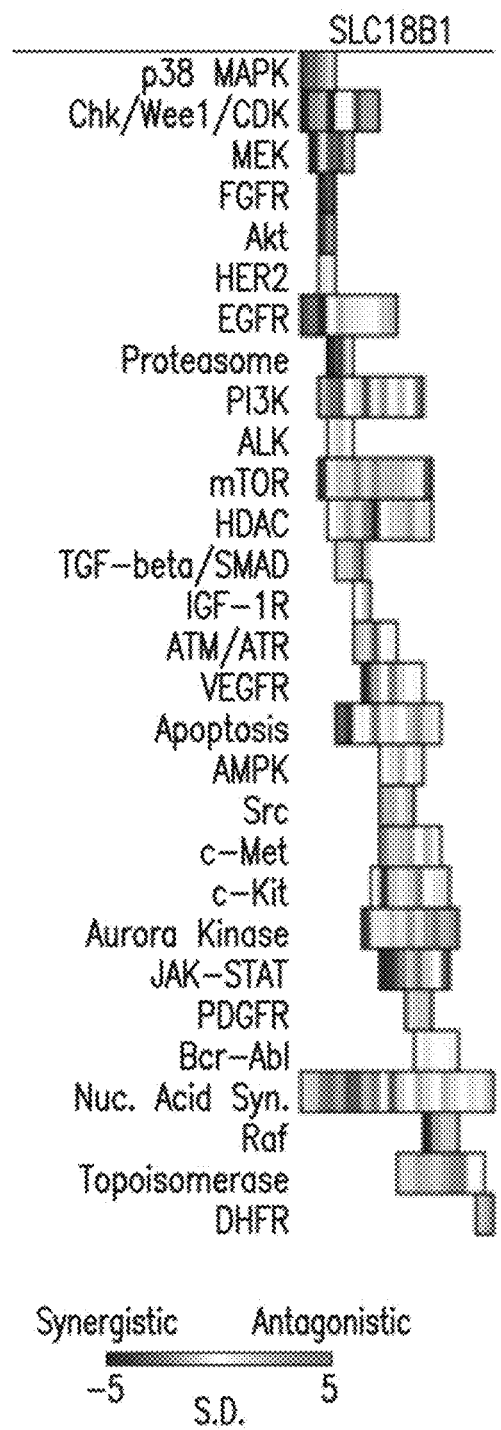
Figure 8P:
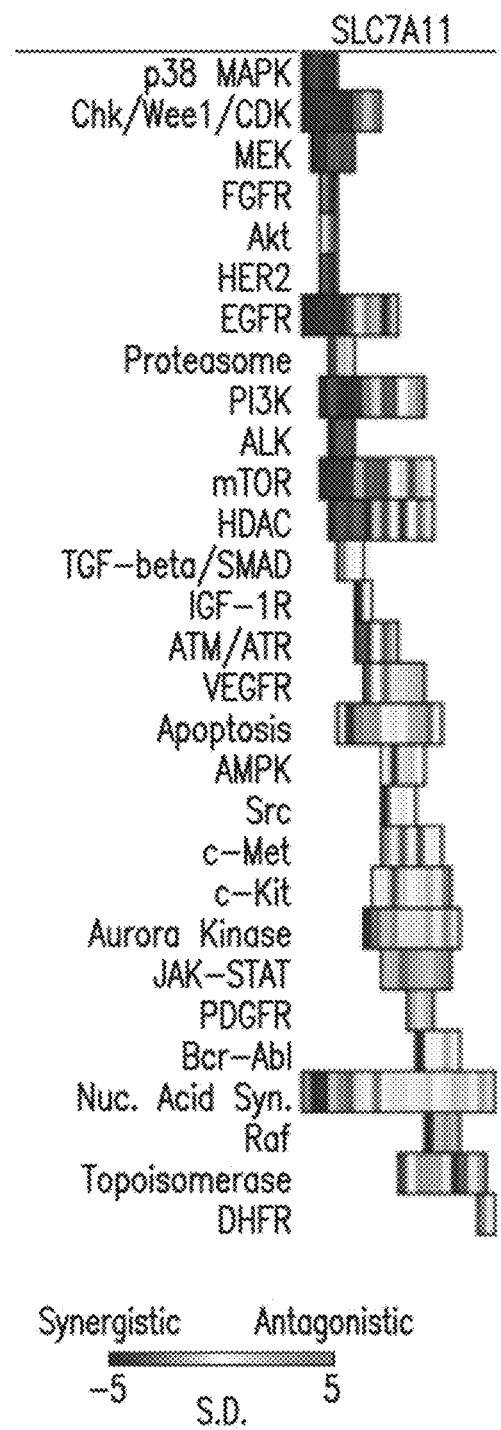
Figure 8Q:
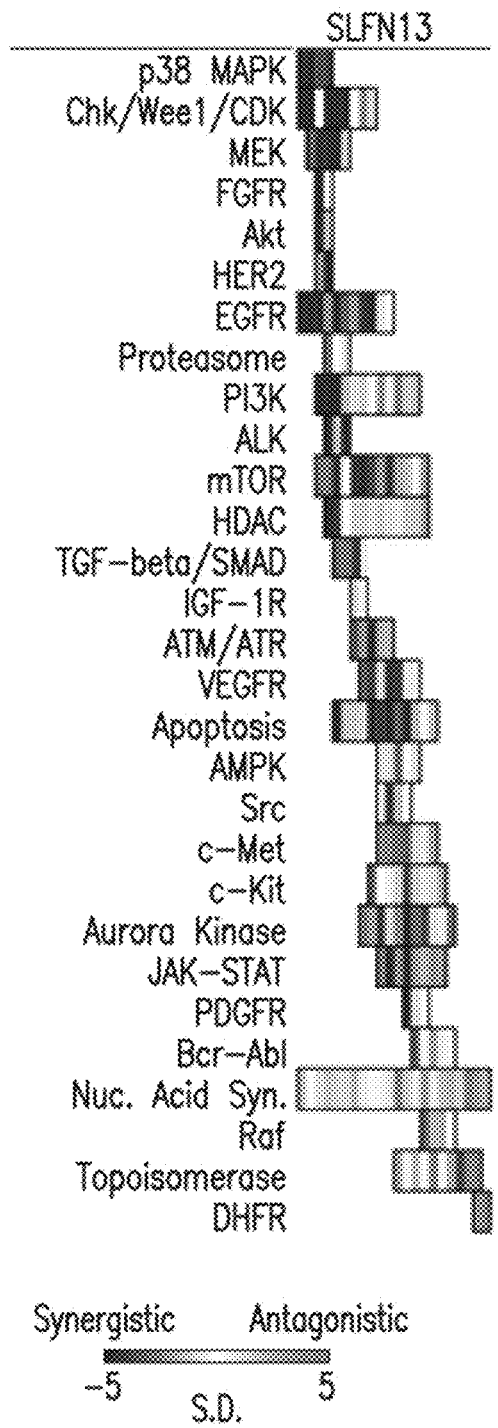
Figure 8R:
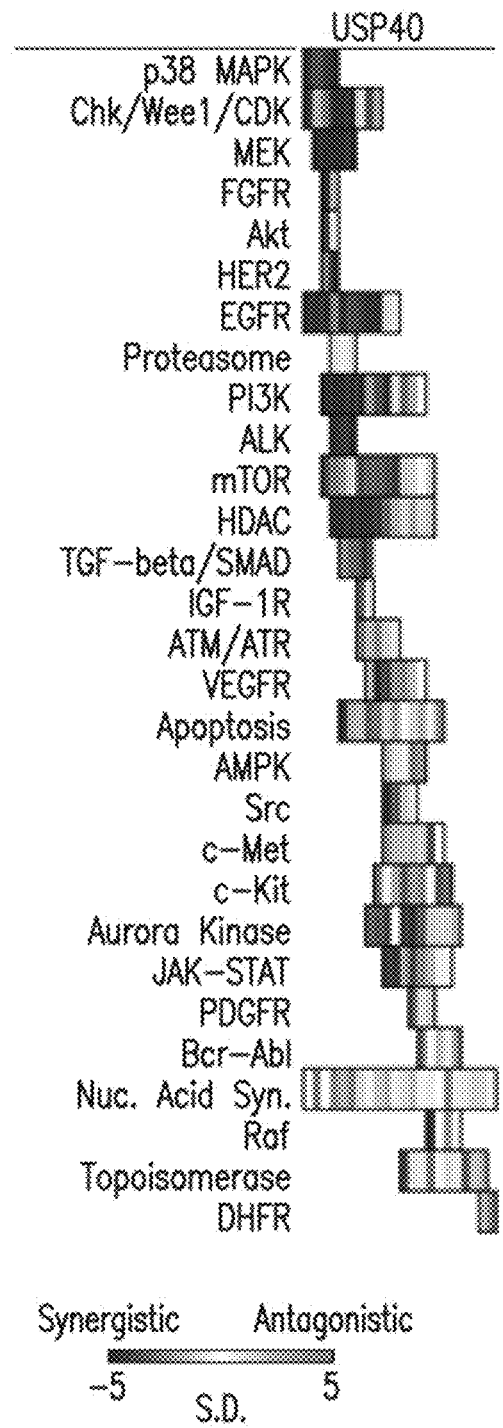

Results:

The first group of most synergistic compounds revealed by this panel of 18 genes consist of inhibitors of the GFR-PI3K-AKT-mTOR pathway, which include three growth factor receptors (GFR): EGFR, ERBB2 (HER2) and FGFR (FIG. 4B). The EGFR inhibitor, Dacomitinib showed high synergy with 15 genes, while Pelitinib and Afatinib possess similar patterns of synergy. EGFR knockdown generally showed partial synergy with EGFR inhibitors but was less pronounced than synergies with other genes (FIG. 8A-8R). Other notable GFR inhibitors that showed significant synergy with nine or more genes were Neratinib [HER2 inhibitor], BMS599626 [HER2 inhibitor], and PD173074 [FGFR inhibitor]. PI3K and mTOR inhibitors were also highly synergistic. PI3K inhibitors PI-103, ZSTK474 and GDC-0941 showed synergy to the vast majority of genes (FIG. 4B). Everolimus had the strongest synergism (synergy with 14 genes) with Temsirolimus and several mTOR inhibitors showing similar patterns (FIG. 4B).

The second major group of commonly synergized compounds is those that target cell cycle control (WEE1, CHK1, CDK, and Aurora Kinase). MK-1775, a WEE1 inhibitor, has high synergy with 13 genes and represents some of the most highly synergistic combinations. This high level of synergism was also observed with CHK1 inhibitors such as AZD7762 and LY2603618. Two CDK inhibitors (SNS-032 and PHA-793887) have strong synergies with multiple genes as well. Two of the eleven tested Aurora Kinase inhibitors (ENMD-2076 and PF-03814735) showed significant synergy while Barasertib was antagonistic and other Aurora Kinases largely lacked significant synergies or antagonisms. A notable exception was that KLHL5 knockdown in combination with Aurora Kinase inhibitors resulted in significant synergy with eight of the eleven inhibitors (FIG. 8L).

The third group of synergistic compounds targets the MEK-MAPK (ERK) pathway. The most synergistic MEK inhibitors is Selumetinib, which synergizes with 16 genes. MEK inhibitors CI-1040 and Trametinib are also among the top synergistic compounds. Highly synergistic drugs also include p38-MAPK inhibitors such as PH-797804 (14 genes), Doramapimod (11 genes), and SB 203580 (9 genes) (FIG. 4B).

The fourth group of highly synergistic compounds is HDAC inhibitors (HDACi). Pracinostat (11 genes), PCI-24781 (12 genes), and AR-42 (10 genes) are highly synergistic. CUDC-101 (11 genes), a dual inhibitor of EGFR and HDAC, is also a top synergistic compound. The most consistent synergizing genes with HDACi are S100A11 which is highly synergistic with 10 of 12 tested 20 HDACi. Four other genes (AXL, KLHL5, SLC7A11, and USP40) are also highly synergistic with at least six HDACi.

Example 8. Commonly Antagonized Compounds

Results:

Dihydrofolate reductase (DHFR) inhibitors (also known as folate antimetabolites) inhibit one or more of the enzymes that use folate or derivatives as substrates: DHFR, thymidylate synthase, and GARFT. Pemetrexed, commonly used in lung cancer chemotherapy, is highly antagonistic with nearly all genes. Methotrexate, commonly used to treat cancers including breast, skin, lung, or head and neck, also shows antagonism with most knockdowns. Also among the top antagonistic compounds are inhibitors of topoisomerase, nucleic acid synthesis, or microtubules (FIG. 4C). A notable exception to the antagonism pattern is that AXL siRNA is synergistic with most of these drugs showing antagonism with other siRNAs (FIG. 4C).

Raf inhibitors are frequently antagonized. GDC-0879 [B-Raf and cellular pERK inhibitor], SB590885 [B-Raf inhibitor] are antagonistic with multiple genes (FIG. 4C). Sorafenib [B-Raf, c-Raf, PDGFR, and VEGFR inhibitor] has a similar antagonistic profile (FIG. 8). However, the increased frequency of antagonism with Raf inhibitors is not observed with AZ628 [B-Raf and C-Raf inhibitor] which shows nearly the opposite pattern. AZ628 is synergistic with knockdown of ten genes, six of which (ABCC3, AKR1C3, ALDH3B1, PDZK11P1, SLC7A11, and USP40) have significant antagonism with GDC-0879. These observations are intriguing as inhibitors of targets both upstream and downstream of Raf show frequent synergism with the studied genes.

Figure 4A:
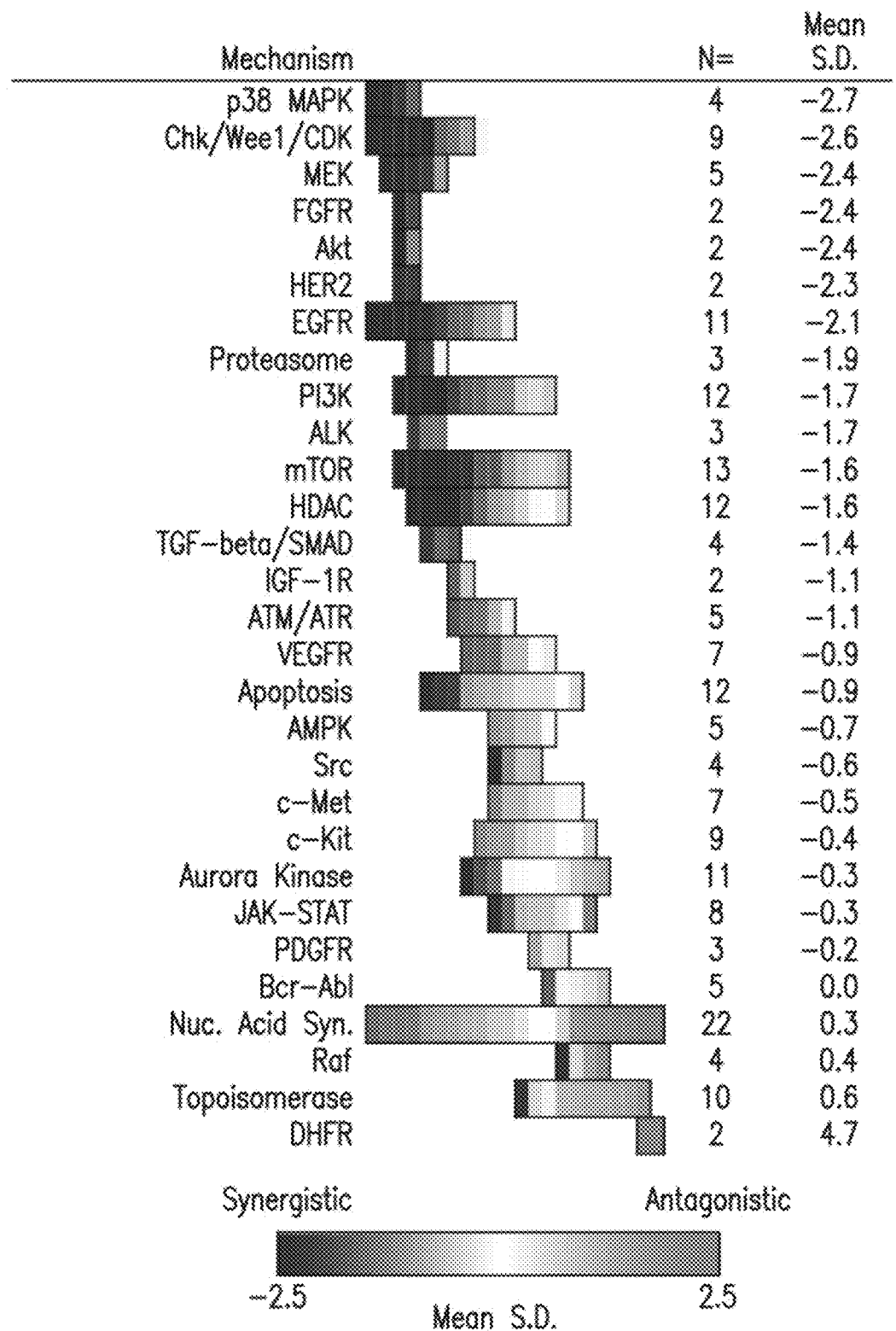
FIG. 4A shows a mechanism map indicating the relationship of each anti-cancer compound (grouped by mechanism of action). Scoring of relative synergism/antagonism was scored as the sum of the observed relationships for each compound with each gene. Scoring for drug is the mean of the observed distance $V_{AB}-V_A \times V_B$ measured in standard deviations (S.D.). Scoring for the mechanism group is the mean of all drugs within the group. Compounds are sorted from most synergistic (left) to most antagonistic (right).
Figure 4B:
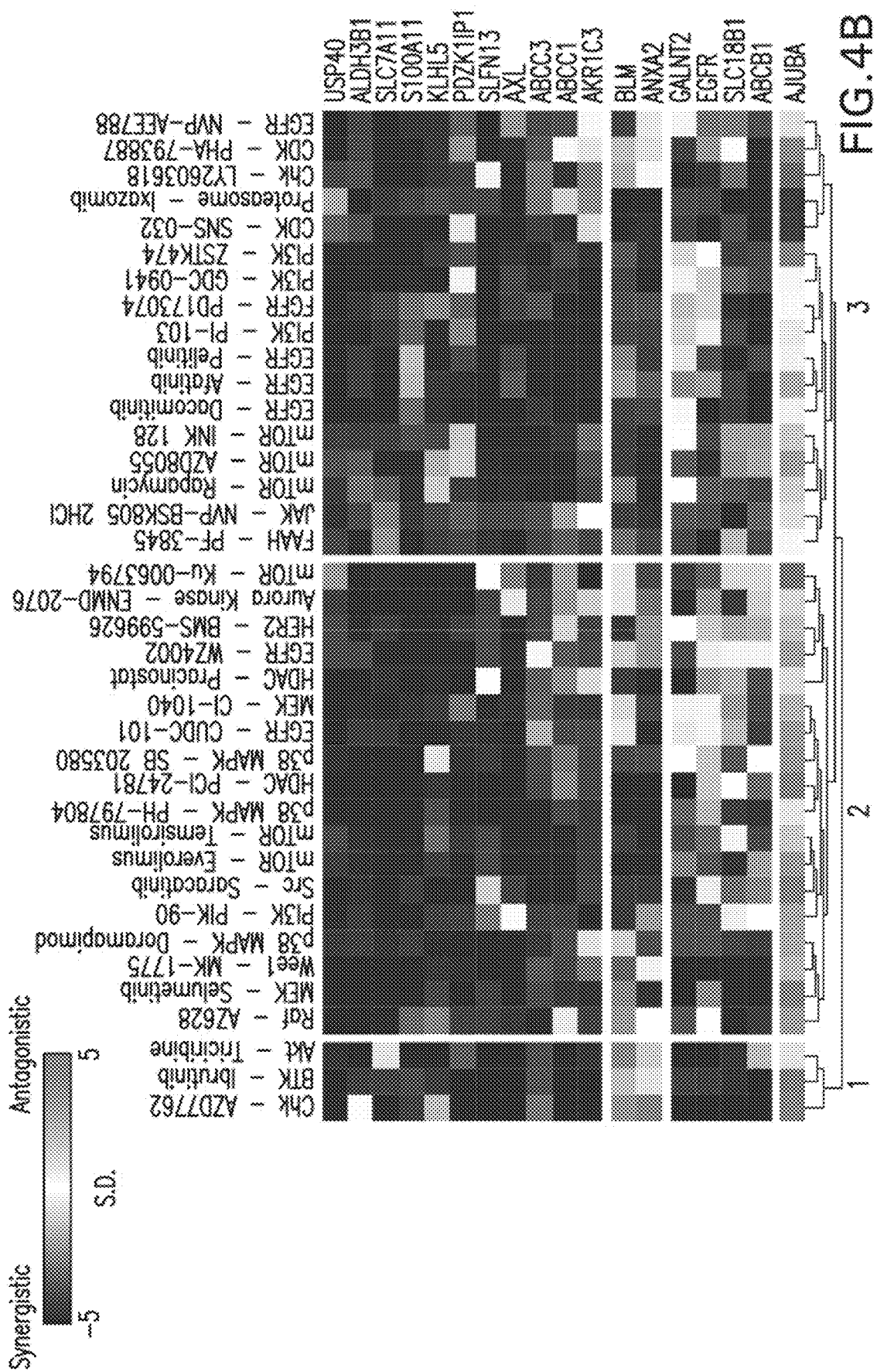
FIG. 4B shows hierarchical clustering for 40 compounds showing the highest synergy score measured using the mean distance $V_{AB}-V_A \times V_B$ as measured in standard deviations (S.D.).
Figure 4C:
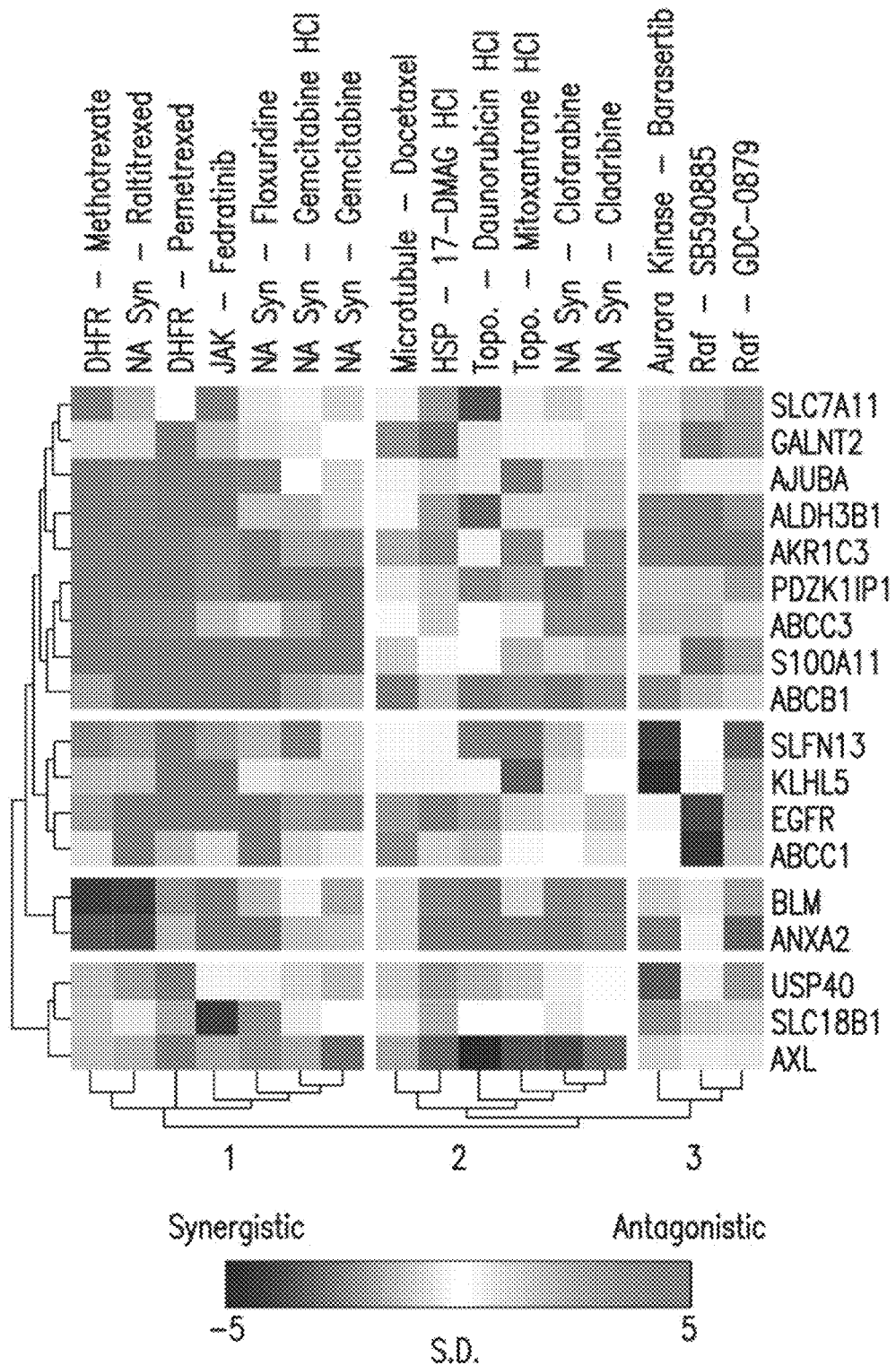
FIG. 4C shows hierarchical clustering for 20 compounds showing the highest antagonistic score measured using the mean distance $V_{AB}-V_A \times V_B$ as measured in standard deviations (S.D.). Abbreviations: NA Syn=DNA/RNA Synthesis, Topo.=Topoisomerase.

While the majority of TKIs synergize with gene knockdown, inhibitors of c-Met (hepatocyte growth factor receptor), and c-Kit (mast/stem cell growth factor) lack high synergism (FIG. 4A). Exceptions to these findings are high synergies observed between S100A11 and four of the c-Met inhibitors as well as between USP40 and four of the c-Kit inhibitors (FIGS. 8N and 8R). These results suggest that care should be paid to selection of combination drugs for these inhibitors to increase synergy and avoid antagonism.

Generally, HDAC inhibitors display strong and frequent synergism, however the HDAC inhibitors Mocetinostat and Entinostat are frequently antagonized by knockdown of specific genes. Knockdown of ABCB1, AKR1C3, ALDH3B1, and SLFN13 antagonize the effect of both drugs (FIGS. 8A, 8E, 8F, and 8Q). Examination of the specific HDAC targets of the antagonistic versus synergistic HDACi indicates that the two mostly antagonistic HDACi primarily target class I HDACs. In contrast, the six mostly synergistic HDACi (Pracinostat, PCI-24781, Belinostat, CUDC-101, AR-42, and Trichostatin A) are pan-HDAC or multiple class HDAC inhibitors. Further studies on this phenomenon should provide more insights on the most suitable HDAC targets.

Example 9. In Depth Characterization of S100A11 and KLHL5

Figure 5A:
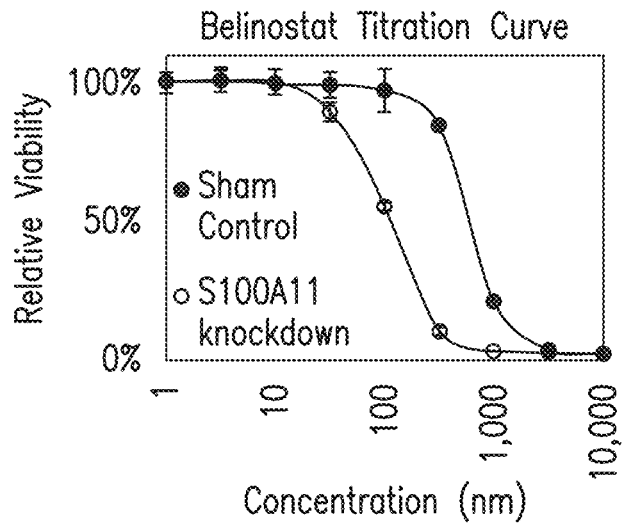
FIGS. 5A-5D show $GI_{50}$ values (FIGS. 5B and 5D) and full titration curves (FIGS. 5A and 5C) for a separate experimental confirmation for two HDAC inhibitors: Belinostat and Quisinostat (JNJ26481585). OVCAR-8 cells were treated with S100A11 siRNA (○) and compared to sham control (●). Serial dilution of drugs was used to determined $GI_{50}$ values. Belinostat indicates a 5.56-fold and Quisinostat a 5.53-fold dose reduction. Data represent means±s.d. from three replicates for each data point.
Figure 5B:
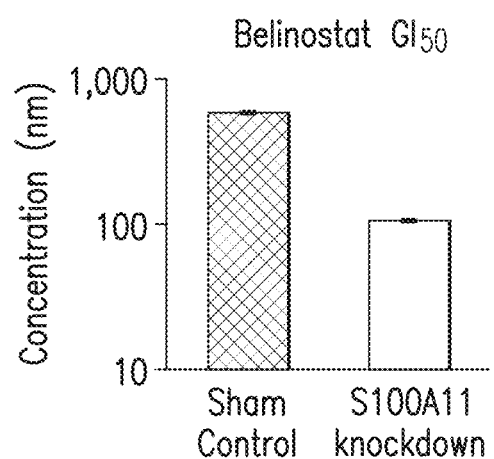

Results:

An important measure of synergism is the dosage reduction of a therapeutic compound by another agent. Titration screening with several compounds was performed to compare growth curves with and without knockdown of S100A11 or KLHL5. These genes showed synergy with compounds in intriguing patterns unique from other genes. S100A11 showed high synergism with the majority of HDAC inhibitors, while KLHL5 knockdown showed high synergism with Aurora kinase inhibitors. KLHL5 also was synergistic with other cell cycle inhibitors and PI3K-AKT-mTOR inhibitors. Titration curves and calculation of $GI_{50}$ were performed for twenty-four compounds. S100A1 siRNA decreased the $GI_{50}$ values by 5.56-fold and 5.53-fold for HDACi Belinostat and Quisinostat (JNJ26481585) in OVCAR-8 cells, respectively (FIG. 5A-5B).

Figure 5C:
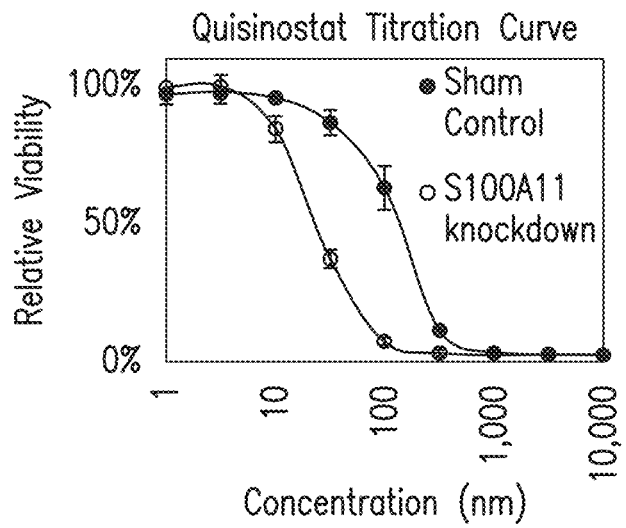
Figure 5D:
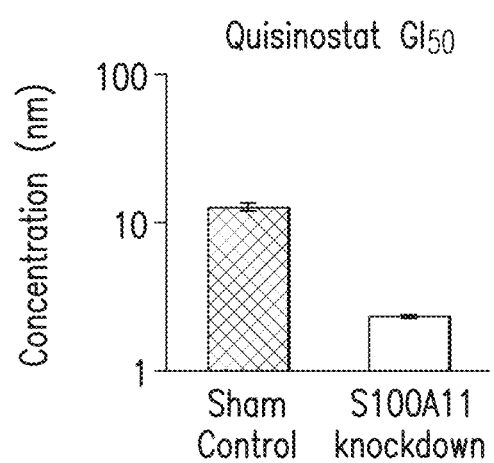
Figure 5E:
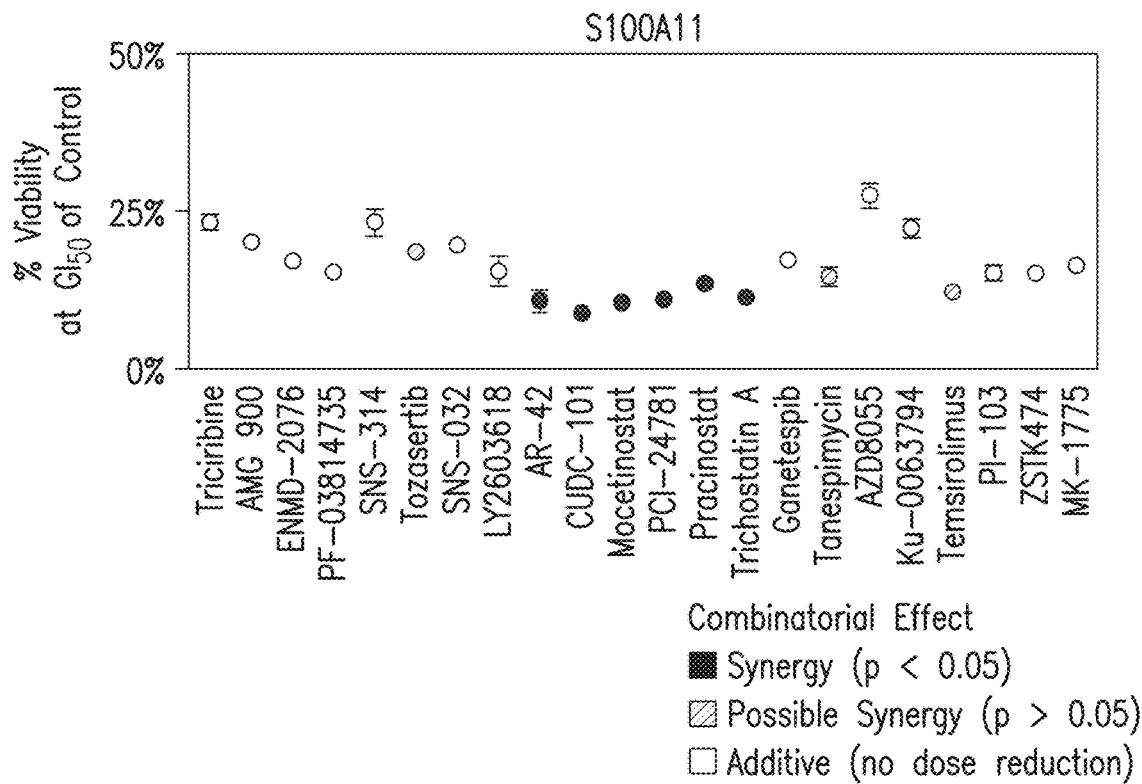
FIGS. 5E-5H show the results of twenty-two compounds with various mechanisms tested with S100A11 and KLHL5 knockdowns.
Figure 5F:
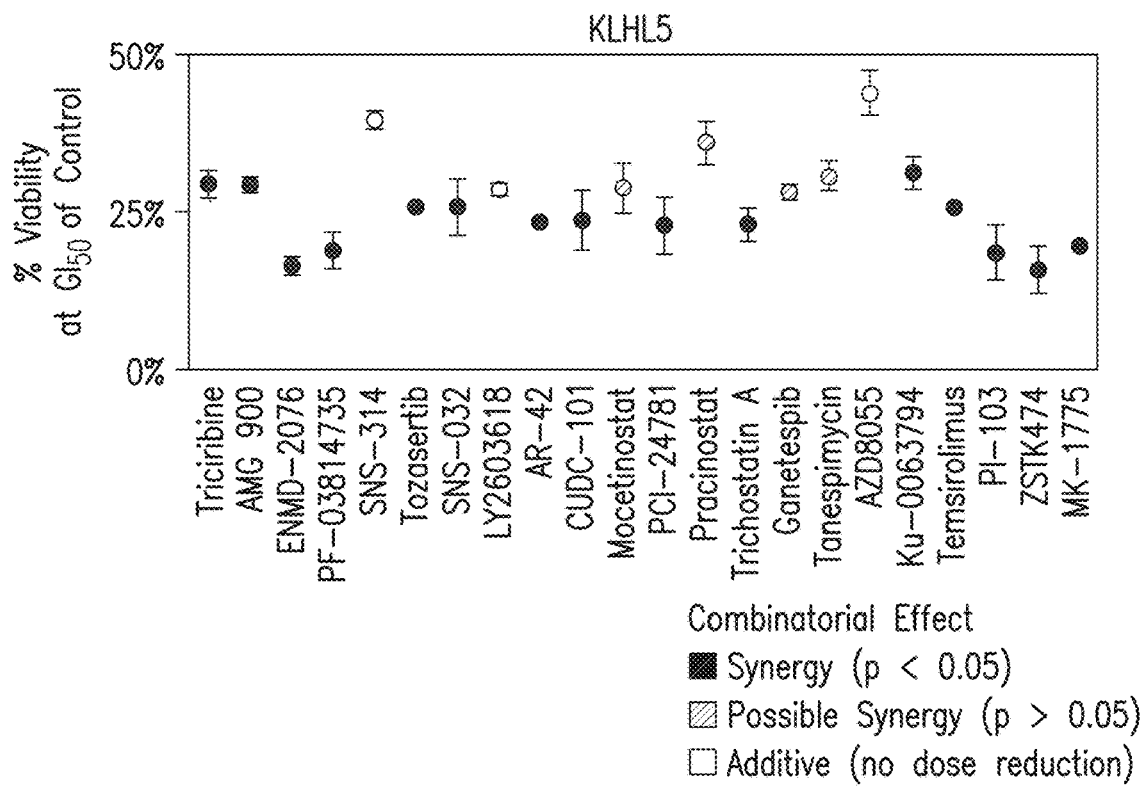
Figure 5G:
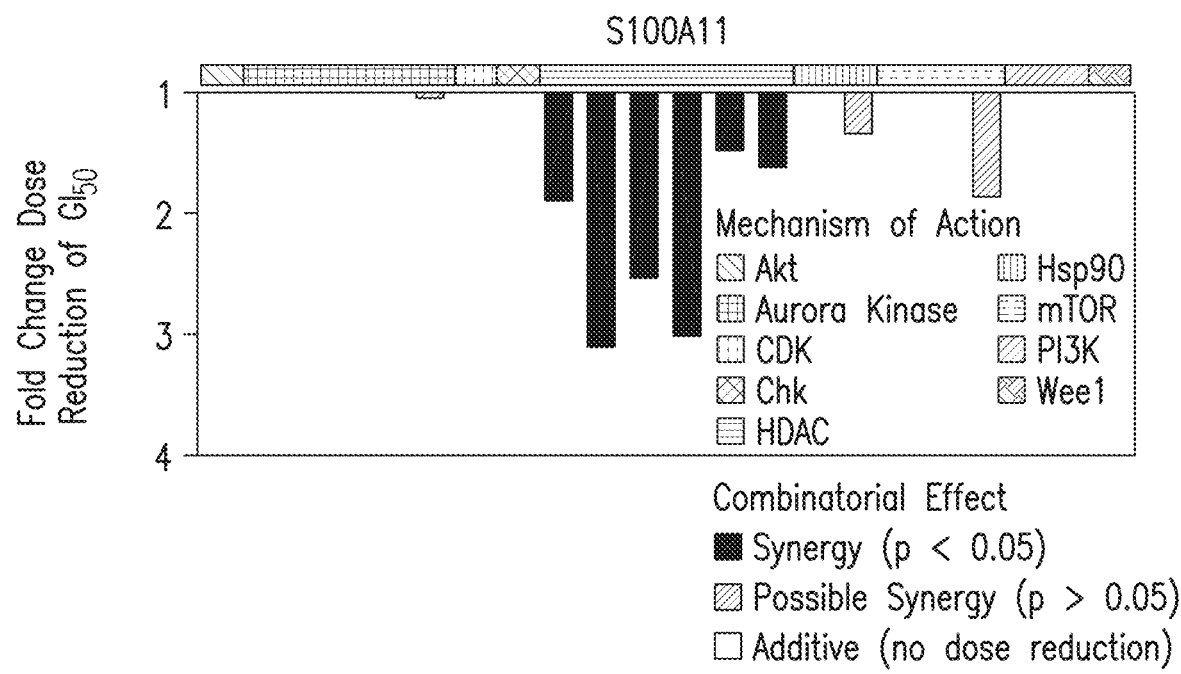
Figure 5H:
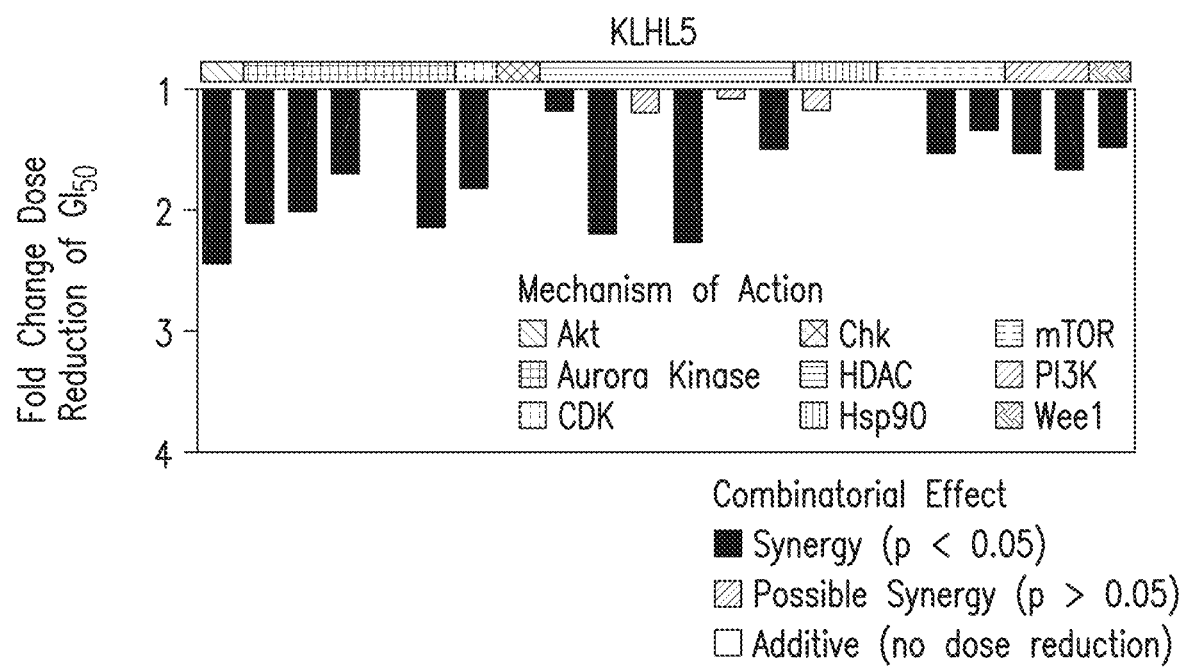

Similar calculations were performed with the twenty-two other compounds (FIG. 5C-5D). Viability curve shifts indicating concentration reduction were observed between S100A11 and the other HDACi as well as between KLHL5 and most Aurora Kinase inhibitors, Cell Cycle, and the PI3K-AKT-mTOR pathway. Comparable results were observed when $GI_{50}$ curve-shifts were tested on compounds in other cancer cell lines (data not shown). These results suggest that the screening data are largely valid.

TABLE 3

Sequences for siRNA, Product Numbers for TaqmanProbes, and Product Numbers for shRNA Lentivirus used.

| Gene | Sense Sequence | SEQ ID NO | Antisense Sequence | SEQ ID NO | Taqman probe (Thermo Fisher) | Santa Cruz shRNA Lentiviral Prod No |
|---|---|---|---|---|---|---|
| ABCB1 | CAUUCGCUAUGGCCGUGAAtt | 1 | UUCACGGCCAUAGCGAAUGtt | 2 | Hs00184500_m1 | sc-29395-V |
| ABCC1 | GGAUGUCAUCUGAAAUGGAtt | 3 | UCCAUUUCAGAUGACAUCCga | 4 | Hs01561502_m1 | sc-35962-V |
| ABCC3 | GGGUGUACGUGUACGUGGAtt | 5 | UCCACGUACACGUACACCCag | 6 | Hs00978473_m1 | sc-40748-V |
| AJUBA | GCGGCUCAAUGCCCGACAAtt | 7 | UUGUCGGGCAUUGAGCCGCtg | 8 | Hs01036974_m1 | sc-60066-V |
| AKR1C3 | GGAGUAAAUUGCUAGAUUUtt | 9 | AAAUCUAGCAAUUUACUCCgg | 10 | Hs00366267_m1 | sc-44464-V |
| ALDH3B1 | GGAGAGAAUUAACCAUUGAtt | 11 | UCAAUGGUUAAUUCUCUCCac | 12 | Hs00997594_m1 | sc-96544-V |
| ANXA2 | GCAAGUCCCUGUACUAUUAtt | 13 | UAAUAGUACAGGGACUUGCcg | 14 | Hs00743063_s1 | sc-270151-V |
| AXL | CAGCGAGAUUUAUGACUAUtt | 15 | AUAGUCAUAAAUCUCGCUGtt | 16 | Hs01064444_m1 | sc-29769-V |
| BLM | CGCUAGACAGAUAAGUUUAtt | 17 | UAAACUUAUCUGUCUAGCGtc | 18 | Hs00172060_m1 | sc-29808-V |
| EGFR | CGAAUAUUAAACACUUCAAtt | 19 | UUGAAGUGUUUAAUAUUCGta | 20 | Hs01076090_m1 | sc-29301-V |
| GALNT2 | GAUUGGAACUUGGUAUUCAtt | 21 | UGAAUACCAAGUUCCAAUCaa | 22 | Hs00189537_m1 | sc-75094-V |
| KLHL5 | CAGGCCGCCUUGAAUUAAAtt | 23 | UUUAAUUCAAGGCGGCCUGta | 24 | Hs01567850_g1 | sc-89298-V |
| PDZKI1P1 | GGUCCAGUGAGCAUGAGAAtt | 25 | UUCUCAUGCUCACUGGACCtg | 26 | Hs00173779_m1 | sc-72180-V |
| SL100A11 | GAACUAGCUGCCUUCACAAtt | 27 | UUGUGAAGGCAGCUAGUUCtg | 28 | Hs01056944_g1 | sc-60314-V |
| SLC18B1 | GUGCUGAUAUUAGUUGUAAtt | 29 | UUACAACUAAUAUCAGCACca | 30 | Hs00917799_m1 | sc-95546-V |
| SLC7A11 | GGCUGAUUUAUCUUCGAUAtt | 31 | UAUCGAAGAUAAAUCAGCCca | 32 | Hs00921938_m1 | sc-76933-V |
| SLFN13 | GCUGUAUACCAGAACAUAUtt | 33 | AUAUGUUCUGGUAUACAGCtt | 34 | Hs00431187_m1 | sc-94095_v |
| USP40 | GGAAACUAGCUGUUAUACAtt | 35 | UGUAUAACAGCUAGUUUCCtt | 36 | Hs00332716_m1 | sc-94351-V |
| ESD |  |  |  |  | Hs00382667_m1 |  |
| MRPL19 |  |  |  |  | Hs00183553_m1 |  |
| IPO8 |  |  |  |  | Hs00608519_m1 |  |
| Scramble Control | CGUUAAUCGCGUAUAAUACGCGUat | 37 | AUACGCGUAUAUACGCGAUUAACGac | 38 |  |  |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition comprising an effective amount of an inhibitor of a HDAC in combination with an effective amount of a siRNA that synergistically inhibits or reduces expression of a drug resistance gene, wherein the drug resistant gene is S100A11.

2. The pharmaceutical composition of claim 1, further comprising a chemotherapeutic agent.

3. A method for inhibiting proliferation of solid tumor cells, comprising administering a composition comprising an effective amount of an inhibitor of a HDAC in combination with an effective amount of a siRNA that synergistically inhibits or reduces the expression of a drug resistance gene wherein the drug resistance gene is S100A11 and wherein reducing the expression of the drug resistance gene increases the effectiveness of the inhibitor.

4. The method of claim 3, wherein the inhibitor is administered simultaneously with the siRNA.

5. The method of claim 3, further comprising administering to the solid tumor cells a PD-1 antagonist in combination with the inhibitor.

6. The method of claim 3, wherein the solid tumor cell is a lung cancer cell.

* * * * *